US007119189B2

(12) United States Patent
Kaupmann et al.

(10) Patent No.: US 7,119,189 B2
(45) Date of Patent: Oct. 10, 2006

(54) METABOTROPIC GABA$_{[B]}$ RECEPTORS, RECEPTOR-SPECIFIC LIGANDS AND THEIR USES

(75) Inventors: Klemens Kaupmann, Lörrach (DE); Bernhard Bettler, Allschwil (CH); Helmut Bittiger, Freiburg (DE); Wolfgang Fröstl, Basel (CH); Stuart J Mickel, Lausen (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/875,724

(22) Filed: Jun. 6, 2001

(65) Prior Publication Data

US 2002/0091250 A1    Jul. 11, 2002

Related U.S. Application Data

(63) Continuation of application No. 09/194,382, filed as application No. PCT/EP97/01370 on Mar. 19, 1997, now abandoned.

(51) Int. Cl.
| C07H 21/04 | (2006.01) |
| C12N 15/63 | (2006.01) |
| C12N 15/12 | (2006.01) |
| C12N 1/15 | (2006.01) |

(52) U.S. Cl. .................. 536/23.5; 435/6; 435/7.21; 435/69.1; 435/252.3; 435/325; 436/501; 530/300; 530/350; 514/2

(58) Field of Classification Search ............... 530/350, 530/351, 300; 536/23.5; 435/6, 7.1, 7.21, 435/69.1, 252.3, 320.1; 436/501; 514/2
See application file for complete search history.

(56) References Cited

U.S. PATENT DOCUMENTS

| 5,332,729 A | 7/1994 | Mickel et al. ............... 514/114 |
| 5,424,441 A | 6/1995 | Mickel et al. ............... 548/131 |

FOREIGN PATENT DOCUMENTS

| WO | WO 99/20751 | 4/1999 |
| WO | WO 99/21890 | 5/1999 |

OTHER PUBLICATIONS

Bowery and Brown, Nature 386(223-224)1997.*

(Continued)

*Primary Examiner*—Janet L. Andres
*Assistant Examiner*—Michael Brannock
(74) *Attorney, Agent, or Firm*—Peter J. Waibel; Edward J. Wilusz, Jr.

(57) ABSTRACT

The present invention provides purified GABA$_B$ receptors and receptor proteins derived from rat and human sources, as well as nucleic acids which encode such proteins. The proteins and nucleic acids of the invention share significant homology with the GABA$_B$ receptor and the DNA encoding it as specifically disclosed herein. The invention moreover provides methods for isolating other members of the GABA$_B$ receptor family using DNA cloning technology and probes derived from the sequences provided herein, as well as novel members of the GABA$_B$ receptor family isolated by such methods.

Furthermore, the invention relates to the use of GABA$_B$ receptors and receptor proteins and cells transformed with a gene encoding a GABA$_B$ receptor protein in a method for identifying and characterising compounds which modulate the activity of the GABA$_B$ receptor, such as GABA$_B$ receptor agonists and antagonists, which may be useful as pharmacological agents for the treatment of disorders associated with the central and peripheral nervous systems.

2 Claims, 6 Drawing Sheets

OTHER PUBLICATIONS

Hirouchi et al. Pharmacol. Rev. Commun. 8(151)96.*
Bowie et al., 1990, Science 247:1306-1310.*
Alexander et al., Proc. Natl. Acad. Sci. 89(3352-3356)1992.*
GenBank accession No. Z44106, Nov. 1999.*
Sambrook, J. Molecular Cloning: a Laboratory Manual, pp. 16.3-16.22, 1989.*
Benjamini-E., eds, Immunology A Short Course, 1989.*
SIGMA Chemical Company Catalogue, 1994, p. 40.*
Ausubel et al., (Eds.) Short Protocols in Molecular Biology, "A Compendium of Methods AR from Current Protocols in Molecular Biology", Greene Publishing Associates and Willey-Interscience, New York, pp. 185, 186, 190 and 191 (1989).
Bertrand et al., Am. J. Resp. Crit. Care Med., vol. 149, "Involvement of a Gabab Receptor as Subtype in the Prejunctional Modulation of the Peptidergic Bronchospasm Evoled by Vagal Stimulation in Guinea Pigs", p. A900 (1994).
Bittiger et al., In GABA; Receptors, Transporters and Metabolism, Tanaka, C. and Bowery, N.G. AB (Eds.), Basel/Switzerland, "GABAB Receptor Antagonists: Potential Therapeutic Applications", pp. 297-305 (1996).
Bittiger et al., Pharmacol. Commun., vol. 2, Nos. 1-2, "H-CGP 54626: A Potent Antagonist AT Radioligand for GabaB Receptors", p. 23 (1992).
Bittiger et al., TiPS, vol. 14, "GABAB receptor antagonists: from synthesis to therapeutic AA applications", pp. 391-394 (1993).
Bledsoe et al., J. Mol. Evol., vol. 30, "Molecular Homology and DNA Hybridization", pp. 425-433 AC (1990).
Bowery et al., Drug Res., vol. 42(1), No. 2a, "GABAB Receptors as Targets for Drug Action", pp. AD 215-223 (1992).
Bowery, NG and Brown, DA, Nature 386 (223-224 (1997).
Bowie et al., Science 247 pp. 1306-1310 (1990).
Chomczynski et al., Anal. Biochem., vol. 162, "Single-Step Method of RNA Isolation by Acid AE Guanidinium Thiocyanate-Phenol-Chloroform Extraction", pp. 156-159 (1987).
Davies et al., Journal of Physiology, vol. 424, "Paired-Pulse Depression of Monosynaptic Gaba-AF Mediated Inhibitory Postsynaptic Responses in Rat Hippocampus", p. 513-531 (1990).
Devereux et al., Nucleic Acids Research, vol. 12, No. 1 "A comprehensive set of sequence and AG analysis programs for the VAX", pp. 387-395 (1984).
Dutar et al., Nature, vol. 332, "A physiological role for GABAB receptors in the central nervous AH system", pp. 156-158 (1988).
Froestl et al., J. Med. Chem., vol. 38, "Phosphinic Acid Analogues of GABA. 1. New Potent and AJ Selective GABAB Agonists", pp. 3297-3312 (1995).
Froestl et al., Pharmacology Communications, vol. 2, Nos. 1-2, "Chemistry of New GABAB AI Antagonists", pp. 52-56 (1992).
Froestl et al.,J. Med. Chem., vol. 38, "Phosphinic Acid Analogues of GABA. 2. Selective, Orally AK Active GABAB Antagonists", pp. 3313-3331 (1995).
Gasparini, GENOMICS, vol. 31, "Hereditary hemochromatosis; generation of a transcription map AJ within a rfined and extended map of HLA 1 class region", pp. 319-326 (1996).
GenBank accession No. Z44106, cDNA. Nov. 14, 1994.
GenBank Accession No. D80024 -sequence comparison (1995). AK.
GenBank Accession No. D80024 (1995) AL .
GenBank Accession No. LO1481 (1993) AM.
GenBank Accession No. T07518 (1993) AN.
GenBank Accession No. W48985 (1996) M.
GenBank Accession No. W51392 (1996) AC.
GenBank Accession No. X90542 (1996) AB.
Hill et al., Journal of Neurochemistry, vol. 42, No. 3, "Inhibition of GABAB Receptor Binding by AL Guanyl Nucleotides", pp. 652-657 (1984).
Hirouch et al., Pharmacol. Rev. Commun., vol. 8, "Molecular Biological Approaches to the GABAB AM Receptor", p. 151(1996).

Isaacson et al., Neuron, vol. 10, "Local and Diffuse Synaptic Actions of GABA in the AN Hippocampus", pp. 165-175 (1993).
Ishihara et al., The EMBO Journal, Voi. 10, No. 7, Molecular cloning and expression of a cDNA AA encloding the secretin receptor, pp. 1635-1641 (1991).
Jarolimek et al., Neurosci. Lett., Voi. 154, "CGP 55845A blocks baclofen, y-aminobutyric acid and AB inhibitory postsynaptic potassium currents in guinea pig CA3 neurons", pp. 31-34 (1993).
Johansen et al., Experimental Brain Research, Voi. 84, "Inhibition in postischemic rat AC hippocampus: GABA receptors, GABA release and inhibitory postsynaptic potentials", pp. 529-537 (1991).
Jones et al., Nature, vol. 396, "GABAB receptors function as a heteromeric assembly of AD the subunits GABABR1 and GABABR2", pp. 674-678 (1998).
Karlsson et al., European Journal of Pharmacology, Voi. 148, "Phaclofen: a GABAB blocker AD reduces long-duration inhibition in the neocortex", pp. 485-486 (1988).
Kaupmann et al., Nature, Voi. 386, "Expression cloning of GABAB receptors uncovers similarity to AE metabotropic glutamate receptors", 239-246 (1997).
Kaupmann et al., Nature, vol. 396, GABAB-receptor subtypes assemble into functional AE heteromeric complexes, pp. 683-686 (1998).
Kuner et al., Science, vol. 283, "Role of heteromer formation in GABAB receptor function", AF pp. 74-77 (1999).
Kuriyama et al., Neuroscience Research, Voi. 17, "Structure and function of cerebral GABAA and AF GABAB receptors" pp. 91-99 (1993).
Kyte et al., J. Mol. Bioi., Voi. 157, "A Simple Method for Displaying the Hydropathic Character of a AG Protein", pp. 105-132 (1982).
Lambert et al., Neuroscience Letters, Voi. 107, "Blockade of the late IPSP in rat CA1 hippocampal AH neurons by 2-hydroxy-saclofen", pp. 125-128 (1989).
Mansour et al., Nature, Voi. 336, "Disruption of the proto-oncogene ;nt-2 in mouse embryo-derived AI stem cells: a general strategy for targeting mutations to non-selectable genes", pp. 348-352 (1988).
McCormick et al., Journal of Neurophysiology, Voi. 62, No. 5, "GABA as an Inhibitory AJ Neurotransmitter in Human Cerebral Cortex", pp. 1018-1026 (1989).
Milligan et al., Journal of Medicinal Chemistry, Voi. 36, No. 14, "Current Concepts in Antisense AK Drug Design", pp. 1923-1937 (1993).
Mouamed, K. M., et al., Science 252, pp. 1318-1321 (1991).
Müller et al., Neuroscience Letters, Voi. 102, "Carbachol reduces IK,Baclofen. but not IK,GABA in guinea AL pig hippocampal slices" pp. 229-234 (1989).
Nakayasu et al., J. Bioi. Chem., Voi. 268, "Immunoaffinity Purification and Characterization ofy-AminobutyricAcid (GABA)B Receptor from Bovine Cerebral Cortex", pp. 8658-8664.11993).
Nathan et al., Brain Research, Voi. 531, "GABAB receptors playa major role in paired-pulse AN facilitation in area CA 1 of the rat hippocampus", pp. 55-65 (1990).
Ngo, et al., The Protein Folding Problem and Tertiary Structure, Birkhauser (1994).
Olpe et al., Clin. Neuropharmacol., vol. 13, "The role of GABA-B receptors in the control of AA neuronal excitability" Suppl. 2, pp. 396-397 (1990).
Ong et al., Life Sciences, vol. 46, "Gaba-Receptors in Peripheral Tissues", pp. 1489-1501 (1990) AB.
Runeberg et al., Acta Chemica Scandinavica, Voi. 12, "Phenol Dehydrogenations VIII. Synthesis of AC Magnolol, Supply Catalog", pp. 188-192 (1958).
Sambrook, J., et al., Molecular Cloning: A Laboratory Manual (1989).
Soltesz et al., Brain Research, vol. 479, Optic tract stimulation evokes GABAA but not GABAB AD IPSPs in th rat ventral lateral geniculate nucleus, pp. 49-55 (1989).

Statagene Cloning Systems, Supply Catalog, 800-424-5444, pp. 154-159 (1994) AE.

Totaro et al., GENOMICS, vol. 31, "Hereditary Hemochromatosis: Generation ofa AF Transcription Map within a Redefined and Extended Map of the HLA Class I Region",.pp. 319-326 (1996).

von Heijne, Nucl. Acids Res., vol. 14, No. 11, "A new method for predicting signal sequence AG cleavage sites", pp. 4683-4690 (1986).

Wells, Biochemistry 29, pp. 8509-8517 (1990).

White et al., Nature, vol. 396, "Heterodimerization is required for the formation of a AG functional GABAB receptor", pp. 679-682 (1998).

Yadav et al., Can. J. Chem., vol. 69, "Free-radical based cycloalkanol synthesis and annulation .AH from thioacetal precursors", pp. 779-789 (1991).

Zuiderwijk et al., Eur. J. Pharmacol., vol. 307, "Effects of uptake carrier blockers SK &F 89976-A AI and L-trans-PDC on in vivo release of amino acids in rat hippocampus", pp. 275-282 (1996).

* cited by examiner

METABOTROPIC GABA $_{[B]}$ RECEPTORS, RECEPTOR-SPECIFIC LIGANDS AND THEIR USES

This application is a continuation of U.S. application Ser. No. 09/194,382, filed Nov. 25, 1998, now abandoned which is a 371 of International Application No. PCT/EP97/01370 filed Mar. 19, 1997.

The present invention relates to nucleic acids encoding proteins of the GABA$_B$ receptor family, as well as proteins encoded thereby and the use of such proteins for the development of pharmacological agents.

Gamma-aminobutyric acid (GABA) is the major inhibitory neurotransmitter found in the brain and peripheral nervous system. Receptors for GABA have been divided into two subfamilies, the GABA$_A$ and GABA$_B$ receptors. Of these, GABA$_A$ receptors are involved in fast inhibitory signal transmission, whilst GABA$_B$ receptors appear to be involved in modulation of neurotransmission. Pre-synaptic GABA$_B$ receptors influence the release of neurotransmitters and neuropeptides such as GABA, glutamate, noradrenaline, dopamine, 5-hydroxytryptamine, substance P, cholecystokinin and somatostafin, while post-synaptic GABA$_B$ receptors are coupled to potassium channels via G proteins and mediate late inhibitory post-synaptic potentials (IPSPs). The effect of the activation of both subtypes of the GABA$_B$ receptor is to modulate synaptic transmission.

GABA$_B$ receptors are located throughout the central and peripheral nervous systems (see Ong and Kerr, Life Sciences, (1990) 46,1489–1501; Bowery et at., Drug Res. (1992) 42(1), 2a, 215–223), and are thus involved in the regulation of a wide variety of neurally-controlled physiological responses, from memory and learning to muscle contraction. This makes the GABA$_B$ receptor a target for pharmaceutical agents intended to treat central and peripheral neural disorders, and indeed a variety of GABA$_B$ agonists and antagonists are known and have been proposed for use in therapy (Bittiger et al., in *GABA: Receptors, Transporters and Metabolism*, Tanaka, C., and Bowery, N. G. (Eds). Birkhäuser Verlag Basel/Switzerland (1996), 297–305; Bittiger et al, Trends Pharmacol. Sci., 14, 391–394, 1993; Froestl et al, J. Med. Chem., 38, 3297–3312, 1995; Froestl et al, Ibid., 3313–3331). For example, in Alzheimer's disease and other dementias such as Age Associated Memory Impairment and Multi Infarct Dementia, loss of cognitive function is associated with reduced levels of a number of neurotransmitters in the brain. In particular, a deficit in L-glutamate is expected to cause a major loss of cognitive functions, since L-glutamate appears to be crucially involved in the processes underlying memory formation and learning. GABA acts directly at many synapses to reduce the release of L-glutamate by acting on GABA$_B$ hetero-receptors. Thus, GABA$_B$ receptor antagonists are indicated for the treatment of dementias, and indeed have been shown to improve cognitive functions in animal studies. In addition, GABA$_B$ receptor antagonists are expected to be active in psychiatric and neurological disorders such as depression, anxiety and epilepsy (Bittiger et al., 1993, 1996, Op. Cit.; Froestl et al., 1995, Op. Cit.). GABA$_B$ receptor agonists are known as antispastic agents, and in peripheral nervous system applications, agonists are expected to be beneficial in bronchial inflammation, asthma and coughing (Bertrand et al., Am. J. Resp. Crit. Care Med. 149, A900, 1994). GABA is moreover associated with activity in the intestine, the cardiovascular system, gall and urinary bladders, and a variety of other tissues (Ong and Kerr, Op. Cit.).

GABA action in each of the above cases is known to be mediated by GABA$_B$ receptors, making the receptors targets for pharmacological agents designed to treat a number of disorders.

Despite the advanced state of molecular biology and protein purification technology, and the evident desirability of obtaining a purified GABA$_B$ receptor for pharmacological studies, the GABA$_6$ receptor previously has not been cloned or purified to homogeneity. A previous report of its partial purification (Nakayasu et al, J. Biol. Chem., 268, 8658–8664, 1993) appears to have been inaccurate, relating to an 80 kDa protein, which we now know to be too small. In order to be able to clone the GABA$_B$ receptor, we have developed a number of GABA$_B$ receptor-specific ligands. By expression cloning using one such highly selective GABA$_B$ receptor ligand labelled to high specific radioactivity, we have now cloned different GABA$_B$ receptors from rat and human sources, sequenced them and expressed the respective recombinant receptors in mammalian cell culture.

SUMMARY OF THE INVENTION

The present invention provides purified GABA$_B$ receptors and GABA$_B$ receptor proteins, as well as nucleic acids which encode such proteins. The proteins and nucleic acids of the invention share significant homology with the GABA$_B$ receptors and the DNAs encoding them as specifically disclosed herein. In particular, there are provided two GABA$_B$ receptor proteins designated GABA$_B$R1a and GABA$_B$R1b which are distinct variants of GABA$_B$ isolated from rat. The respective cDNA and derived amino acid sequences are set forth in SEQ ID Nos. 1, 2, and 5, 6, respectively. Furthermore, there are provided two human GABA3 receptor clones termed GABA$_B$R1a/b (representing a partial receptor clone) and GABA$_B$R1b (representing a full-length receptor clone) isolated from human sources. The respective cDNA and derived amino acid sequences are set forth in SEQ ID Nos. 3, 4, and 7, 8, respectively.

The GABA$_B$ receptors and GABA$_B$ receptor proteins of the invention show specific binding to one or more of the selective GABA$_B$ receptor antagonists of Formula I and Formula II:

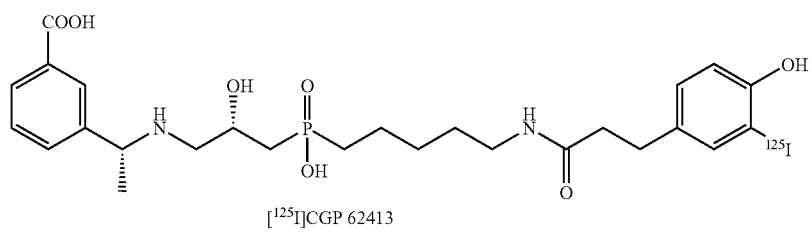

[$^{125}$I]CGP 62413

-continued

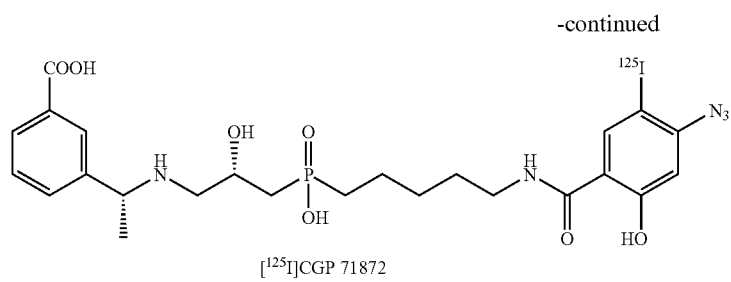

[125I]CGP 71872

The invention accordingly provides the compounds of Formula I and Formula II. Moreover, binding of the these selective $GABA_B$ receptor antagonists may be competed with other selective $GABA_B$ receptor agonists or antagonists, such as the compound of Formula III and Formula IV:

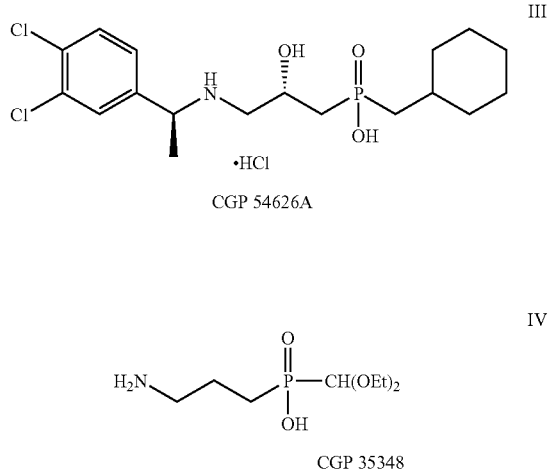

CGP 54626A

CGP 35348

The invention moreover provides methods for isolating other members of the $GABA_B$ receptor family using DNA cloning technology and probes derived from the sequences provided herein, as well as novel members of the $GABA_B$ receptor family isolated by such methods.

Furthermore, the invention relates to the use of $GABA_B$ receptors and $GABA_B$ receptor proteins and cells transformed with a gene encoding such a $GABA_B$ receptor or receptor protein in a method for identifying and characterising compounds which modulate the activity of the $GABA_B$ receptor(s), such as $GABA_B$ receptor agonists and antagonists, which may be useful as pharmacological agents for the treatment of disorders associated with the central and peripheral nervous systems. In particular, $GABA_B$ receptor antagonists can e.g. be useful as cognition enhancers, nootropics, antidepressants and anxiolytics for the treatment of cerebral insufficiency, depression, anxiety, epilepsy of the petit mal type, schizophrenia and myopia, whereas $GABA_B$ receptor agonists can e.g. be useful in the treatment of disorders such as spasticity, trigeminal neuralgia, asthma, cough, emesis, ulcers, urinary incontinence and cocaine addiction.

DETAILED DESCRIPTION OF THE INVENTION

Figure 1A:
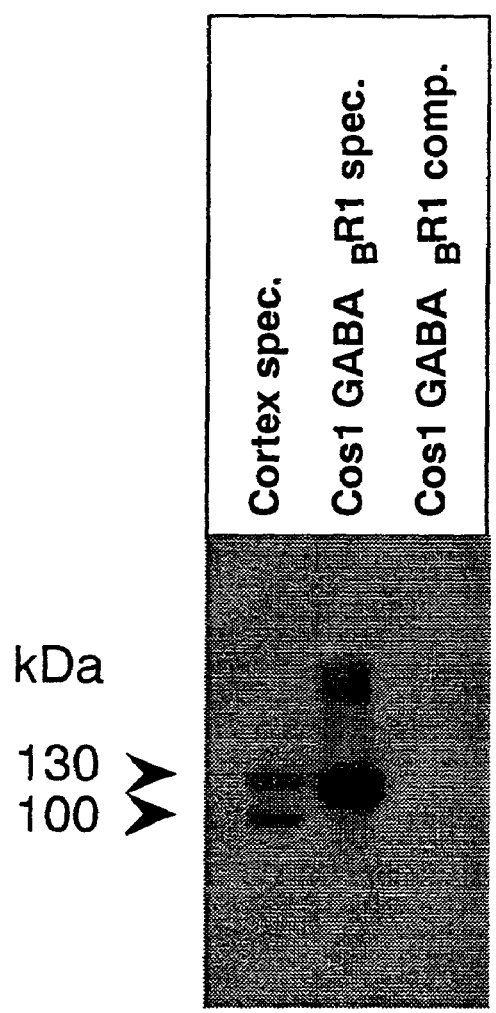
FIG. 1a depicts the expression of the recombinant $GABA_B$ R1a receptor in COS1 cells. Membranes from rat cortex membranes (lane 1) and COS1 cells transfected with the $GABA_B$ R1a rat-cDNA (lanes 2 and 3) are labelled with the photoaffinity ligand [125I]CGP 71872. Autoradiography of a 6% SDS gel with 25 μg protein loaded per lane is shown. Lanes 1 and 2: Specific binding with 0.6 nM [125I]CGP 71872. Lane 3: Control experiment where specific binding with 0.6 nM [125I]CGP 71872 is competed with 1 μM of unlabeled CGP 54626A (an antagonist specific for $GABA_B$ receptors). The apparent molecular weight of native and recombinant $GABA_B$ receptors are estimated from gel mobilities relative to those of SDS-PAGE standards (Bio-Rad).

The invention relates to purified $GABA_B$ receptors and $GABA_B$ receptor proteins, nucleic acids coding therefore and various applications thereof. Before the present invention, the $GABA_B$ receptor has not been available in purified form, but only as crude membrane preparations. For the first time, the present invention enables the production of different but related $GABA_B$ receptors in a substantially purified form, by means of recombinant DNA technology. In general, it is expected that such proteins in glycosylated form will have an observed molecular weight of between 100 and 130 kDa, whereas the unglycosylated forms will have an observed molecular weight of between 90 and 110 kDa, respectively.

$GABA_B$ receptors according to the invention are G-protein coupled modulators of neurotransmitter activity which are responsive to GABA. They may be defined by binding to labelled ligands which are selective for $GABA_B$ receptors, in particular $[^{125}I]CGP$ 62413 and $[^{125}I]CGP$ 71872. Functional studies are moreover possible in which a recombinant $GABA_B$ receptor is expressed in cell systems containing G-proteins and effectors such as ionic channels which can be activated by GABA and $GABA_B$ receptor agonists.

Proteins according to the invention may be defined electrophysiologically in transgenic or knockout animals, for example in terms of their responsiveness in assays for the $GABA_B$ receptor(s) which are known in the art, such as the measurement of late IPSPs (inhibitory post-synaptic potentials), paired-pulse-inhibition or (−)-baclofen-induced depression of field EPSPs (excitatory post-synaptic potentials). $GABA_B$ receptors are responsible for the observation of IPSPs as a result of indirect coupling to potassium channels in neurons, so established agonists and antagonists of $GABA_B$ receptors may be used to determine the presence of $GABA_B$ receptors in neuronal preparations by assaying for their effect on IPSPs.

Advantageously, however, $GABA_B$ receptor proteins according to the invention are assessed by their susceptibility to CGP64213 and CGP71872 as measured by paired-pulse widening of field EPSPs. Both said compounds abolish paired-pulse widening normally associated with $GABA_B$ receptors, since they are effective $GABA_B$ autoreceptor antagonists. Preferably, therefore, the activation of $GABA_B$ receptor proteins according to the invention is specifically inhibited by CGP64213 and CGP71872. Examples of specific inhibition by these compounds are set out hereinbelow.

As used herein, the term "$GABA_B$ receptor(s)" refers to the proteins whose sequences are substantially those set forth in SEQ ID Nos. 2 and 8, while the term "$GABA_B$ receptor proteins" includes derivatives and variants such as e.g. splice variants thereof which are related structurally and/or functionally to the $GABA_B$ receptor(s). Preferred $GABA_B$ receptor proteins according to the invention are e.g. those set forth in SEQ ID Nos. 4 and 6, and share at least one common structural determinant with the $GABA_B$ receptors having the amino acid sequences set forth in SEQ ID Nos. 2 and 8, respectively. "Common structural determinant" means that the derivative in question comprises at least one structural feature of the $GABA_B$ receptors set out in SEQ ID Nos. 2 and 8. Structural features includes possession of an epitope or antigenic site that is capable of cross-reacting with antibodies raised against a naturally occurring or denatured $GABA_B$ receptor polypeptide or fragment thereof, possession of amino acid sequence identity with the $GABA_B$ receptor(s) and features having common a structure/function relationship. Thus the $GABA_B$ receptor proteins as provided by the present invention include amino acid mutants, glycosylation variants and other covalent derivatives of the $GABA_B$ receptor(s) which retain the physiological and/or physical properties of the $GABA_B$ receptor(s).

Further included within the scope of the term "$GABA_B$ receptor proteins" are naturally occurring variants of the $GABA_B$ receptor(s) found within a particular species, preferably a mammal. Such a variant may be encoded by a related gene of the same gene family, by an allelic variant of a particular gene, or represent an alternative splicing variant of the $GABA_B$ receptor gene. Variants according to the invention have the same basic function as the $GABA_B$ receptor(s), but may possess divergent characteristics consistent with their nature as variants. For example, it is expected that the $GABA_B$ receptors are members of a family of $GABA_B$ receptor proteins, the isolation and characterisation of which is enabled for the first time by the present invention. Different members of the $GABA_B$ receptor family may be expected to have different activity profiles, possibly according to differences in their tissue-specific localisation and role in modulating neuronal signalling.

Moreover, the present invention enables the isolation and characterisation of further $GABA_B$ receptors, $GABA_B$ receptor proteins and $GABA_B$ receptor protein-encoding nucleic acids from any species, including man. The provision of sequence data enables the person skilled in the art to apply standard hybridisation methodology, as is known in the art and set out by way of example hereinbelow, to isolate any desired $GABA_B$ receptor-encoding nucleic acid.

The invention further comprises derivatives of the $GABA_B$ receptor(s), which retain at least one common structural determinant of the $GABA_B$ receptor(s). For example, derivatives include molecules wherein the protein of the invention is covalently modified by substitution, chemical, enzymatic, or other appropriate means with a moiety other than a naturally occurring amino acid. Such a moiety may be a detectable moiety such as an enzyme or a radioisotope.

Derivatives which retain common structural determinants can be fragments of the $GABA_B$ receptor(s). Fragments of the $GABA_B$ receptor(s) comprise individual domains thereof, as well as smaller polypeptides derived from the domains. Preferably, smaller polypeptides derived from the $GABA_B$ receptor(s) according to the invention define a single feature which is characteristic of the $GABA_B$ receptor(s). Fragments may in theory be almost any size, as long as they retain one feature of the $GABA_B$ receptor(s). Preferably, fragments will be between 5 and 600 amino acids in length. Longer fragments are regarded as truncations of the full-length $GABA_B$ receptor(s) and generally encompassed by the term "$GABA_B$ receptor(s)". Preferably, said fragments retain the functional activity of the $GABA_B$ receptor(s). Such fragments may be produced by persons skilled in the art, using conventional techniques, by removing amino acid residues from the $GABA_B$ receptor proteins of the invention which are not essential for a particular functional aspect of the $GABA_B$ receptor proteins. Determination of functional aspects of a $GABA_B$ receptor protein may be made employing pharmacological or electrophysiological assays as herein described, and particularly by assays which monitor the ability of the $GABA_B$ receptor protein to bind GABA or a GABA mimic, or to couple to G proteins.

Derivatives of the $GABA_B$ receptor(s) also comprise mutants thereof, which may contain amino acid deletions, additions or substitutions, subject to the requirement to maintain at least one feature characteristic of the $GABA_B$ receptor(s). Thus, conservative amino acid substitutions may be made substantially without altering the nature of the $GABA_B$ receptor(s). Substitutions and further deletions may moreover be made to the fragments of $GABA_B$ receptor proteins comprised by the invention. $GABA_B$ receptor protein mutants may be produced from a DNA encoding a $GABA_B$ receptor protein which has been subjected to in vitro mutagenesis resulting e.g. in an addition, exchange and/or deletion of one or more amino acid encoding triplets. For example, substitutional, deletional or insertional variants of the $GABA_B$ receptor(s) can be prepared by recombinant methods and screened for immuno- or physiological crossreactivity with the native forms of the $GABA_B$ receptor(s).

Mutations may be performed by any method known to those of skill in the art. Preferred, however, is site-directed mutagenesis of a nucleic acid sequence encoding the polypeptide of interest. A number of methods for site-directed mutagenesis are known in the art, from methods employing single-stranded phage such as M13 to PCR-based techniques (see "PCR Protocols: A guide to methods and applications", M. A. Innis, D. H. Gelfand, J. J. Sninsky, T. J. White (eds.). Academic Press, New York, 1990). Preferably, the commercially available Altered Site II Mutagenesis System (Promega) may be employed, according to the directions given by the manufacturer.

The fragments, mutants and other derivatives of the $GABA_B$ receptor(s) preferably retain substantial homology with the $GABA_B$ receptor(s). As used herein, "homology" means that the two entities share sufficient characteristics for the skilled person to determine that they are similar in origin and function. Preferably, homology is used to refer to sequence identity. Thus, the derivatives of the $GABA_B$ receptor(s) preferably retain substantial sequence identity with the sequences set forth in SEQ ID Nos. 2 and 8, respectively.

"Substantial homology", where homology indicates sequence identity, means more than 30% sequence identity, preferably more than 65% sequence identity and most preferably a sequence identity of 80% or more.

According to a further aspect of the present invention, there are provided nucleic acids encoding $GABA_B$ receptors and $GABA_B$ receptor proteins (SEQ ID Nos. 1, 7, and 3, 5, respectively). In addition to being useful for the production of recombinant $GABA_B$ receptors and receptor proteins, these nucleic acids are also useful as probes, thus readily enabling those skilled in the art to identify and/or isolate nucleic acids encoding further members of the $GABA_B$ receptor family and variants thereof as set forth hereinbefore.

In another aspect, the invention provides nucleic acid sequences that are complementary to, or are capable of hybridising to, nucleic acid sequences encoding the $GABA_B$ receptors or receptor proteins. Preferably, such nucleic acids are capable of hybridising under high or moderate stringency, as defined hereinbelow.

Furthermore, nucleic acids according to the invention are useful in a method determining the presence of a $GABA_B$ receptor- or receptor protein-specific nucleic acid, said method comprising hybridising the DNA (or RNA) encoding (or complementary to) the $GABA_B$ receptor or receptor protein to test sample nucleic acid and determining the presence of the $GABA_B$ receptor- or receptor protein-specific nucleic acid.

The invention also provides a method for amplifying a nucleic acid test sample comprising priming a nucleic acid polymerase (chain) reaction with nucleic acid (DNA or RNA) encoding a $GABA_B$ receptor or receptor protein, or a nucleic acid complementary thereto.

Isolated $GABA_B$ receptor- or receptor protein-specific nucleic acids include nucleic acids that are free from at least one contaminant nucleic acid with which they are ordinarily associated in the natural source of $GABA_B$ receptor- or receptor protein-specific nucleic acids or in crude nucleic acid preparations, such as DNA libraries and the like. Isolated nucleic acids thus are present in other than in the form or setting in which they are found in nature. However, isolated $GABA_B$ receptor and receptor protein encoding nucleic acids include $GABA_B$ receptor- and receptor protein-specific nucleic acids in ordinarily $GABA_B$ receptor- or receptor protein-expressing cells, where the nucleic acids are in a chromosomal location different from that of natural cells or are otherwise flanked by different DNA sequences than those found in nature.

In accordance with the present invention, there are provided isolated nucleic acids, e.g. DNAs or RNAs, encoding $GABA_B$ receptors and $GABA_B$ receptor proteins, particularly mammalian $GABA_B$ receptors and receptor proteins, such as e.g. human and rat $GABA_B$ receptors and receptor proteins, or fragments thereof. In particular, the invention provides DNA molecules encoding human and rat $GABA_B$ receptors or receptor proteins, or fragments thereof. By definition, such a DNA comprises a coding single stranded DNA, a double stranded DNA consisting of said coding DNA and complementary DNA thereto, or this complementary (single stranded) DNA itself. Exemplary nucleic acids encoding $GABA_B$ receptors and $GABA_B$ receptor proteins are represented in SEQ ID Nos. 1, 7, and 3, 5, respectively.

The preferred sequences encoding $GABA_B$ receptors and receptor proteins are those having substantially the same nucleotide sequence as the coding sequences in SEQ ID Nos. 1, 3, 5 and 7, with the nucleic acids having the same sequence as the coding sequences in SEQ ID Nos. 1, 3, 5 and 7 being most preferred. As used herein, nucleotide sequences which are substantially the same share at least about 90% identity. However, in the case of splice variants having e.g. an additional exon sequence homology may be lower.

The nucleic acids of the invention, whether used as probes or otherwise, are preferably substantially homologous to the sequences encoding the $GABA_B$ receptors or receptor proteins as shown in SEQ ID No. 1, 3, 5 and 7. The terms "substantially" and "homologous" are used as hereinbefore defined with reference to the $GABA_B$ receptor polypeptides.

Preferably, nucleic acids according to the invention are fragments of the $GABA_B$ receptor- or receptor protein-encoding sequences, or derivatives thereof as hereinbefore defined in relation to polypeptides. Fragments of the nucleic acid sequences of a few nucleotides in length, preferably 5 to 150 nucleotides in length, are especially useful as probes.

Exemplary nucleic acids can alternatively be characterised as those nucleotide sequences which encode a $GABA_B$ receptor or receptor protein as hereinbefore defined and hybridise to the DNA sequences set forth in SEQ ID Nos. 1, 3, 5 and/or 7, or a selected fragment of said DNA sequences. Preferred are such sequences encoding $GABA_B$ receptors or receptor proteins which hybridise under high-stringency conditions to the sequences of SEQ ID Nos. 1, 3, 5 and/or 7.

Stringency of hybridisation refers to conditions under which polynucleic acids hybrids are stable. Such conditions are evident to those of ordinary skill in the field. As known to those of skill in the art, the stability of hybrids is reflected in the melting temperature ($T_m$) of the hybrid which decreases approximately by 1 to 1.5° C. with every 1% decrease in sequence homology. In general, the stability of a hybrid is a function of sodium ion concentration and temperature. Typically, the hybridisation reaction is performed under conditions of higher stringency, followed by washes of varying stringency.

As used herein, high stringency refers to conditions that permit hybridisation of only those nucleic acid sequences that form stable hybrids in 1 M $Na^+$ at 65–68° C. High stringency conditions can be provided, for example, by hybridisation in an aqueous solution containing 6×SSC, 5×Denhardt's, 1% SDS (sodium dodecyl sulphate), 0.1 sodium pyrophosphate and 0.1 mg/ml denatured salmon sperm DNA as non specific competitor. Following hybridisation, high stringency washing may be done in several steps, with a final wash (about 30 min) at the hybridisation temperature in 0.2 –0.1×SSC, 0.1% SDS.

Moderate stringency refers to conditions equivalent to hybridisation in the above described solution but at about 60–62° C. In that case the final wash is performed at the hybridisation temperature in 1×SSC, 0.1% SDS.

Low stringency refers to conditions equivalent to hybridisation in the above described solution at about 50–52° C. In that case, the final wash is performed at the hybridisation temperature in 2×SSC, 0.1% SDS.

It is understood that these conditions may be adapted and duplicated using a variety of buffers, e.g. formamide-based buffers, and temperatures. Denhardt's solution and SSC are well known to those of skill in the art as are other suitable hybridisation buffers (see, e.g. Sambrook, et al., eds. (1989) Molecular Cloning: A Laboratory Manual, Cold Spring Harbor Laboratory Press, New York or Ausubel, et al., eds. (1990) Current Protocols in Molecular Biology, John Wiley & Sons, Inc.). In particular, the skilled person will understand that the stringency of hybridisation conditions may be varied by altering a number of parameters, primarily the salt concentration and the temperature, and that the conditions obtained are a result of the combined effect of all such parameters. Optimal hybridisation conditions have to be determined empirically, as the length and the GC content of the probe also play a role.

Nucleic acids according to the invention may moreover be designed to have quite different sequences from those of nucleic acids encoding $GABA_B$ receptors or receptor proteins as derived from natural sources, through exploitation of the degeneracy of the amino acid code. In most cases, a plurality of nucleotide triplets may be used to encode a given amino acid. Thus, an almost limitless number of nucleic acids which encode identical $GABA_B$ receptors or receptor proteins may be designed. Those which most differ from the sequence of the naturally occurring nucleic acid may be so different as to be unable to hybridise therewith. The invention thus specifically encompasses any nucleic acid which encodes a $GABA_B$ receptor or $GABA_B$ receptor protein as hereinbefore defined. Preferred are all nucleic acids which encode the sequences of the $GABA_B$ receptors and receptor proteins set forth in SEQ ID Nos. 2, 8, and 4, 6, respectively.

Given the guidance provided herein, the nucleic acids of the invention are obtainable according to methods well known in the art. For example, a DNA of the invention is obtainable by chemical synthesis, using polymerase chain reaction (PCR) or by screening a genomic library or a suitable cDNA library prepared from a source believed to possess $GABA_B$ receptor or receptor protein and to express it at a detectable level.

Chemical methods for synthesis of a nucleic acid of interest are known in the art and include triester, phosphite, phosphoramidite and H-phosphonate methods, PCR and other autoprimer methods as well as oligonucleotide synthesis on solid supports. These methods may be used if the entire nucleic acid sequence of the nucleic acid is known, or the sequence of the nucleic acid complementary to the coding strand is available. Alternatively, if the target amino acid sequence is known, one may infer potential nucleic acid sequences using known and preferred coding residues for each amino acid residue.

An alternative means to isolate a gene encoding $GABA_B$ receptor or receptor protein is to use PCR technology as described e.g. in section 14 of Sambrook et al., 1989. This method requires the use of oligonucleotide probes that will hybridise to a $GABA_B$ receptor- or receptor protein-specific nucleic acid.

A nucleic acid encoding a $GABA_B$ receptor or receptor protein can be isolated by screening suitable cDNA or genomic libraries under suitable hybridisation conditions with a probe, i.e. a nucleic acid disclosed herein including oligonucleotides derivable from the sequences set forth in SEQ ID Nos. 1, 3, 5 and 7. Suitable libraries are commercially available or can be prepared e.g. from cell lines, tissue samples, and the like. Libraries are screened with probes or analytical tools designed to identify the gene of interest or the protein encoded by it. For cDNA expression libraries suitable means include monoclonal or polyclonal antibodies that recognise and specifically bind to the $GABA_B$ receptor or $GABA_B$ receptor protein; oligonucleotides of about 20 to 80 bases in length that encode known or suspected $GABA_B$ receptor- or receptor protein-specific cDNA from the same or different species; and/or complementary or homologous cDNAs or fragments thereof that encode the same or a hybridising gene. Appropriate probes for screening genomic DNA libraries include, but are not limited to oligonucleotides, cDNAs or fragments thereof that encode the same or hybridising DNA; and/or homologous genomic DNAs or fragments thereof.

Particularly preferred screening techniques include the hybridisation of a test sample of DNA (cDNA or genomic library) with a $GABA_B$ receptor- or receptor protein-specific cDNA (SEQ ID Nos. 1, 3, 5, 7) under suitable hybridisation conditions. Either the full length or fragments of the $GABA_B$ receptor- or receptor protein-specific cDNA can be used as probes. Such screening is initially carried out under low-stringency conditions. Low stringency conditions are as hereinbefore defined, but may be varied by adjusting the temperature and ionic strength of the hybridisation solution. For example, suitable conditions comprise hybridisation at a temperature between 40° C. and 60° C. in 0.5M $NaH_2PO_4$ pH 7.2, 7% sodium dodecyl sulphate (SDS), 1% bovine serum albumin, 1 mM EDTA, with a washing step at 50° C. or less in 2×standard saline citrate (SSC, 20×SSC contains 3M sodium chloride, 0.3M sodium citrate, pH 7.0), 0.1% SDS. Preferably, hybridisation conditions will be selected which allow the identification of nucleotide sequences having at least 40% sequence homology with respect to the probe. Similar homology screening techniques useful for the identification and isolation of additional cDNAs and genes of the GABA$_B$-receptor gene family are described in U.S. Pat. No. 5,202,257, incorporated herein by reference.

After low stringency hybridisation has been used to identify cDNA or genomic clones having a substantial similarity with the probe sequence, these clones are then subjected to moderate to high stringency conditions in order to identify those clones having particularly high level of homology with respect to the probe sequence. Further examples of high stringency conditions comprise a hybridisation temperature of about 60° C. to 68° C. using the above mentioned hybridisation solution. Washing conditions comprise 0.5×SSC, 0.1% SDS or less at a temperature of about 65° C. or less.

In view of the identification of GABA$_B$ receptor- and receptor protein-specific cDNAs according to the invention, the compiled sequence information can be used to design a set of degenerate oligonucleotide primer sequences from the regions most conserved among members of the gene family. A mixture of such oligonucleotide primers can be used in the polymerase chain reaction (PCR) to amplify cDNAs or genomic segments from genes related to the already isolated GABA$_B$ receptor- and receptor protein-specific cDNAs.

Subsequently, these segments can serve as probes for identifying further full-length cDNA clones using high stringency hybridisation conditions. Alternatively, antibodies derived against the GABA$_B$ receptors or GABA$_B$ receptor protein provided by the present invention can be used to purify and sequence related GABA$_B$ receptors and receptor proteins also recognised by the antibodies.

Screening of libraries in order to isolate nucleic acids according to the invention may moreover be performed by expression screening. Such methodology is known to those skilled in the art, for example as set out in Sambrook et al. (Op. Cit.), but essentially comprises the incorporation of nucleic acid clones into expression vectors which are then screened using a ligand specific for the desired protein product. GABA$_B$ receptor- or receptor protein-specific ligands may be antibodies, as described hereinbelow, or specific GABA antagonists or agonists. Especially preferred are compounds such as CGP 64213, described hereinbelow.

As used herein, an oligonucleotide probe is preferably a single-stranded DNA or RNA that has a sequence of nucleotides that includes between 10 and 50, preferably between 15 and 30 and most preferably at least about 20 contiguous bases that are the same as (or the complement of) an equivalent or greater number of contiguous bases as set forth in SEQ ID Nos. 1, 3, 5 and 7. The nucleic acid sequences selected as probes should be of sufficient length and sufficiently unambiguous so that false positive results are minimised. The nucleotide sequences are usually based on conserved or highly homologous nucleotide sequences or regions of the GABA$_B$ receptor or receptor protein. The nucleic acids used as probes may be degenerate at one or more positions. The use of degenerate oligonucleotides may be of particular importance where a library is screened from a species in which preferential codon usage in that species is not known.

Preferred regions from which to construct probes include 5' and/or 3' coding sequences, sequences predicted to encode ligand binding sites, and the like. For example, either the full-length cDNA clones disclosed herein or fragments thereof can be used as probes. Preferably, nucleic acid probes of the invention are labelled with suitable label means for ready detection upon hybridisation. For example, a suitable label means is a radiolabel. The preferred method of labelling a DNA fragment is by incorporating $\alpha^{32}$P dATP with the Klenow fragment of DNA polymerase in a random priming reaction, as is well known in the art. Oligonucleotides are usually end-labelled with $\gamma^{32}$P-labelled ATP and polynucleotide kinase. However, other methods (e.g. non-radioactive) may also be used to label the fragment or oligonucleotide, including e.g. enzyme labelling, fluorescent labelling with suitable fluorophores and biotinylation.

After screening the library, for example with a portion of DNA including substantially the entire GABA$_B$ receptor- or receptor protein-encoding sequence or a suitable oligonucleotide based on a portion of said DNA, positive clones are identified by detecting a hybridisation signal; the identified clones are characterised by restriction enzyme mapping and/or DNA sequence analysis, and then examined, for example by comparison with the sequences set forth herein, to ascertain whether they include DNA encoding a complete GABA$_B$ receptor or receptor protein (i.e., if they include translation initiation and termination codons). If the selected clones are incomplete, they may be used to rescreen the same or a different library to obtain overlapping clones. If the library is genomic, then the overlapping clones may include exons and introns. If the library is a cDNA library, then the overlapping clones will include an open reading frame. In both instances, complete clones may be identified by comparison with the DNAs and deduced amino acid sequences provided herein.

In order to detect any abnormality of endogenous GABA$_B$ receptor or receptor protein, genetic screening may be carried out using the nucleotide sequences of the invention as hybridisation probes. Also, based on the nucleic acid sequences provided herein antisense-type therapeutic agents may be designed. In particular reference thereto, it is to be noted that antisense oligonucleotides are based on oligonucleotide probes as hereinbefore defined, and included within the definition thereof. Such oligonucleotides, especially but not only when intended for use as antisense therapeutic agents, may comprise modifications to the oligonucleotide, for example by incorporation of unnatural nucleotide analogues and modifications to natural oligonucleotides. For example, the oligonucleotides may encompass an altered backbone, for example in the form of a phosphorothioate, modifications such as 2'-O-Methyl modifications, or may be in the form of peptide nucleic acids.

It is envisaged that the nucleic acids of the invention can be readily modified by nucleotide substitution, nucleotide deletion, nucleotide insertion or inversion of a nucleotide stretch, and any combination thereof. Such mutants can be used e.g. to produce a GABA$_B$ receptor or receptor protein mutant that has an amino acid sequence differing from the GABA$_B$ receptor or receptor protein sequences as disclosed herein or as found in nature. Mutagenesis may be predetermined (site-specific) or random. A mutation which is not a silent mutation must not place sequences out of reading frames and preferably will not create complementary regions that could hybridise to produce secondary mRNA structure such as loops or hairpins.

In still another aspect of the invention, the nucleic acids are DNA molecules and further comprise a replicable vector comprising the nucleic acid encoding the GABA$_B$ receptor or receptor protein operably linked to control sequences recognised by a host transformed by the vector. As used herein, vector (or plasmid) refers to discrete elements that are used to introduce heterologous DNA into cells for either expression or replication thereof. Selection and use of such vehicles is a routine matter for the person of ordinary skill in the art and is described, for example, in Sambrook et at., (1989) Molecular Cloning: A Laboratory Manual, Second Edition, Cold Spring Harbor Laboratory Press. Many vectors are available, and selection of appropriate vector will depend on the intended use of the vector, i.e. whether it is to be used for DNA amplification or for DNA expression, the size of the DNA to be inserted into the vector, and the host cell to be transformed with the vector. Each vector contains various components depending on its function (amplification of DNA or expression of DNA) and the host cell for which it is compatible. The vector components generally include, but are not limited to, one or more of the following: an origin of replication, one or more marker genes, an enhancer element, a promoter, a transcription termination sequence and a signal sequence.

Advantageously, a eukaryotic expression vector encoding a $GABA_B$ receptor or receptor protein will comprise a locus control region (LCR). LCRs are capable of directing high-level integration site independent expression of transgenes integrated into host cell chromatin, which is of importance especially where the $GABA_B$ receptor or receptor protein gene is to be expressed in the context of a permanently-transfected eukaryotic cell line in which chromosomal integration of the vector has occurred, in vectors designed for gene therapy applications or in transgenic animals.

Suitable vectors for expression in eukaryotic host cells, including yeast, fungi, insect, plant, animal, human, or nucleated cells from other multicellular organisms, will also contain sequences necessary for the termination of transcription and for stabilising the mRNA. Such sequences are commonly available from the 5' and 3' untranslated regions of eukaryotic or viral DNAs or cDNAs.

Furthermore the invention provides host cells transformed with such a vector and a method of using a nucleic acid encoding a $GABA_B$ receptor or receptor protein according to the invention to produce such a $GABA_B$ receptor or receptor protein, comprising expressing a $GABA_B$ receptor- or receptor protein-specific nucleic acid in a culture of the transformed host cells and, if desired, recovering the $GABA_B$ receptor or receptor protein from the host cell culture. In accordance with another embodiment of the present invention, there are provided cells containing the above-described nucleic acids. Such host cells such as prokaryote, yeast and higher eukaryote cells may be used for replicating DNA and producing $GABA_B$ receptor or receptor protein. Suitable prokaryotes include eubacteria, such as Gram-negative or Gram-positive organisms, such as E. coli, e.g. E. coli K-12 strains DH5a, MC1061/P3 and HB101, or Bacilli. Further hosts suitable for $GABA_B$ receptor protein encoding vectors include eukaryotic microbes such as filamentous fungi or yeast, e.g. Saccharomyces cerevisiae. Higher eukaryotic cells include insect and vertebrate cells, particularly mammalian cells. In recent years propagation of vertebrate cells in culture (tissue culture) has become a routine procedure. Examples of useful mammalian host cell lines are epithelial or fibroblastic cell lines such as Chinese hamster ovary (CHO) cells, COS cells, NIH 3T3 cells, HeLa cells or HEK293 cells. The host cells referred to in this disclosure comprise cells in in vitro culture as well as cells that are within a host animal.

DNA may be stably incorporated into cells or may be transiently expressed using methods known in the art, such as those detailed in Sambrook et al., Op. Cit., or Ausubel et al, (1990) Current Protocols in Molecular Biology, John Wiley & Sons, Inc.

The polypeptides according to the invention can advantageously be expressed in insect cell systems, including whole insects. Insect cell lines suitable for use in the method of the invention include, in principle, any lepidopteran cell which is capable of being transformed with an expression vector and expressing heterologous proteins encoded thereby. In particular, use of the Sf cell lines, such as the *Spodoptera frugiperda* cell line IPBL-SF-21 AE (Vaughn et al., (1977) In Vitro, 13, 213–217) is preferred. The derivative cell line Sf9 is particularly preferred. However, other cell lines, such as Tricoplusia ni368 (Kurstack and Marmorosch, (1976) Invertebrate Tissue Culture Applications in Medicine, Biology and Agriculture. Academic Press, New York, USA) may be employed. These cell lines, as well as other insect cell lines suitable for use in the invention, are commercially available (e.g. from Stratagene, La Jolla, Calif., USA).

Expression vectors suitable for use in the invention include all vectors which are capable of expressing foreign proteins in insect cell lines. In general, vectors which are useful in mammalian and other eukaryotic cells are also applicable to insect cell culture. Baculovirus vectors, specifically intended for insect cell culture, are especially preferred and are widely obtainable commercially (e.g. from Invitrogen and Clontech). Other virus vectors capable of infecting insect cells are known, such as Sindbis virus (Hahn et al., (1992) PNAS (USA) 89, 2679–2683). The baculovirus vector of choice (reviewed by Miller (1988) Ann. Rev. Microbiol. 42, 177–199) is *Autographa californica* multiple nuclear polyhedrosis virus, AcMNPV.

Nucleic acids and/or proteins according to the invention may be used in methods for screening compounds of mixtures of compounds which are potential modulators of $GABA_B$ receptors, and thus potential pharmacological agents. For example, cells transformed with a gene encoding a $GABA_B$ receptor or receptor protein can be used in a cell-based screening assay, in which the response of the cell to the agents being tested is monitored. The response may be in the form of the activation of a reporter gene, a measurable pharmacological or electrophysiological change, or the like. Alternatively, purified $GABA_B$ receptors or receptor proteins according to the invention can be used in in vitro assays to screen for modulators of $GABA_B$ receptor activity.

Likewise, compounds which are capable of modulating the expression of the $GABA_B$ receptor genes, thus regulating $GABA_B$ receptor activity, can be screened for using an expression system in which a test gene (which may be one of the $GABA_B$ receptor genes itself) is operably linked to the control sequences normally associated with the $GABA_B$ receptor gene.

The invention moreover includes compounds identified by such screening assays and the use of such compounds for the treatment of conditions which are susceptible to treatment by $GABA_B$ receptor modulation as exemplified hereinbefore.

In accordance with yet another embodiment of the present invention, there are provided antibodies specifically recognising and binding to one or more of the $GABA_B$ receptors or receptor proteins of the invention. For example, such antibodies can be generated against the $GABA_B$ receptors having the amino acid sequences set forth in SEQ ID Nos. 2 and 8. Alternatively, $GABA_B$ receptor proteins as set forth in SEQ ID Nos. 4 and 6 or $GABA_B$ receptor protein fragments (which may also be synthesised by in vitro methods) are fused (by recombinant expression or an in vitro peptidyl bond) to an immunogenic polypeptide and this fusion polypeptide, in turn, is used to raise antibodies against a $GABA_B$ receptor protein epitope.

Anti-$GABA_B$ receptor or receptor protein antibodies may be recovered from the serum of immunised animals. Monoclonal antibodies may be prepared from cells from immunised animals in the conventional manner.

The antibodies of the invention are useful for studying GABA$_B$ receptor protein localisation, screening of an expression library to identify nucleic acids encoding GABA$_B$ receptors or receptor proteins or the structure of functional domains, as well as for the purification of GABA$_B$ receptors or receptor proteins, and the like.

Antibodies according to the invention may be whole antibodies of natural classes, such as IgE and IgM antibodies, but are preferably IgG antibodies. Moreover, the invention includes antibody fragments, such as Fab, F(ab')$_2$, Fv and ScFv. Small fragments, such Fv and ScFv, possess advantageous properties for diagnostic and therapeutic applications on account of their small size and consequent superior tissue distribution.

The antibodies according to the invention may be used in diagnostic and therapeutic applications. Accordingly, they may be altered antibodies comprising an effector protein such as a toxin or a label. Especially preferred are labels which allow the imaging of the distribution of the antibody in vivo. Such labels may be radioactive labels or radioopaque labels, such as metal particles, which are readily visualisable within an organism. Moreover, they may be fluorescent labels or other labels which are visualisable on tissue samples removed from organisms.

Recombinant DNA technology may be used to improve the antibodies of the invention. Thus, chimeric antibodies may be constructed in order to decrease the immunogenicity thereof in diagnostic or therapeutic applications. Moreover, immunogenicity may be minimised by humanising the antibodies by CDR grafting [see European Patent Application 0 239 400 (Winter)] and, optionally, framework modification [see EP 0 239 400 and Riechmann et al., Nature 332, 323–327, 1988].

Antibodies according to the invention may be obtained from animal serum, or, in the case of monoclonal antibodies or fragments thereof, produced in cell culture. Recombinant DNA technology may be used to produce the antibodies according to established procedure, in bacterial or preferably mammalian cell culture. The selected cell culture system preferably secretes the antibody product.

Therefore, the present invention includes a process for the production of an antibody according to the invention comprising culturing a host, e.g. *E coli* or a mammalian cell, which has been transformed with a hybrid vector comprising an expression cassette comprising a promoter operably linked to a first DNA sequence encoding a signal peptide linked in the proper reading frame to a second DNA sequence encoding said protein, and isolating said protein.

The invention further concerns hybridoma cells secreting the monoclonal antibodies of the invention. The preferred hybridoma cells of the invention are genetically stable, secrete monoclonal antibodies of the invention of the desired specificity and can be activated from deep-frozen cultures by thawing and recloning.

The invention also concerns a process for the preparation of a hybridoma cell line secreting monoclonal antibodies directed to a GABA$_B$ receptor or receptor protein, characterised in that a suitable mammal, for example a Balb/c mouse, is immunised with purified GABA$_B$ receptor or receptor protein, an antigenic carrier containing purified GABA$_B$ receptor or receptor protein or with cells bearing GABA$_B$ receptor or receptor protein, antibody-producing cells of the immunised mammal are fused with cells of a suitable myeloma cell line, the hybrid cells obtained in the fusion are cloned, and cell clones secreting the desired antibodies are selected. For example spleen cells of Balb/c mice immunised with cells bearing GABA$_B$ receptor or receptor protein are fused with cells of the myeloma cell line PAI or the myeloma cell line Sp2/0-Ag14, the obtained hybrid cells are screened for secretion of the desired antibodies, and positive hybridoma cells are cloned.

The invention also concerns recombinant DNAs comprising an insert coding for a heavy chain variable domain and/or for a light chain variable domain of antibodies directed to the extracellular domain of GABA$_B$ receptor or receptor protein as described hereinbefore. By definition such DNAs comprise coding single stranded DNAs, double stranded DNAs consisting of said coding DNAs and of complementary DNAs thereto, or these complementary (single stranded) DNAs themselves.

The invention also provides a transgenic non-human mammal which has been modified to modulate the expression of endogenous GABA$_B$ receptor or receptor protein. Preferably, the transgenic non-human mammal is a transgenic mouse. For example, therefore, a transgenic mouse may be designed in which GABA$_B$ receptor or receptor protein production is greatly reduced or eliminated, according to procedures established in the art (Mansour et al., Nature 336, 348–352, 1988). Alternatively, the transgenic mouse of the invention may express elevated levels of GABA$_B$ receptor or receptor protein, or may be subject to regulation of GABA$_B$ receptor or receptor protein expression in a developmentally or tissue-specific manner, or via control by exogenous agents. Study of such an animal provides insights into the importance of the GABA$_B$ receptors and receptor proteins in vivo.

The invention is further described hereinbelow, for the purposes of illustration only, in the following Examples.

EXAMPLE 1

Synthesis of Ligand CGP64213

The radioligand [$^{125}$I]CGP 64213, which is used to visualise GABA$_B$ receptors expressed in COS cells, is synthesised according to Scheme 1, using the following reagents and conditions:

(1) NaH, THF, rt, 3 h; 5-bromovaleronitrile, rt, 16 h; (2) Raney nickel, 4% NH$_3$ in EtOH, 45° C., 16 h; (3) N-ethoxycarbonylphtalimide, Na$_2$CO$_3$, H$_2$O, CH$_2$Cl$_2$, rt, 5 h; (4) Me$_3$SiCl, EtOH CH$_2$Cl$_2$ (1:9), rt, 17 h; (5) Me$_3$SiCl, Et$_3$N, THF, rt, 17 h; (R)-epichlorohydrin, 10 mol % ZnCl$_2$ THF, 80° C., 17 h; HOAC, MeOH, rt, 17 h; (6) i-Pr$_2$EtN, EtOH, 80° C., 7 d; (7) LiOH, EtOH, H$_2$O (1:1), 100° C., 17 h; MeOH, H$_3$PO$_4$; (8) conc. HCl, 100° C., 17 h; (9) i-Pr$_2$EtN, DMF, rt, 72 h; (10) Na$^{125}$I, phosphate buffer pH 7.4, H$_2$O$_2$, cat. lactoperoxidase, 30 min, RP-HPLC.

Ethyl (1,1-diethoxyethyl)phosphinate 1, prepared according to Froestl, W., et al. *J. Med. Chem.*(1995), 38, 3297–3312, from phosphinic acid and triethylorthoacetate under catalysed by boron trifluoride diethyl etherate, is condensed with 5-bromovaleronitrile to give the oily cyanoderivative 2 (bp 164° C. at 0.13 mbar), which is hydrogenated over Raney nickel in ethanol containing 4% of ammonia to give primary amine 3 (bp 150–160° C. at 10$^{-4}$ mbar; Kugelrohr bath temperature). The amino-group in 3 is protected as pthalimide to give 4, which is now deprotected at the phosphinic acid moiety under very mild conditions to give monosubstituted phosphinic acid ester 5. On reaction with trimethylchlorosilane the penta-valent phosphinate ester 5 is converted into a very reactive silyated phosphonite, which reacts readily with (R)-epichlorohydrin under zinc chloride catalysis to produce chlorohydrin 7. Condensation with 1-(R)-(+)-(3-cyanophenyl)-ethylamine 8, which itself is prepared via resolution of racemic (3-cyano-phenyl)-ethylamine with N-acetly-L-leucine to separate 1-(S)-(+)-(3-cyanophenyl)-ethylamine (according to Pickard et al., *J. Amer. Chem. Soc.*(1990) 112, 5741–5747) and treatment of the remaining mother liquors with (–)-camphanic acid followed by three crystallisations, gives the aromatic nitrile-ester 9, which is hydrolysed to the meta-benzoic acid derivative 10 with lithium hydroxide. Concomitant hydrolysis of the ethyl phophinate ester occurs. The pthalimide protecting group is removed by boiling with concentrated hydrochlorid acid overnight to give the key intermediate CGP 57604A([3-[1 -(R)-[[3-(5-aminopentyl)-hydroxyphosphinyl]-2-(S)-hydroxypropyl]amino]-ethyl]-benzoic acid hydrochloride). This is reacted with commercially available N-hydroxysuccinimidyl-3-(4-hydroxyphenyl)-propionate 11 in DMF using Hüjnig's base to give intermediate 12, which is iodinated with sodium iodide (125 isotope) using hydroperoxide and catalytic amounts of lactoperoxidase to give the radioactive ligand [$^{125}$I]CGP 64213.

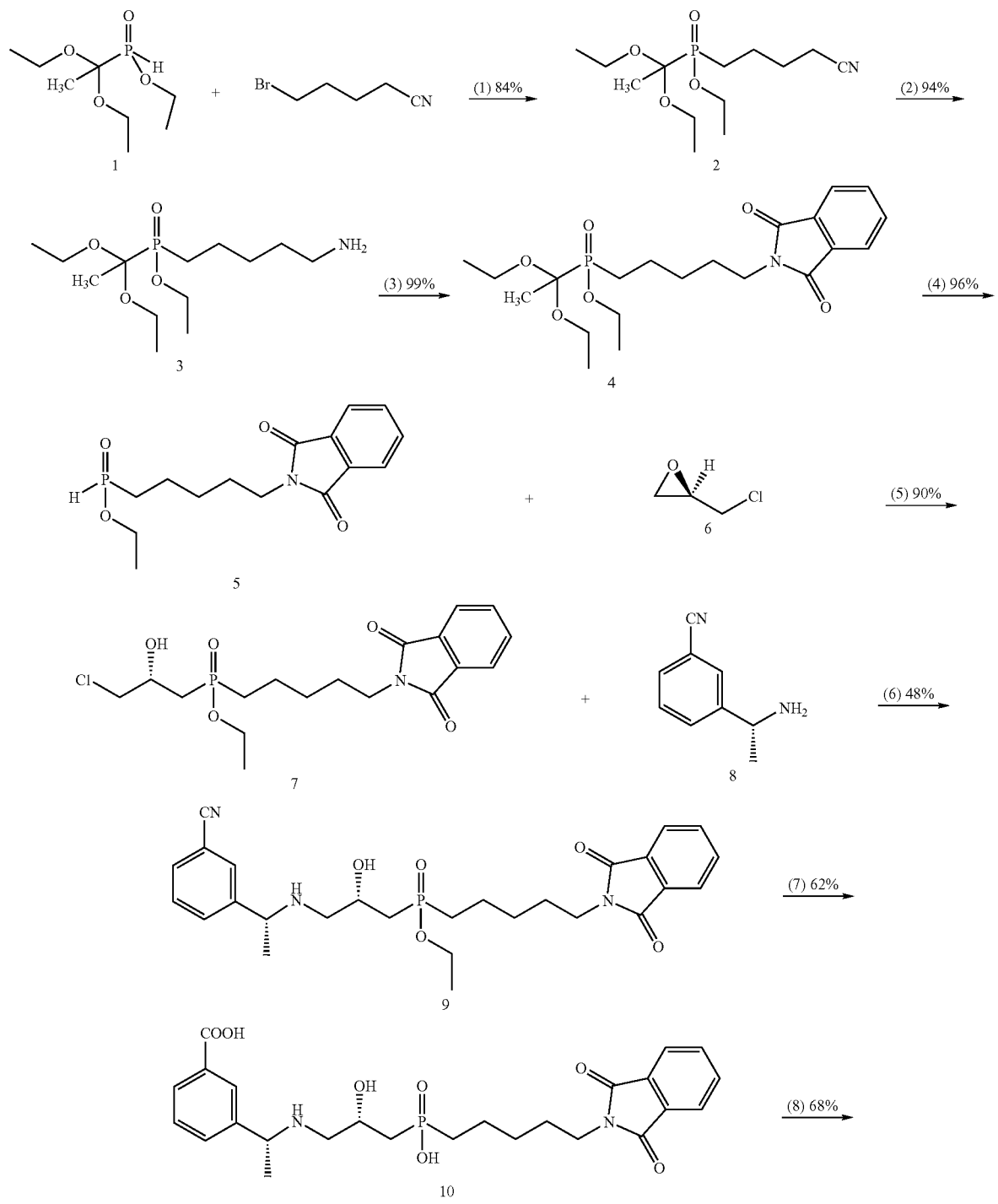

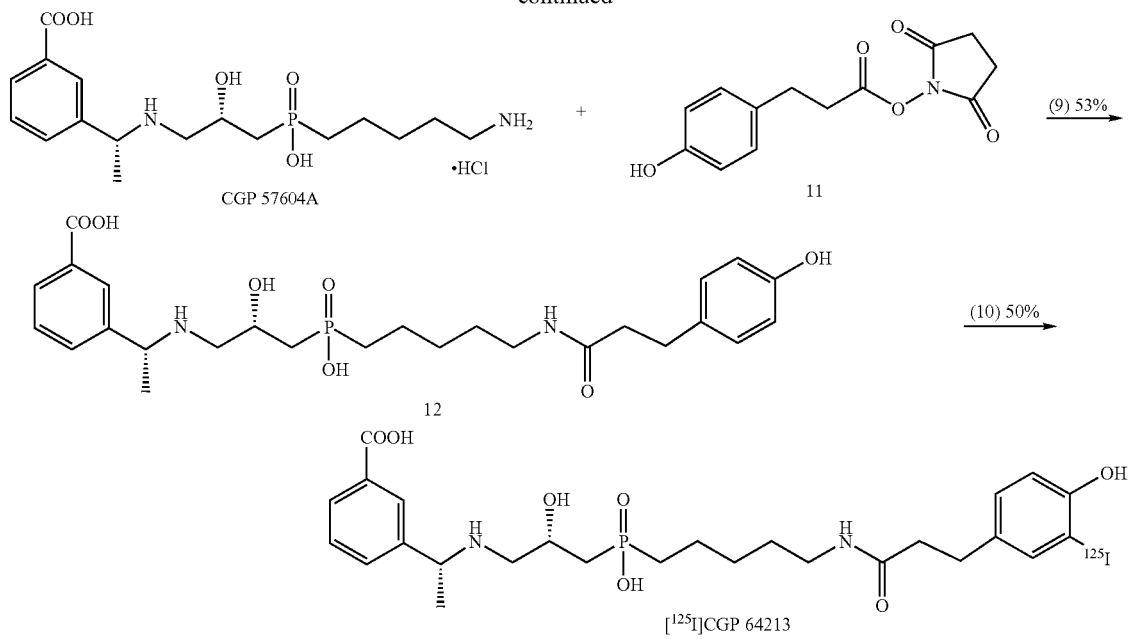

Unlabelled CGP 64213 is prepared in a slightly different way: 3-(4-hydroxy-5-iodophenyl propionic acid 13 is prepared by iodination of 3-(4-hydroxy-phenyl)propionic acid according to Runeberg, J., *Acta Chem. Scand.*(1958), 12,188–91. N-hydroxy-succinimidyl-3(4-hydroxy-5-iodophenyl)propionate 14 (mp: 191–4° C.) is prepared according to Scheme 2 in 73% yield. Condensation of CGP 57604A (Scheme 1) with 14 using Hünig's base in DMF at room temperature for 72 hours proceeded as reaction 9 of Scheme 1 to give non radioactive CGP 64213 (mp: 170–5° C., crystallised from acetone) in a yield of 53%.

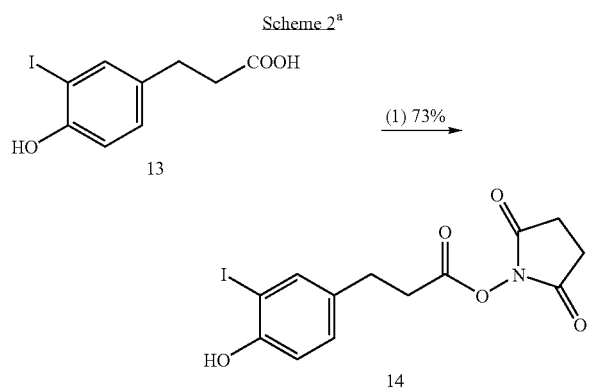

[a]Reagents and conditions: N-hydroxysuccinimide, DCC, dioxane, rt, 16 h.

Characterisation of Radioligand [$^{125}$I]CGP 64213

Preparation of Synaptic Membranes from Rat Cerebral Cortex

Twenty male rats [Tif: RAI f (SPF)] of about 200 g body weight are used. The animals are decapitated, the brains removed, the cerebral cortices dissected and homogenised in 10 volumes of ice-cold 0.32 M sucrose, containing $MgCl_2$ (1 mM) and $K_2HPO_4$ (1 mM), with a glass/Teflon homogeniser. The membranes are centrifuged at 1000×g for 15 min, the pellet resuspended and the centrifugation repeated. The supernatants are pooled and centrifuged at 20000×g for 15 min. The pellet is osmotically shocked by resuspension in 10 volumes $H_2O$ and kept on ice for 30 min. The suspension is centrifuged at 39000×g, resuspended in Krebs-Henseleit buffer (20 mM Tris, pH 7.4, 118 mM NaCl, 5.6 mM glucose, 1.2 mM $KH_2PO_4$, 1.2 mM $MgSO_4$, 4.7 mM KCl, 1.8 mM $CaCl_2$), and kept for 2 days at −20 ° C. The membranes are thawed at room temperature, washed three times with Krebs-Henseleit buffer by centrifugation at 20000×g for 15 min, left overnight at 4° C. and washed again three times. The final pellet is resuspended with a glass/Teflon homogenise in 20 ml of the same buffer. 2 ml aliquots are frozen and stored in liquid nitrogen. Just before use membranes are thawed quickly in a water bath at 37° C. and again washed by centrifugation at 20000×g for 15 min with the same buffer three times.

Binding Assay and Characterisation of Radioligand

Incubation with [$^{125}$I]CGP 64213, specific radioactivity for fresh material 2000 Ci/mmol, is performed in 0.2 ml Krebs-Henseleit-Tris buffer, pH 7.4, at 20° C. for 90 min with 50 μg cortex membrane protein as substrate. The incubation is terminated by filtration through GF/B Whatman glass fibre filters. Nonspecific binding is defined by $10^{-6}$ M CGP 54626A and is 5% of total binding at a concentration of 2 nM. In saturation experiments with increasing concentrations of [$^{125}$I]CGP 64213 and with nonlinear least square fitting a dissociation constant $K_D$ of 2.66 nM is determined. In inhibition studies at a concentration of 0.1 nM [$^{125}$I]CGP 64213, L-baclofen showed an inhibition constant $K_i$ of 442 nM and the antagonist CGP 54626 A a $K_i$ of 2.5 nM in good agreement with $K_i$'s obtained with other $GABA_B$ receptor antagonist radioligands. Unlabelled CGP 64213 is found to be inactive at a concentration of 1 μM in assays for $GABA_A$, benzodiazepine, kainate, AMPA, NMDA receptors, for the strychnine independent binding site at NMDA receptors, muscarinic cholinergic, $\alpha_1$-and $\alpha_2$-adrenergic, $\beta$-adrenergic, $5HT_1$, $5HT_2$, $5HT_3$, histamine$_1$, histamine$_2$, adenosine, μ-opiate and substance P receptors. The compound is therefore selective for GABA$_B$ receptors. At a concentration of 0.1 nM of [$^{125}$I]CGP 64213 association and dissociation kinetics are measured. The halftime of association is 20 min at 20° C. and the halftime of dissociation 40 min. The halftime of dissociation is increased to 4 hours by reduction of the temperature to 4° C. This slow off rate and the high specific radioactivity of [$^{125}$I]CGP 64213 allows autoradiographic studies of receptor binding in COS cells as expression systems for GABA$_B$ receptors.

EXAMPLE 2

Preparation of Photoaffinity Ligand

The photoaffinity ligand [$^{125}$I]CGP 71872, which is used to tag GABA$_B$ receptors from rat cortex membranes and recombinant GABA$_B$ receptors expressed in COS cells is synthesised according to Scheme 3: Commercially available N-hydroxy-succinimidyl-4-azido-salicylate 15 is condensed with CGP 57604A to give intermediate 16, which is iodinated with sodium iodide 125 isotope using chloramine T to give an approximately 1:1 mixture of the 5-iodo derivative [$^{125}$I]CGP 71872 and the 3-iodo-derivative [$^{125}$I]CGP 72565. They are separated via reverse phase HPLC on a Vydac 218TP54 column (retention times: 16.4 and 17.4 minutes, respectively). Reagents and conditions are as follows:

(1) CGP 57604A (Scheme 1), i-Pr$_2$EtN, DMF, rt, 70 h; (2) Na$^{125}$I, chloramine T, 0.01 N NaOH, rt, 1 h; RP-HPLC.

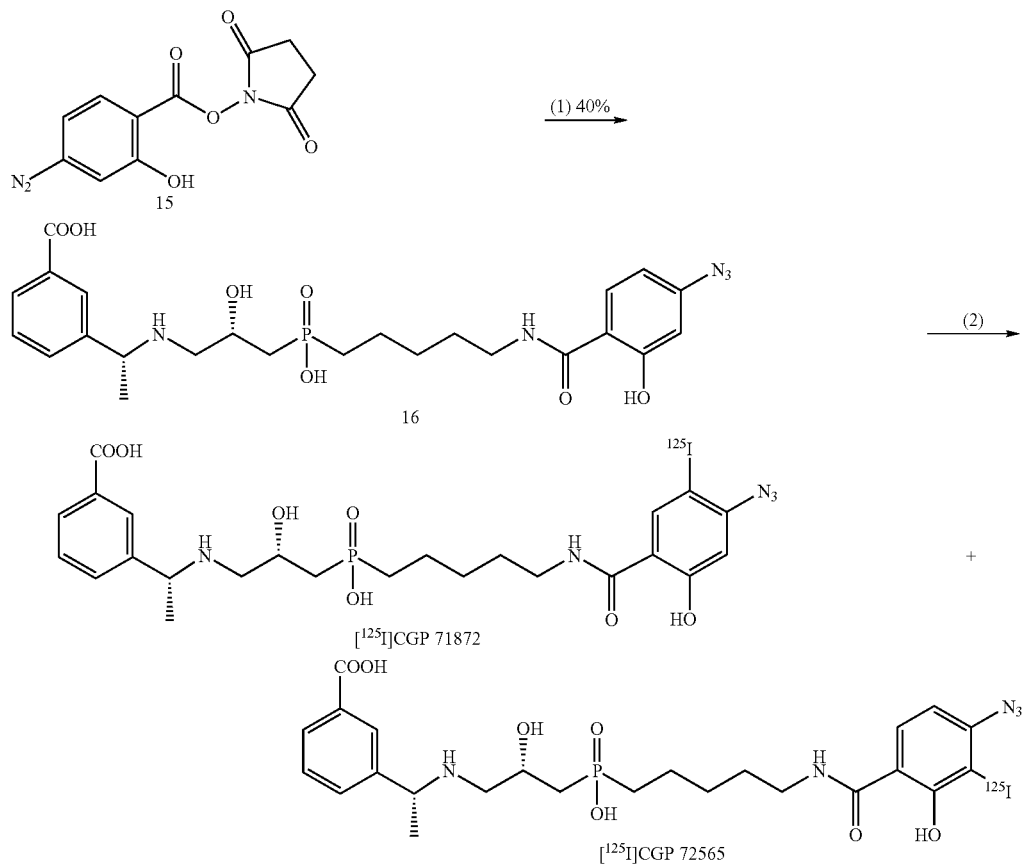

Scheme 3

Unlabelled CGP 71872 is prepared in a different way: N-hydroxy-succinimidyl-4-azido-5-iodo-salicylate 17 is prepared via iodination of 4-azidosalicylic acid and subsequent condensation with N-hydroxy-succinimide (Scheme 4). Condensation of 17 with CGP 57604A (see Scheme 1, reaction 9) proceeded in 57% yield to give non radioactive CGP 71872 (mp:>190° C. dec.).

Reagents and conditions as follows: (1) (1) NaI, 2N NaOH, chloramine T, rt, 88 h; (2) N-hydroxysuccinimide, DCC, dioxane, rt, 16 h;

Scheme 4

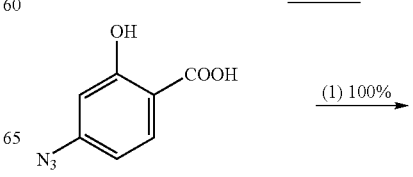

-continued

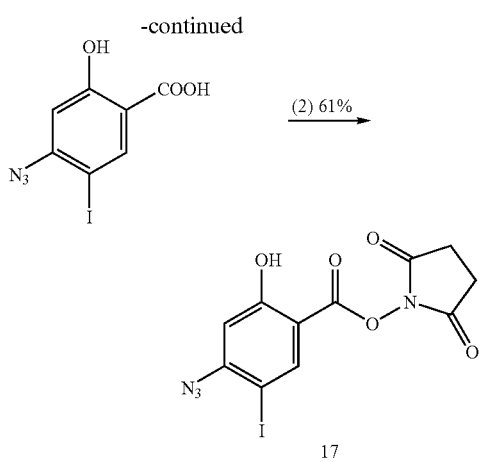

Characterisation of Photoaffinity Ligand [$^{125}$I]CGP 71872

Binding Assay and Characterisation of Ligand

Rat cortex membranes as described for the [$^{125}$I]CGP 64213 assay are used as substrates. Incubation with [$^{125}$I] CGP 71872, specific radioactivity of fresh material 2000 Ci/mmol, is performed in 0.2 ml Krebs-Henseleit buffer, pH 7.4, at 20° C. for 90 min with 50 µg membrane protein as substrate The incubation is terminated by filtration through GF/C Whatman glass fibre filters. Nonspecific binding is defined by 10$^{-6}$ M CGP 54626 A and is 5% of total binding at a concentration of 2 nM of [$^{125}$I]CGP 71872, In saturation experiments with increasing concentrations of [$^{125}$I]CGP 71872, and nonlinear last square fitting a dissociation constant $K_D$ of 3.1 nM is calculated. L-baclofen showed in inhibition experiments a K of 340 nM and the antagonist CGP 54 626 A showed a $K_i$ of 3.1 nM. Unlabelled CGP 64213 is found to be inactive at a concentration of 1 µM in the same receptor assays as described for [$^{125}$I]CGP 64213 and is, therefore, also selective for GABA$_B$ receptors. At a concentration of 2 nM and at 20° C., the halftime for association is 5 min, the halftime of dissociation 10 min. The dissociation time at 8° C. is much longer. Only 25% of radioligand dissociates after 120 min.

Photoaffinity Labelling of Membranes

Figure 1B:
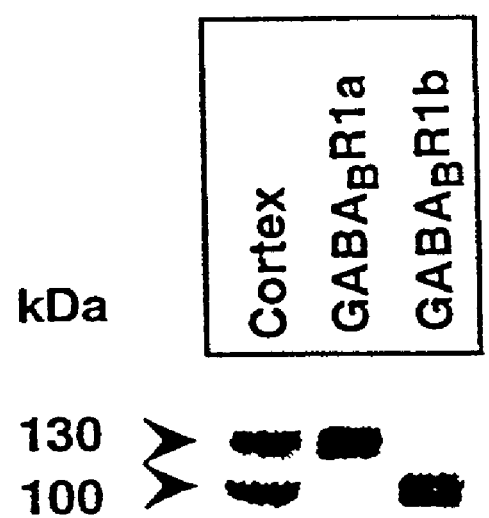
FIG. 1b additionally shows the results for COS1 cells transfected with the $GABA_B$R1b rat-cDNA (lane 3).

Membranes from rat cerebral cortex and from COS1 cells transiently transfected with GABA$_B$R1a and GABA$_B$R1b rat-cDNA, respectively, suspended in Krebs-Henseleit-Tris buffer, pH 7.3, at a concentration of 4 mg protein/ml, are incubated in the dark with 0.6 nM [$^{125}$I] CGP 71872 for one hour at room temperature. The incubation is terminated by centrifugation at 20 000×g for 10 min at 4° C. This step removed free unbound photoaffinity label. Under these conditions about 50% of the total radioactivity used bound to the receptors. The pellet is resuspended at a concentration of 4 mg protein/ml in a polyethylene vial and illuminated with UV light (365 nm) for 3 min (24 W). The suspension is centrifuged at 20 000×g for 10 min and resuspended at a concentration of 8 mg/ml protein in buffer. When the labelling is performed in the presence of excess unlabelled GABA$_B$ receptor antagonist (10$^{-6}$ M CGP 54626A), no radioactivity is bound to the membranes. The labelled membranes could be stored at −80° C. The results are shown in FIGS. 1a and 1b.

Additionally, [$^{125}$I]CGP71872 photoaffinity labelling of cortex, cerebellum and spinal cord cell membranes is analysed as outlined above and reveals that the two GABA$_B$ protein variants R1a and R1b are differentially expressed in the nervous system. In cerebellum the 100K protein is predominant over the 130K protein, whereas in spinal cord the 130K protein is more prevalent. In cortex tissue both proteins appear equally abundant. No proteins are labelled in tissues such as liver and kidney which are expected to lack GABA$_B$ receptors and therefore have been used as controls (see FIG. 4a).

Figure 4:
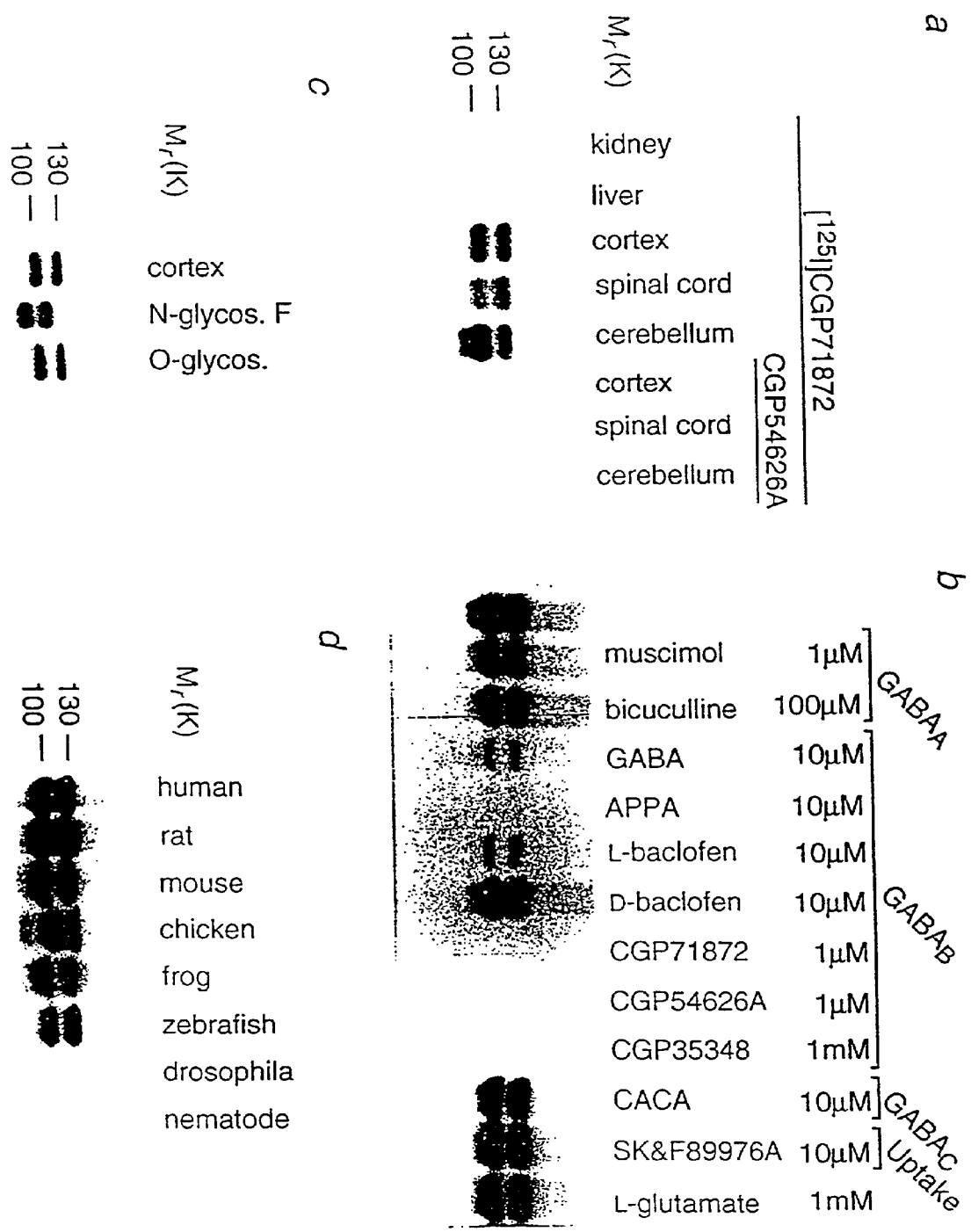
FIG. 4 shows photoaffinity crosslinking of $GABA_B$ receptor proteins. Cell membranes of the tissues indicated are photoaffinity-labelled with [125I]CGP71872 and subjected to SDS-PAGE and autoradiography. a, b, Selectivity of the photoaffinity ligand [125I]CGP71872. a, Differential distribution of $GABA_B$ receptor variants of 130K and 100K in tissues of the nervous system. [125I]CGP71872 binding is inhibited by addition of 1 μM of CGP54626A, a selective $GABA_B$ receptor antagonist. b, Competition of [125I] CGP71872 labelling by different ligands. Incubation of membrane extracts with the photoaffinity ligand is carried out in the presence of competitor substances at the concentrations indicated. c, $GABA_B$ receptors are N-glycosylated. Photoaffinity-labelled rat cortex cell membranes are incubated with 0.4 units N-glycosidase F or 0.6 milliunits O-glycosidase (Boehringer Mannheim). d, Photolabelling of $GABA_B$ receptors from different species. Brain tissues from the species indicated are labelled as described hereinbelow. In the case of Drosophila melanogaster and Haemonchus concortus whole animals are analysed.

Furthermore, native GABA$_B$ receptors are photoaffinity-labelled in the presence of various competitor substances indicated in FIG. 4b. Neither the GABA$_A$ selective ligands muscimol and bicuculline nor the GABA$_C$ receptor agonist cis-aminocrotonic acid (CACA) or the inhibitor of the GABA uptake system, SK&F89976A (Zuiderwijk, M., Veenstra, E., Lopes Da Silva, F. H. & Ghijsen, W. E. J. M. Effects of uptake carrier blockers SK&F89976-A and L-trans-PDC on in vivo release of amino acids in rat hippocampus. Eur. J. Pharmacol. 307, 275–282 (1996)), compete significantly for radioligand binding. In contrast, the GABA$_B$ receptor agonists GABA, APPA (3-aminopropyl-phosphinic acid) and L-baclofen compete with [$^{125}$I] CGP71872 for binding. As another known criterion, L-baclofen competes more potently than D-baclofen. The GABA$_B$ receptor antagonists CGP54626A, CGP35348 and the non-radioactive photoaffinity ligand are also effective displacers of [$^{125}$I]CGP71872 at native receptors. For all ligands tested, there is no visible difference in the displacement of [$^{125}$I]CGP71872 at the 130K and 100K proteins, indicating a qualitatively similar binding pharmacology for the two receptors.

Native GABA$_B$ receptors are N-glycosylated, as shown by the reduction in molecular weight to 110K and 90K, respectively, after cleavage with N-glycosidase F (FIG. 4c). No significant shift in molecular weight is detected after enzymatic treatment with O-glycosidase (FIG. 4c). Photoaffinity-labelled proteins of 130K and 100K are detectable in tissues from all vertebrate species analysed, including zebrafish (FIG. 4d), indicating that the two proteins and their antagonist binding site are highly conserved. The avian GABA$_B$ receptor proteins exhibit molecular weights slightly higher than in other species, possibly reflecting differences in glycosylation and/or RNA splicing. No binding of the photoaffinity ligand to any protein can be detected in the fruitfly Drosophila melanogaster and the nematode Haemonchus concortus.

EXAMPLE 3

Synthesis of the GABA$_B$ Antagonist Ligand CGP 54626A

The ligand used for displacement experiments, CGP 54626A, is synthesised according to Scheme 5:

Scheme 5$^a$

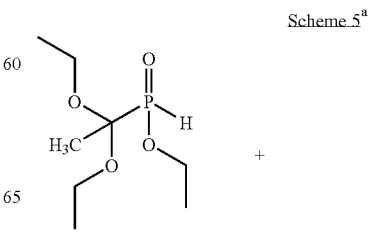

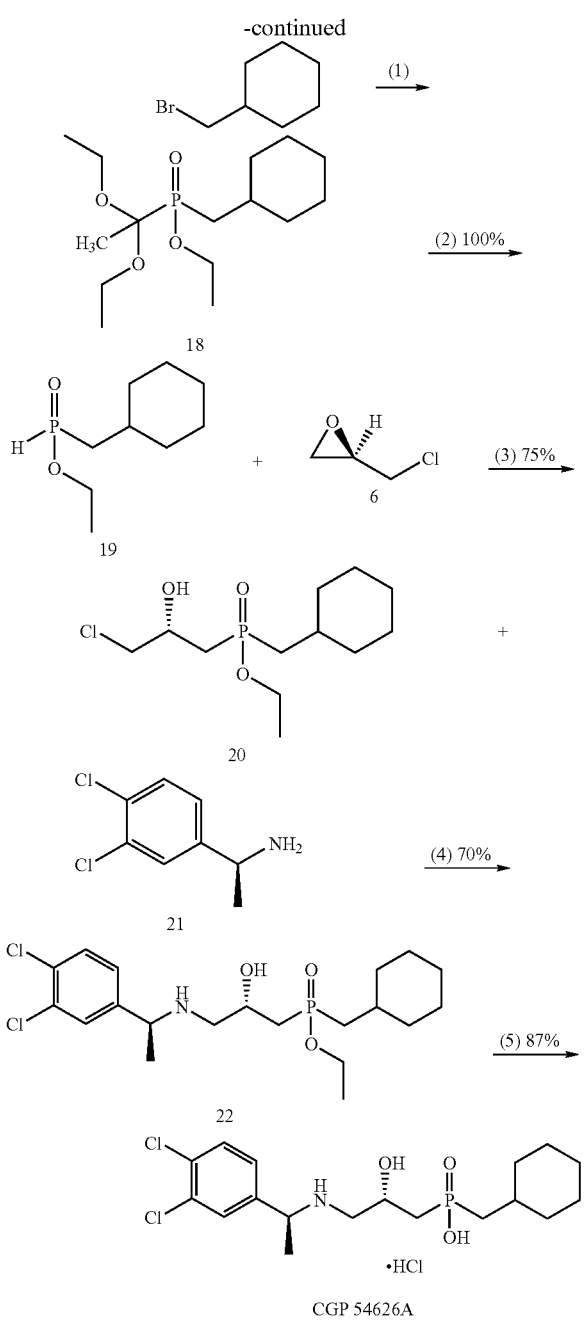

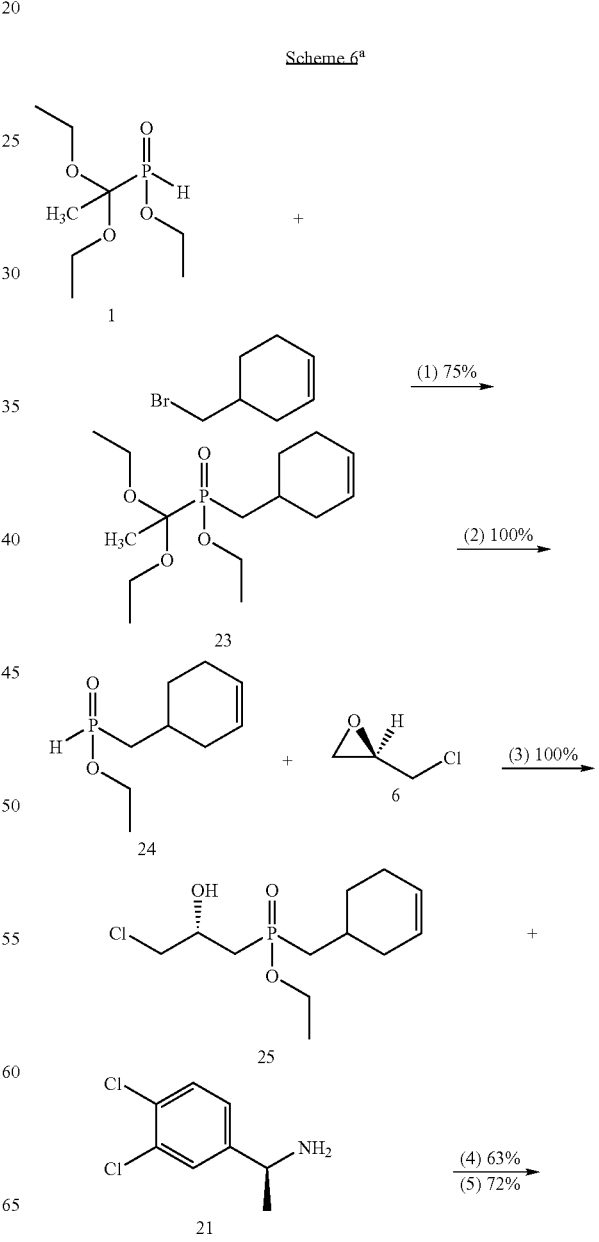

aReagents and conditions: (1) NaH, THF, rt, 3 h; bromomethylcyclohexane, reflux, 24 h; (2) Me₃SiCl, EtOH, CH₂Cl₂ (1:9), rt, 24 h; (3) Me₃SiCl, Et₃N, THF, rt, 24 h; (R)-epichlorohydrin, 10 mol % ZnCl₂ THF, 80° C., 17 h; HOAc, MeOH, rt, 17 h; (4) i-Pr₂EtN, EtOH, 80° C., 7 d; (5) conc. HCl, 100° C., 24 h.

Ethyl (1,1-diethoxyethyl)phosphinate 1, prepared according to Froestl et al., *J. Med. Chem.* (1995), 38, 3297–3312, from phosphinic acid and triethylorthoacetate catalysed by boron trifluoride diethyletherate, is condensed with bromomethylcyclohexane to give the oily derivative 18 (bp 85° C. at 6×10⁻⁴ mbar), which is deprotected at the phosphinic acid moiety under very mild conditions to give monosubstituted phosphinic acid ester 19 (bp 50° C. at 3×10⁻⁴ mbar). On reaction with trimethylchlorosilane the penta-valent phosphinate ester 19 is converted into a very reactive trivalent ethyl phosphonite, which reacted rapidly with (R)-epichlorohydrin 6 when catalysed by zinc chloride to produce chlorohydrin 20. Condensation with 1-(S)-(−)-(3,4-dichlorophenyl)-ethylamine 21, prepared via resolution of racemic 1-(3,4-dichlorophenyl)-ethylamine with (+)-mandelic acid according to Mickel, EP 543780 A2, gave the corresponding secondary amine 22 as a 1:1 mixture of diastereoisomers, which is hydrolysed by boiling with concentrated hydrochloric acid to give CGP 54626A.

[³H]CGP54626A is prepared in an analogous way (Scheme 6) by condensation of ethyl (1,1-diethoxyethyl) phosphinate 1 with 3,4-dehydro-cylohexylmethylbromide (prepared according to Yadav and Fallis, (1991) *Can. J. Chem.* 69, 779–789), preparation of the corresponding 3,4-dehydroderivative of CGP 54626A, i.e. CGP 54951A, which is tritiated under very carefully controlled conditions to yield [³H]CGP54626A. The compound is the first GABA$_B$ receptor antagonist radioligand which was characterised by Bittiger et al., *Pharmacol. Commun.*(1992), 2, 23.

-continued

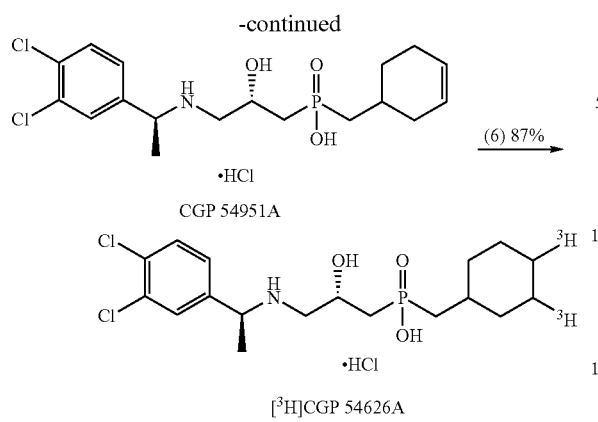

CGP 54951A

[³H]CGP 54626A

<sup>a</sup>Reagents and conditions: (1) NaH, THF, rt, 3 h; 3-4-dehydrobromo-methyl-cyclohexane, reflux, 24 h; (2) Me₃SiCl, EtOH, CH₂Cl₂ (1:9), rt, 24 h; (3) Me₃SiCl, Et₃N, THF, rt, 24 h; (R)-epichlorohydrin, 10 mol % ZnCl₂ THF, 80° C., 17 h; HOAc, MeOH, rt, 17 h; (4) i-Pr₂EtN, EtOH, 80° C., 4 d; (5) LiOH, EtOH, H₂O, 100° C., 17 h; HCl, MeOH, rt, 1 h; (6) ³H₂, 5% Pd/C, HCl, MeOH, pH = 1, rt, 15 min, prep. TLC.

EXAMPLE 4

Proof of Functional Activity of CGP 64213 and CGP 71872 as GABA$_B$ Receptor Antagonists by in Vitro Electrophysiological Measurements Experiments are performed on 400 µm thick hippocampal slices obtained either from female Wistar COB rats (3–4 weeks old) or male rats Tif: RAI f (SPF) using standard techniques. In brief, rats are cervically dislocated prior to decapitation. The brain minus cerebellum is removed rapidly and placed in ice-cold artificial cerebrospinal fluid (ACSF). The hippocampus is carefully isolated and, using either a tissue chopper (Sorvall®) or a vibroslicer (Campden), transverse 400 µm thick slices are cut. The CA3 region of each slice is removed via a scalpel cut. This procedure is performed to eliminate changes in network function that can occur due to epileptiform bursting in area CA3. The resultant CA3-ectomized slices are placed on a nylon mesh at the interface of a warmed (32° C.), perfusing (1–2 ml.min$^{-1}$) ACSF and an oxygen-enriched (95% O₂, 5% CO₂), humidified atmosphere. The standard perfusion medium comprised (mM): NaCl, 124; KCl, 3; NaHCO₃, 26; NaH₂PO₄, 1.25; CaCl₂, 2; MgSO₄, 1; D-glucose, 10; and is bubbled with 95% O₂, 5% CO₂. An Axoprobe or an Axoclamp-2 amplifier (Axon Instruments, Foster City, Calif., USA) is used in bridge mode to make extracellular recordings from either *stratum radiatum* or *stratum oriens* using 4 M NaCl-filled microelectrodes (2–5 MΩ). Intracellular recordings are made using 2 M potassium methylsulphate filled microelectrodes (60–100 MΩ). Digitised records are stored on the hard disk of an IBM-compatible PC for off-line analysis. Bipolar stimulating electrodes, made from 55 µm diameter insulated nickel-chromium wire, are positioned in stratum radiatum close to the recording electrode placed in either *stratum radiatum* or *stratum oriens*, to provide orthodromic monosynaptic activation of CA1 neurones (Davies et al. (1990) *Journal of Physiology* 424: 513). In every experiment stimuli comprise square-wave pulses (20–200 µs; 5–30 V) delivered homosynaptically at a fixed intensity. All drugs are administered via the perfusion medium. Data are presented as means±standard error of the mean (S.E.M.) and statistical significance is assessed using Students t-tests. n values refer to the number of times a particular experiment is performed, each in a different slice taken from a different rat.

GABA$_B$ Autoreceptors

Paired-pulse widening of field EPSPs is used to monitor the effects of CGP 71872 and CGP 64213 on GABA$_B$ autoreceptors. Paired-pulse widening occurs when two stimuli are delivered at 5–10 Hz (interstimulus interval 100–200 ms); a stimulation protocol that does not release sufficient GABA to activate GABA$_B$ heteroreceptors which would, in any case, cause a depression rather than a facilitation of the second field EPSP. This phenomenon is also independent of postsynaptic GABA$_B$ receptors (Nathan et al. (1991) *Exp. Brain Res.* 84(3) 529–537). It is, however, occluded by blocking GABA$_A$ receptor-mediated IPSPs and is inhibited by GABA$_B$ receptor antagonists at concentrations that are required to block GABA$_B$ autoreceptors (Nathan et al (1990), *Brain Research* 531: 55–65). (Note that these concentrations are 3–10 fold higher than those necessary to block postsynaptic GABA$_B$ receptors on both pyramidal neurones and inhibitory interneurones so ruling out an effect at these receptors). Paired-pulse widening of field EPSPs (fEPSPs) is a sensitive measure of GABA$_B$ autoreceptor activity. There is no precedent for any compound being effective in this test system and not in other assays of GABA$_B$ autoreceptor activity e.g., paired-pulse or (–)-baclofen-induced depression of IPSCs.

Paired-pulse stimulation at an interstimulus interval of 200 ms caused a consistent widening of the second EPSP relative to the first EPSP. Thus, the area under the curve of the second fEPSP is 247±17% (in the CGP 64213 series of experiments) and 241±21% (in the CGP 71872 series of experiments) of the first fEPSP, respectively. In the presence of CGP 64213 (0.3 µM; n=5) and CGP 71872 (1 µM; n=3) this paired-pulse widening of EPSPs is abolished indicating the effectiveness of these compounds as antagonists of GABA$_B$ autoreceptors.

GABA$_B$ Heteroreceptors

The effect of CGP 71872 on the depression of field EPSPs induced by bath application of (–)-baclofen is used as an assay for the effect of this compound on GABA$_B$ heteroreceptors located on glutamate afferent terminals. Although, under these conditions, (–)-baclofen will activate other populations of GABA$_B$ receptors (e.g., GABA$_B$ autoreceptors and postsynaptic GABA$_B$ receptors), in addition to GABA$_B$ heteroreceptors, activation of these receptors would tend to increase the size of the field EPSP rather than decrease it. As such, this method is a reasonable measure of activity at GABA$_B$ heteroreceptors. This method provides a more reliable and a quantitatively more repeatable method for activating GABA$_B$ heteroreceptors than that used by Isaacson et al. (1993) *Neuron* 332: 156–158, as it does not rely on physiologically released GABA to activate the heteroreceptors. This latter method is inherently variable due to the different concentrations of synaptically released GABA to which heteroreceptors are exposed in different preparations; a parameter that depends upon the level of GABA released, the distance between the release site and heteroreceptor, and the efficiency of GABA uptake sites. It is important to note, however, that, to date, no discrepancy between the results obtained using these two methods to study GABA$_B$ heteroreceptors has been documented for any compound tested.

(–)-Baclofen (10 µM) had no significant effect on the presynaptic fibre volley of the field EPSP (100±1% of control; P>0.05), recorded in *stratum radiatum*, but depressed the field EPSP slope and peak amplitude by 65±6% and 76±9%, respectively (n=10). Maximum depression is obtained after a 5–10 min perfusion and persisted at this level for the duration of the agonist application. Addition of CGP 71872 (1 µM) to the perfusion medium reversed the depression in every experiment in which it is tested (n=6; P<0.05). Similar results are obtained for field EPSPs recorded in stratum oriens (n=3). In brain slices CGP 71872 had no significant effect on the peak amplitude, slope or presynaptic fibre volley of field EPSPs recorded in stratum radiatum (n=4;P>0.05) or oriens (n =3).

Postsynaptic $GABA_B$ Receptors

The effect of CGP 71872 on the pharmacologically isolated late IPSP is used as a test system to evaluate the effect of CGP 71872 on postsynaptic $GABA_B$ receptors located on CA1 pyramidal neurones. There is a substantial literature (Froestl et al. (1995) Op. Cit.; Jarolimek et al. (1993) *Neurosci. Lett* 154: 31–34; Olpe et al. (1990) *Clin. Neuropharmacol.* 13 Suppl. 2,: 396; McCormick, (1990) *J.Neurophysiol.* 62/5: 1018; Lambert et al, (1989) *Neurosci. Lett.* 107:125–128; Soltesz et al., (1989) *Brain Research* 479: 49–55; Mueller and Misgeld, (1989) *Neurosci. Lett* 102: 229–234; Dutar and Nicoll, (1988) *Nature* 322: 156–8; Karlsson, Pozza and Olpe, (1988) *Eur. J. Pharmacol* 148: 485–486) which indicates that this IPSP is mediated by the synaptic activation of $GABA_B$ receptors. In addition, this method has been used many times in the past and the data generated have always been consistent with that generated for antagonism of (−)-baclofen-induced hyperpolarisations; an approach that has also been adopted as an assay for activity at postsynaptic $GABA_B$ receptors.

The effect of CGP 71872 is tested on a monosynaptically activated $GABA_B$ receptor-mediated late IPSP isolated using a combination of the ionotropic excitatory amino acid antagonists D-2-amino-5-phosphonopentanoate (AP5; 50 µM) and 6-cyano-7-nitroquinoxaline-2,3-dione (CNQX; 20 µM) and the $GABA_A$ receptor antagonist picrotoxin (50 µM). In all neurones tested CGP 71872 (1 µM) abolished the late IPSP (n=6) indicating that this compound is an antagonist of postsynaptic $GABA_B$ receptors.

EXAMPLE 5 cDNA Library Construction

RNA is purified from cortex and cerebellum of 7 day old rats according to Chomczynski, P. & Sacchi, N. (1987) *Anal Biochem.* 162, 156–159. Poly A(+) RNA is enriched by two passages over an oligo (dT) column (Boehringer Mannheim) as described (Maniatis, T., Fritsch, E. F. & Sambrook, J. (1982) *Molecular cloning: A laboratory manual* (Cold Spring Harbor Lab., Cold Spring Harbor, N.Y.). Oligo (dT) primed double stranded cDNA is synthesised from 5 µg of poly A(+) RNA using a commercial cDNA synthesis system (Amersham). The reverse transcriptase supplied with the kit is replaced by the RNAseH(−) Superscript II reverse transcriptase (Gibco BRL). The cDNA solution is concentrated on Centricon-100 devices (Amicon), preabsorbed with tRNA, to a final volume of 100 µl. Small cDNAs are removed by passage through a Chromaspin-1000 column (Clontech). BstXI adaptors (Invitrogen) are added using T4 DNA ligase (Boehringer Mannheim) and the cDNAs are size-fractionated on an agarose gel. cDNAs with sizes larger than 2 kb are purified (Qiaex, Qiagen) and ligated into the BstXI sites of the expression vector pcDNAI (invitrogen). An aliquot of the ligation mixture is transformed (BioRad Gene Pulser II) into electrocompetent MC1061/P3 *E.coli* cells. The complexity of the library is estimated to be $2 \times 10^6$ independent clones. The average insert size deduced from the analysis of 48 clones is 2.9 kb (sizes ranging from 2.0 kb to 6.6 kb).

Plasmids for the transfections of COS1 cells are isolated from bacterial colonies obtained after the initial round of cDNA transformation. Briefly, an aliquot of the cDNA library is transformed into electrocompetent MC1061/P3 *E.coli* cells and titrated by plating on agar plates. The cDNA library is divided into pools of approximately 2,000 colonies that are plated on 9 cm agar plates and grown overnight at 37° C. The bacteria are scraped off the plates and plasmid DNA is prepared using ion exchange columns (Qiawell, Qiagen).

EXAMPLE 6

Transfection of COS Cells with cDNA

COS1 cells are obtained from the American Type Culture Collection (ATCC) and grown in Dulbecco's modified Eagle medium (DMEM) supplemented with 10% fetal calf serum (FCS) and 15 µg/ml gentamycin (Gibco BRL) in a humidified atmosphere with 5% $CO_2$.

Plasmid DNA from pools of independent bacterial colonies are introduced into COS1 cells using a modification of the standard DEAE-dextran transfection procedure. Briefly, one day before transfection $7.5 \times 10^5$ cells are seeded per 9 cm dish. The next day the medium is removed and the cells are incubated 15 min in 10 ml of phosphate buffered saline (PBS tablets, Gibco BRL). Afterwards, PBS is removed and 4 ml of 1 mg/ml DEAE-dextran (Pharmacia) in PBS is added to the dish. After 9 min incubation at room temperature the cells are washed twice with 5 ml of PBS each. The PBS is aspirated and 4 µg plasmid DNA (derived from pools of 2,000 independent bacterial colonies) in 540 µl PBS is added to the dish and the cells incubated with the DNA for 30 min at 37° C. with occasional rocking. Subsequently 4 ml of DMEM medium containing 10% NU-serum (Collaborative Research) and 80 µM chloroquine (Sigma) is added. After 4 hrs incubation at 37° C. the medium is removed and the cells are incubated 2 min in 10% (vol/vol) dimethyl sulfoxide (Merck) in PBS. The cells are rinsed with PBS, cell culture medium is added to the culture dishes and the cells are grown for an additional 2 to 3 days.

EXAMPLE 7

Identification of $GABA_B$ Receptor Clone by Ligand Binding Assay

Pools of cDNAs (2000 independent clones each) are analysed for $GABA_B$ receptor expression, after transient transfection into COS1 cells, using a radioligand binding assay with iodinated CGP64213 (specific activity 2,000 Ci/mmol).

Culture dishes with transfected COS1 cells are placed on ice and washed twice with 5ml each of ice-cold Krebs-Henseleit-Tris buffer (20 mM Tris-Cl pH 7.4, 118 mM NaCl, 5.6 mM glucose, 1.2 mM $KH_2PO_4$, 1.2 mM $MgSO_4$, 4.7mM KCl, 1.8 mM $CaCl_2$). Afterwards the cells are incubated with 0.2 nM of $^{125}$I-CGP 64213 in Krebs-Tris buffer (1 ml solution per 9 cm dish). After 80 min incubation at room temperature the dishes are cooled on ice and washed twice for 5 min with 5ml of ice-cold Krebs-Tris buffer. Subsequently the dishes are air dried using a fan and the walls of the plates are removed. For autoradiography, the bottom of the plates are exposed, together with intensifying screens, to Kodak X-OMAT AR films for 2 to 3 weeks at −80° C.

A total of 640,000 independent clones (320 individual pools) from the above mentioned cDNA library are screened. One pool yields a positive signal in the ligand binding assay. The plasmid DNA from this pool is retransformed into electrocompetent MC1061/P3 cells. 10 plasmid pools from 500 colonies each are prepared, two of which rescreened positive in the binding assay. After 4 subsequent rounds of subdivisions of one of the two pools (SIB selection; McCormick, M. (1987) *Methods Enzymol.* 151, 445–449) a single cDNA clone containing a 4376 bp insert is identified. This first cDNA clone identified, originally referred to as F4, is designated GABA$_B$R1a (SEQ ID No. 1). This cDNA clone encompasses a large open reading frame coding for a putative protein of 960 amino acids with a calculated molecular weight of 108 kDa (SEQ ID No.2). According to von Heijne (von Heijne, G. (1986) *Nucl. Acids. Res.* 14, 4683–4691) the first 16 amino acids encode with high probability a signal peptide that is absent in the mature protein. The calculated molecular weight of the predicted mature protein is 106 kDa. Hydrophobicity analysis of the putative protein with the algorithm of Kyte and Dolittle (1982) *J. Mol. Biol.* 157, 105–132, using sequence analysis programs from the University of Wisconsin Genetics Computer Group (Devereux, et al., (1984) *Nucl. Acids. Res.* 12, 387–395) predicts, as expected for a cell surface receptor coupled to G-proteins, several membrane spanning regions. Putative N-glycosylation sites are found at amino acid positions 7, 67, 392, 423, 465, 485, 497 and 614 of the predicted mature protein as set forth in SEQ ID No. 2.

EXAMPLE 8

Assay of Cloned GABA$_B$ Receptor

In order to isolate membranes containing the cloned GABA$_B$ receptor, culture dishes containing GABA$_B$ receptor-expressing COS cells are washed twice with Krebs-Henseleit-Tris buffer. Afterwards the cells are scraped off the dishes, homogenised in a glass-glass homogeniser and centrifuged for 30 min at 4° C. at 40,000 g. The homogenisation and centrifugation step is repeated once. The pellet is resuspended in buffer and stored in liquid nitrogen until further analysis.

Membranes from COS1 cells transfected with the GABA$_B$ receptor cDNA (membranes derived in a similar manner from brain tissue are used for reference) are suspended in Krebs-Henseleit-Tris buffer at a concentration of approximately 1 mg/mi. The membranes are then incubated in the dark with 0.6 nM $^{125}$I-CGP 71872 for one hour at room temperature. In control experiments 1 μM of unlabeled CGP 54626A, a GABA$_B$ receptor specific antagonist, is included. The incubation is terminated by centrifugation at 20,000 g for 10 min at 4° C. The pellet is washed once in buffer to remove unbound from bound photoaffinity label. The pellet is resuspended in buffer and illuminated with UV light (365 nm, 24 W) for 3 min. The suspension is again centrifuged (20 min, 40,000 g). The pellet is washed in buffer, dissolved in SDS sample buffer and separated on a 6% SDS gel according to Laemmli, U.K (1970) *Nature* 227, 680–685. The gel is dried and, together with intensifying screens, exposed to Dupont Reflection NEF-495 X-ray films overnight. The protein expressed from the 4,376 bp cDNA clone has an apparent molecular mass of about 120 kDa (FIG. 1). The apparent molecular weight of the recombinant GABA$_B$ receptor is estimated from gel mobility relative to those of SDS-PAGE standards (BioRad).

Figure 2:
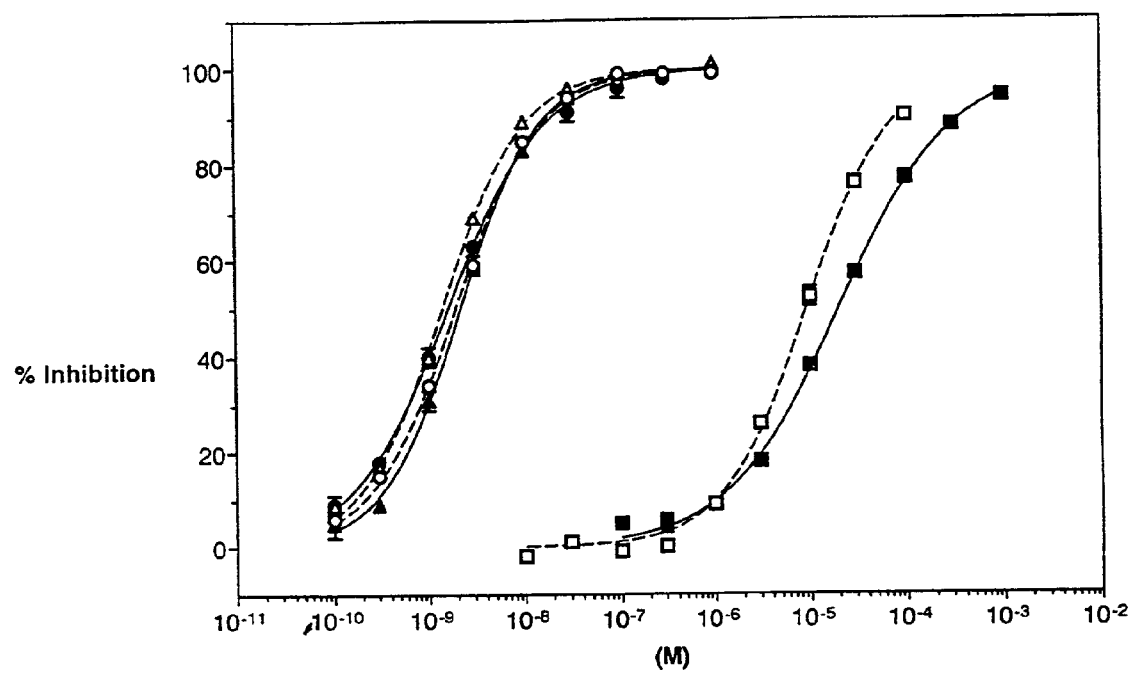
FIG. 2 shows the inhibition of [125I]CGP 64213 binding to $GABA_B$ receptors in membranes from rat cerebral cortex (open symbols) and recombinant $GABA_B$R1a receptors in membranes from COS 1 cells (closed symbols) by the $GABA_B$ receptor antagonists CGP 54626A (●), CGP 64213 (▲) and CGP 35348 (■).
Figure 3:
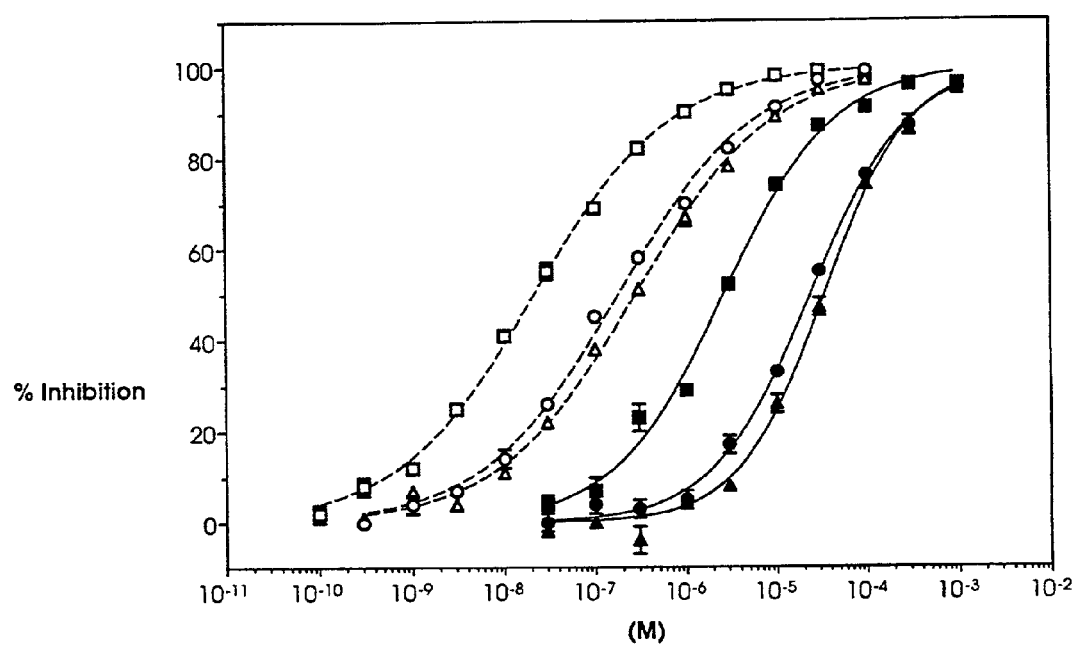
FIG. 3 shows the inhibition of [125I]CGP 64213 binding to $GABA_B$ receptors in membranes from rat cerebral cortex (open symbols) and recombinant $GABA_B$R1a receptors in membranes from COS 1 cells (closed symbols) by the $GABA_B$ receptor agonists GABA (●), L-baclofen (▲) and APPA 3-(aminopropyl-phosphinic acid )(■).

The binding pharmacology of the GABA$_B$R1a receptor expressed in COS1 cells is compared with the binding pharmacology of native GABA$_B$ receptors in rat cerebral cortex membranes. To that aim, the binding characteristics of the radioligand [$^{125}$I]CGP 64213 and the inhibition of this binding by selected GABA$_B$ receptor antagonists and agonists are compared. The dissociation constant K$_D$ for the GABA$_B$R1a receptor expressed in COS cells is determined to be 1.85 nM. The K$_D$ of GABA$_B$ receptors expressed in cortex membranes is determined to be 2.7 nM and thus is similar to the value obtained for the recombinant receptor. The IC$_{50}$ values (Table 1) and the slopes of the inhibition curves (FIG. 2) for the GABA$_B$ receptor antagonists CGP 54626A (Froestl et al., (1992) *Pharmacol. Communications* 2, 52–56), CGP 71872, CGP 64213 and CGP 35348 (Froestl et. al., 1992) are very similar for recombinant and native receptors. The rank order of affinity for the agonists GABA, L-baclofen and CGP 27492 (aminophosphinic acid, APPA) is identical at recombinant and native receptors, however the agonist affinity is always significantly lower at the recombinant GABA$_B$R1a receptor (FIG. 3, Table 1). It is known that GTP or its stable analogue Gpp(NH)p reduce the affinity of agonists at native GABA$_B$ receptors by decoupling the receptors from their G-proteins (Hill et al., (1984) *J.Neurochem.* 42, 652–657). Therefore, the lower affinity of agonists at the recombinant receptor may reflect the fact that in COS cells the G-proteins that normally couple to GABA$_B$ receptors in brain cells are not available. We have determined that for rat cortex GABA$_B$ receptors the IC$_{50}$ value of L-baclofen is shifted from 170 nM to 10 μM in the presence of 300 μM Gpp(NH)p. Thus decoupling G-proteins from native GABA$_B$ receptors results in an IC$_{50}$ value comparable to the 34 μM obtained for the recombinant GABA$_B$R1a receptor expressed in COS cells. In conclusion, the recombinant GABA$_B$R1a receptor shows similar binding pharmacology as native GABA$_B$ receptors from rat cortex.

TABLE 1

BINDING PHARMACOLOGY OF NATIVE AND RECOMBINANT GABA$_B$ RECEPTORS
Inhibition of [$^{125}$I]CGP 64213 binding by GABA$_B$ receptor antagonists and agonists

|  | Rat cerebral cortex IC$_{50}$ (μM) | COS1 cells IC$_{50}$ (μM) |
|---|---|---|
| ANTAGONISTS |  |  |
| CGP 54626A | 0.0019 | 0.0016 |
| CGP 64213 | 0.0014 | 0.0022 |
| CGP 71872 | 0.0021 | 0.0038 |
| CGP 35348 | 9.3 | 20.0 |
| AGONISTS |  |  |
| GABA | 0.13 | 23.9 |
| L-baclofen | 0.17 | 34.0 |
| CGP 27492 (APPA) | 0.018 | 2.6 |
| CGP 47656 (partial agonist) | 0.28 | 12.3 |

EXAMPLE 9

Use of the GABA$_B$R1a Receptor cDNA to Clone Related Genes

The rat GABA$_B$R1a-receptor cDNA isolated (SEQ ID No. 1) is useful as a probe to identify and isolate additional cDNAs, genes and proteins of the GABA$_B$-receptor gene family. It is also useful to identify and isolate cDNAs, genes and proteins of the GABA$_B$-receptor gene family in other species, such as for example humans.

In order to isolate a further rat clone (referred to as GABA$_B$R1b) and human GABA$_B$ receptor clones, the abovementioned rat library and a human fetal brain cDNA library (Clontech, Palo Alto, cat. No. HL3025s) are cross-hybridised with the GABA$_B$R1a cDNA under suitable hybridisation conditions. The human library is an unidirectional oligo (dT)-primed library consisting of $1.2 \times 10^6$ independent cDNA clones inserted into the expression vector pcDNAI. The method of screening a plasmid library by colony hybridisation is described in Sambrook et al. (1989). The hybridisation probe used is a $^{32}$P-labelled 1.3 kb PvuII/ScaI fragment corresponding to bases 1931 to 3264 of the GABA$_B$R1a cDNA (SEQ ID No. 1). Hybridisation is in 0.5 M NaH$_2$PO$_4$ (pH 7.2), 7% SDS, 1 mM EDTA at 60° C. overnight. Subsequent wash steps are for one hour at a final stringency of 0.5×SSC, 0.1% SDS at 55° C. (rat library) or 2×SSC, 0.1% SDS at 50° C. (human library). Kodak X OMAT AR films are exposed to the membranes overnight at −80° C. with intensifying screens. The X-ray films are aligned to the agar plates with the bacterial colonies and colonies containing cross-hybridising cDNA clones are isolated. The bacteria are replated on agar dishes and the colony hybridisation screen is repeated twice. The individual colonies obtained are further analysed by Southern blot hybridisation. Selected cDNA clones are analysed by sequencing and a 2, 9 kb cDNA for rat GABA$_B$R1b characterised (see SEQ ID No. 5). This cDNA encodes a protein of 844 amino acids (see SEQ ID No. 6). The mature GABA$_B$R1b differs from the former GABA$_B$R1a in that the N-terminal 147 amino acid residues are replaced by 18 different residues. Presumably, these two GABA$_B$ receptor variants are derived from the same gene by alternative splicing. Those clones which are positive in screening the human library are also analysed by sequencing and reveal one clone termed GABA$_B$R1a/b (see SEQ ID No. 3) with a partial sequence encoding a receptor protein of 793 amino acid residues (see SEQ ID No. 4), as well as another clone termed GABA$_B$ R1b human (see SEQ ID No. 7) which represents a full-length cDNA encoding a human GABA$_B$ receptor having 844 amino acids (see SEQ ID No. 8).

EXAMPLE 10

Figure 5:
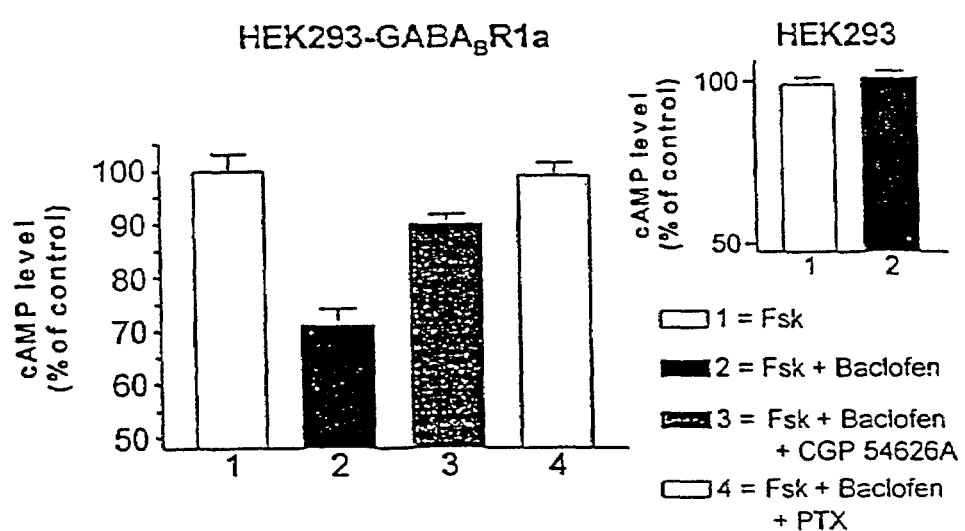
FIG. 5 shows the results of assays concerning pharmacological properties of native and recombinant $GABA_B$ receptors. $GABA_B$R1a mediates inhibition of adenylate cyclase. HEK293 cells stably expressing $GABA_B$R1a are treated with 20 μM forskolin (Fsk) to stimulate cAMP formation (100%). Fsk induced cAMP accumulation is reduced significantly (2P<0.001; Dunnett's t-test) upon simultaneous addition of 300 μM L-baclofen. The effect of L-baclofen is antagonised in the presence of 10 μM CGP54626A. Preincubation of the cells with 10 ng/ml pertussis toxin (PTX) for 15–20 h completely abolishes the effect of L-baclofen. No L-baclofen response is observed in non-transfected HEK293 cells (insert). Bars represent mean values+S.E.M. of at least three independent experiments performed in quadruplicate.

GABA$_B$ Receptors Stably Expressed in HEK293 Cells Negatively Couple to Adenylate Cyclase GABA$_B$ receptors are described to inhibit adenylate cyclase activity, stimulate phospholipase A$_2$, activate K$^+$-channels, inactivate voltage-dependent Ca$^{2+}$-channels and to modulate inositol phospholipid hydrolysis. As GABA$_B$R1a and -b have identical sequence in all domains predicted to be intracellular they are expected to be able to couple to the same effector systems. Using rat cortical slice preparations, L-baclofen has been shown to reduce forskolin-stimulated cAMP accumulation by about 40 percent. The ability of GABA$_B$R1a stably expressed in HEK293 cells to reduce forskolin-stimulated cAMP accumulation is analysed (FIG. 5). We chose concentrations of forskolin and L-baclofen that should produce a maximal effect. Forskolin stimulates cAMP levels in HEK293 cells to more than ten times over the basal level. Stimulation of recombinantly expressed GABA$_B$ receptors by co-addition of 300 μM L-baclofen reduces forskolin stimulated cAMP accumulation by approximately 30 percent. This inhibition is antagonised by CGP54626A, a GABA$_B$ receptor antagonist. The modulation of adenylate cyclase activity by GABA$_B$R1a is sensitive to pertussis toxin, indicating that in HEK293 cells, which are deficient in G$_O$, GABA$_B$R1a couples to G$_i$. As a control, L-baclofen does not inhibit forskolin-stimulated cAMP formation in untransfected HEK293 cells (FIG. 5).

Deposition Data

The GABA$_B$ receptor clone GABA$_B$R1a derived from rat was deposited under the Budapest Treaty at the Deutsche Sammlung von Microorganismen und Zellkulturen GmbH (DSMZ), Mascheroder Weg 1b, D-38124 Braunschweig, Germany, with an effective deposition date of May 17, 1996 under the accession number DSM 10689.

The GABA$_B$ receptor clones GABA$_B$R1b derived from rat as well as GABA$_B$R1b derived from human sources were deposited under the Budapest Treaty at the Deutsche Sammiung von Microorganismen und Zellkulturen GmbH (DSMZ), Mascheroder Weg 1b, D-38124 Braunschweig, Germany, with an effective deposition date of Feb. 21, 1997 under the accession numbers DSM 11422 and 11421, respectively.

What is claimed is:

1. The isolated polypeptide of SEQ ID NO: 2.
2. An isolated polypeptide encoded by a polynucleotide which hybridizes under highly stringent conditions to the polynucleotide of SEQ ID NO: 1, wherein said highly stringent hybridization conditions end with a wash step of 65° C., 0.2×SSC and 0.1% SDS and wherein said polypeptide binds GABA.

* * * * *

SEQUENCE LISTING

```
<160> NUMBER OF SEQ ID NOS: 8

<210> SEQ ID NO 1
<211> LENGTH: 4376
<212> TYPE: DNA
<213> ORGANISM: Rattus norvegicus
<220> FEATURE:
<221> NAME/KEY: CDS
<222> LOCATION: (182)..(3061)
<223> OTHER INFORMATION: Clone: GABABR1a rat
<221> NAME/KEY: mat_peptide
<222> LOCATION: (182)..(3061)

<400> SEQUENCE: 1
gtggggtttg cgggtagcga tcgagaaggg gagagacccc ggccaggcag gagcctggat      60
tcctgtggaa gaagaacagg gggaggggaa gctggaggac cgggagggag aacgggagc     120 cgcggccggg cctggggcct tgaggcccgg ggagagccgc ggagcgggac cggccgccga    180
```

```
g atg ctg ctg ctg ctg gtg cct ctc ttc ctc cgc ccc ctg ggc gct      229
  Met Leu Leu Leu Leu Val Pro Leu Phe Leu Arg Pro Leu Gly Ala
   1               5                  10                 15 ggc ggg gcg cag acc ccc aac gcc acc tcg gaa ggt tgc cag att ata    277
Gly Gly Ala Gln Thr Pro Asn Ala Thr Ser Glu Gly Cys Gln Ile Ile
              20                  25                  30 cat ccg ccc tgg gaa ggt ggc atc agg tac cgt ggc ttg act cgc gac    325
His Pro Pro Trp Glu Gly Gly Ile Arg Tyr Arg Gly Leu Thr Arg Asp
          35                  40                  45 cag gtg aag gcc atc aac ttc ctg cct gtg gac tat gag atc gaa tat    373
Gln Val Lys Ala Ile Asn Phe Leu Pro Val Asp Tyr Glu Ile Glu Tyr
 50                  55                  60 gtg tgc cga ggg gag cgc gag gtg gtg ggg ccc aag gtg cgc aaa tgc    421
Val Cys Arg Gly Glu Arg Glu Val Val Gly Pro Lys Val Arg Lys Cys
 65              70                  75                  80 ctg gcc aac ggc tcc tgg acg gat atg gac aca ccc agc cgc tgt gtc    469
Leu Ala Asn Gly Ser Trp Thr Asp Met Asp Thr Pro Ser Arg Cys Val
                 85                  90                  95 cga atc tgc tcc aag tct tat ttg acc ctg gaa aat ggg aag gtt ttc    517
Arg Ile Cys Ser Lys Ser Tyr Leu Thr Leu Glu Asn Gly Lys Val Phe
            100                 105                 110 ctg acg ggt ggg gac ctc cca gct ctg gat gga gcc cgg gtg gag ttc    565
Leu Thr Gly Gly Asp Leu Pro Ala Leu Asp Gly Ala Arg Val Glu Phe
        115                 120                 125 cga tgt gac ccc gac ttc cat ctg gtg ggc agc tcc cgg agc gtc tgt    613
Arg Cys Asp Pro Asp Phe His Leu Val Gly Ser Ser Arg Ser Val Cys
    130                 135                 140 agt cag ggc cag tgg agc acc ccc aag ccc cac tgc cag gtg aat cga    661
Ser Gln Gly Gln Trp Ser Thr Pro Lys Pro His Cys Gln Val Asn Arg
145                 150                 155                 160 acg cca cac tca gaa cgg cgt gca gta tac atc ggg gcg ctg ttt ccc    709
Thr Pro His Ser Glu Arg Arg Ala Val Tyr Ile Gly Ala Leu Phe Pro
                165                 170                 175 atg agc ggg ggc tgg ccg ggg ggc cag gcc tgc cag ccc gcg gtg gag    757
Met Ser Gly Gly Trp Pro Gly Gly Gln Ala Cys Gln Pro Ala Val Glu
            180                 185                 190 atg gcg ctg gag gac gtt aac agc cgc aga gac atc ctg ccg gac tac    805
Met Ala Leu Glu Asp Val Asn Ser Arg Arg Asp Ile Leu Pro Asp Tyr
        195                 200                 205 gag ctc aag ctt atc cac cac gac agc aag tgt gac cca ggg caa gcc    853
Glu Leu Lys Leu Ile His His Asp Ser Lys Cys Asp Pro Gly Gln Ala
    210                 215                 220 acc aag tac ttg tac gaa cta ctc tac aat gac ccc atc aag atc att    901
Thr Lys Tyr Leu Tyr Glu Leu Leu Tyr Asn Asp Pro Ile Lys Ile Ile
225                 230                 235                 240 ctc atg cct ggc tgt agt tct gtc tcc aca ctt gta gct gag gct gcc    949
Leu Met Pro Gly Cys Ser Ser Val Ser Thr Leu Val Ala Glu Ala Ala
                245                 250                 255 cgg atg tgg aac ctt att gtg ctc tca tat ggc tcc agt tca cca gcc    997
Arg Met Trp Asn Leu Ile Val Leu Ser Tyr Gly Ser Ser Ser Pro Ala
            260                 265                 270 ttg tca aac cga cag cgg ttt ccc acg ttc ttc cgg acg cat cca tcc    1045
Leu Ser Asn Arg Gln Arg Phe Pro Thr Phe Phe Arg Thr His Pro Ser
        275                 280                 285 gcc aca ctc cac aat ccc acc cgg gtg aaa ctc ttc gaa aag tgg ggc    1093
Ala Thr Leu His Asn Pro Thr Arg Val Lys Leu Phe Glu Lys Trp Gly
    290                 295                 300 tgg aag aag atc gct acc atc caa cag acc acc gag gtc ttc acc tca    1141
Trp Lys Lys Ile Ala Thr Ile Gln Gln Thr Thr Glu Val Phe Thr Ser
305                 310                 315                 320
```

-continued

| | |
|---|---|
| acg ctg gat gac ctg gag gag cga gtg aaa gag gct ggg atc gag atc<br>Thr Leu Asp Asp Leu Glu Glu Arg Val Lys Glu Ala Gly Ile Glu Ile<br>325                        330                      335 | 1189 |
| act ttc cga cag agt ttc ttc tcg gat cca gct gtg cct gtt aaa aac<br>Thr Phe Arg Gln Ser Phe Phe Ser Asp Pro Ala Val Pro Val Lys Asn<br>     340                   345                   350 | 1237 |
| ctg aag cgt caa gat gct cga atc atc gtg gga ctt ttc tat gag acg<br>Leu Lys Arg Gln Asp Ala Arg Ile Ile Val Gly Leu Phe Tyr Glu Thr<br>355                        360                      365 | 1285 |
| gaa gcc cgg aaa gtt ttt tgt gag gtc tat aag gaa agg ctc ttt ggg<br>Glu Ala Arg Lys Val Phe Cys Glu Val Tyr Lys Glu Arg Leu Phe Gly<br>     370                   375                   380 | 1333 |
| aag aag tac gtc tgg ttc ctc atc ggg tgg tat gct gac aac tgg ttc<br>Lys Lys Tyr Val Trp Phe Leu Ile Gly Trp Tyr Ala Asp Asn Trp Phe<br>385                        390                      395                   400 | 1381 |
| aag acc tat gac ccg tca atc aat tgt aca gtg gaa gaa atg acc gag<br>Lys Thr Tyr Asp Pro Ser Ile Asn Cys Thr Val Glu Glu Met Thr Glu<br>                  405                   410                   415 | 1429 |
| gcg gtg gag ggc cac atc acc acg gag att gtc atg ctg aac cct gcc<br>Ala Val Glu Gly His Ile Thr Thr Glu Ile Val Met Leu Asn Pro Ala<br>              420                   425                   430 | 1477 |
| aac acc cga agc att tcc aac atg acg tca cag gaa ttt gtg gag aaa<br>Asn Thr Arg Ser Ile Ser Asn Met Thr Ser Gln Glu Phe Val Glu Lys<br>435                        440                      445 | 1525 |
| cta acc aag cgg ctg aaa aga cac ccc gag gag act gga ggc ttc cag<br>Leu Thr Lys Arg Leu Lys Arg His Pro Glu Glu Thr Gly Gly Phe Gln<br>     450                   455                   460 | 1573 |
| gag gca cca ctg gcc tat gat gct atc tgg gcc ttg gct ttg gcc ttg<br>Glu Ala Pro Leu Ala Tyr Asp Ala Ile Trp Ala Leu Ala Leu Ala Leu<br>465                        470                      475                   480 | 1621 |
| aac aag acg tct gga gga ggt ggt cgt tcc ggc gtg cgc ctg gag gac<br>Asn Lys Thr Ser Gly Gly Gly Gly Arg Ser Gly Val Arg Leu Glu Asp<br>                  485                   490                   495 | 1669 |
| ttt aac tac aac aac cag acc att aca gac cag atc tac cgg gcc atg<br>Phe Asn Tyr Asn Asn Gln Thr Ile Thr Asp Gln Ile Tyr Arg Ala Met<br>              500                   505                   510 | 1717 |
| aac tcc tcc tcc ttt gag ggc gtt tct ggc cat gtg gtc ttt gat gcc<br>Asn Ser Ser Ser Phe Glu Gly Val Ser Gly His Val Val Phe Asp Ala<br>515                        520                      525 | 1765 |
| agc ggc tcc cgg atg gca tgg aca ctt atc gag cag cta cag ggc ggc<br>Ser Gly Ser Arg Met Ala Trp Thr Leu Ile Glu Gln Leu Gln Gly Gly<br>     530                   535                   540 | 1813 |
| agc tac aag aag atc ggc tac tac gac agc acc aag gat gat ctt tcc<br>Ser Tyr Lys Lys Ile Gly Tyr Tyr Asp Ser Thr Lys Asp Asp Leu Ser<br>545                        550                      555                   560 | 1861 |
| tgg tcc aaa acg gac aag tgg att gga ggg tct ccc cca gct gac cag<br>Trp Ser Lys Thr Asp Lys Trp Ile Gly Gly Ser Pro Pro Ala Asp Gln<br>                  565                   570                   575 | 1909 |
| acc ttg gtc atc aag aca ttc cgt ttc ctg tct cag aaa ctc ttt atc<br>Thr Leu Val Ile Lys Thr Phe Arg Phe Leu Ser Gln Lys Leu Phe Ile<br>              580                   585                   590 | 1957 |
| tcc gtc tca gtt ctc tcc agc ctg ggc att gtt ctt gct gtt gtc tgt<br>Ser Val Ser Val Leu Ser Ser Leu Gly Ile Val Leu Ala Val Val Cys<br>595                        600                      605 | 2005 |
| ctg tcc ttt aac atc tac aac tcc cac gtt cgt tat atc cag aac tcc<br>Leu Ser Phe Asn Ile Tyr Asn Ser His Val Arg Tyr Ile Gln Asn Ser<br>     610                   615                   620 | 2053 |
| cag ccc aac ctg aac aat ctg act gct gtg ggc tgc tca ctg gca ctg<br>Gln Pro Asn Leu Asn Asn Leu Thr Ala Val Gly Cys Ser Leu Ala Leu<br>625                        630                      635                   640 | 2101 |

-continued

```
gct gct gtc ttc cct ctc ggg ctg gat ggt tac cac ata ggg aga agc         2149
Ala Ala Val Phe Pro Leu Gly Leu Asp Gly Tyr His Ile Gly Arg Ser
            645                 650                 655 cag ttc ccg ttt gtc tgc cag gcc cgc ctt tgg ctc ttg ggc ttg ggc         2197
Gln Phe Pro Phe Val Cys Gln Ala Arg Leu Trp Leu Leu Gly Leu Gly
660                 665                 670 ttt agt ctg ggc tat ggc tct atg ttc acc aag atc tgg tgg gtc cac         2245
Phe Ser Leu Gly Tyr Gly Ser Met Phe Thr Lys Ile Trp Trp Val His
            675                 680                 685 aca gtc ttc acg aag aag gag gag aag aag gag tgg agg aag acc cta         2293
Thr Val Phe Thr Lys Lys Glu Glu Lys Lys Glu Trp Arg Lys Thr Leu
        690                 695                 700 gag ccc tgg aaa ctc tat gcc act gtg ggc ctg ctg gtg ggc atg gat         2341
Glu Pro Trp Lys Leu Tyr Ala Thr Val Gly Leu Leu Val Gly Met Asp
705                 710                 715                 720 gtc ctg act ctt gcc atc tgg cag att gtg gac ccc ttg cac cga acc         2389
Val Leu Thr Leu Ala Ile Trp Gln Ile Val Asp Pro Leu His Arg Thr
                725                 730                 735 att gag act ttt gcc aag gag gaa cca aag gaa gac atc gat gtc tcc         2437
Ile Glu Thr Phe Ala Lys Glu Glu Pro Lys Glu Asp Ile Asp Val Ser
            740                 745                 750 att ctg ccc cag ttg gag cac tgc agc tcc aag aag atg aat acg tgg         2485
Ile Leu Pro Gln Leu Glu His Cys Ser Ser Lys Lys Met Asn Thr Trp
        755                 760                 765 ctt ggc att ttc tat ggt tac aag ggg ctg ctg ctg ctg gga atc         2533
Leu Gly Ile Phe Tyr Gly Tyr Lys Gly Leu Leu Leu Leu Gly Ile
    770                 775                 780 ttt ctt gct tac gaa acc aag agc gtg tcc act gaa aag atc aat gac         2581
Phe Leu Ala Tyr Glu Thr Lys Ser Val Ser Thr Glu Lys Ile Asn Asp
785                 790                 795                 800 cac agg gcc gtg ggc atg gct atc tac aat gtc gcg gtc ctg tgt ctc         2629
His Arg Ala Val Gly Met Ala Ile Tyr Asn Val Ala Val Leu Cys Leu
                805                 810                 815 atc act gct cct gtg acc atg atc ctt tcc agt cag cag gac gca gcc         2677
Ile Thr Ala Pro Val Thr Met Ile Leu Ser Ser Gln Gln Asp Ala Ala
            820                 825                 830 ttt gcc ttt gcc tct ctg gcc atc gtg ttc tct tcc tac atc act ctg         2725
Phe Ala Phe Ala Ser Leu Ala Ile Val Phe Ser Ser Tyr Ile Thr Leu
        835                 840                 845 gtt gtg ctc ttt gtg ccc aag atg cgc agg ctg atc acc cga ggg gaa         2773
Val Val Leu Phe Val Pro Lys Met Arg Arg Leu Ile Thr Arg Gly Glu
    850                 855                 860 tgg cag tct gaa acg cag gac acc atg aaa aca gga tca tcc acc aac         2821
Trp Gln Ser Glu Thr Gln Asp Thr Met Lys Thr Gly Ser Ser Thr Asn
865                 870                 875                 880 aac aac gag gaa gag aag tcc cga ctg ttg gag aag gaa aac cga gaa         2869
Asn Asn Glu Glu Glu Lys Ser Arg Leu Leu Glu Lys Glu Asn Arg Glu
                885                 890                 895 ctg gaa aag atc atc gct gag aaa gag gag cgc gtc tct gaa ctg cgc         2917
Leu Glu Lys Ile Ile Ala Glu Lys Glu Glu Arg Val Ser Glu Leu Arg
            900                 905                 910 cat cag ctc cag tct cgg cag caa ctc cgc tca cgg cgc cac ccc cca         2965
His Gln Leu Gln Ser Arg Gln Gln Leu Arg Ser Arg Arg His Pro Pro
        915                 920                 925 aca ccc cca gat ccc tct ggg ggc ctt ccc agg gga ccc tct gag ccc         3013
Thr Pro Pro Asp Pro Ser Gly Gly Leu Pro Arg Gly Pro Ser Glu Pro
    930                 935                 940 cct gac cgg ctt agc tgt gat ggg agt cga gta cat ttg ctt tac aag         3061
Pro Asp Arg Leu Ser Cys Asp Gly Ser Arg Val His Leu Leu Tyr Lys
945                 950                 955                 960
```

-continued

```
tgaggggggca tggagaagga tcaagccagt aggggaggga agggtctggg aagagggtgg    3121
gggcctggga ggagggtaag gactcctatc tccaacctgg agagcacacg ctccaatccc    3181
cctcttataa atacatgtcg ctctgtgcat ctggggttat ttgggtctcc agtactctgg    3241
gaaacagact gttttctttc tcccctataa ttttatatct ccacttcaca ggttttgttt    3301
gaaccctgct tggagttatt attcactcat ggctccagag gggcatctca tttttctccg    3361
gtagcctgtc ttgtacagtt accacagcaa ctcctgtcat ttcagcagca ggggtcttcc    3421
tacactagca gggctctcgc tctctccatt tttcagcctc agaatctcct tccattattc    3481
ttctccttct acatgtctcc atggcttcct ctcccagggg actcgttcta cacacataca    3541
cacacacaca cacacacaca cacacacaca cacacacaca caccccgcat cctgccctct    3601
cctaggcagc tgcatgtcgt cctgtacaaa tgtgctcgct tctgagtgct ttgtgcggcc    3661
gttcacttgt gctgtctgca taagctgcgt ctgtgagtgc acggtggttt gtgggtgcgt    3721
gaagtggcat gctccggtag gtgtgtatga tgcgttgagc acgctacgct gtctccctca    3781
tgtgcacgca ttgtgtctgc ttatgttttta cttgtatgcc tctgtgtact gtgtgtgtgt    3841
gtgtgtgtgc ccacgcgtgc gcccgtgtgc atgcgttcgt gttgccctga ctggctgtct    3901
cagccttctg agtaattggg attccagttg tctgtctagc tcatgtcctg tcttcttcca    3961
gtagagccgt gaacacccaa cacacacagt taatcgggct ccccccagtc catgttttct    4021
gagccatcca aaaactctcc ttggccttag gttcatctac aaatgttccc tctgttcttt    4081
gctctcgtgc gtccaccttc attctcttca gtcatttctc agatctgctg cgtcgtggtt    4141
tcctttcctt cattatcatc gtcattattt ttcagaactt aagggaaaaa gaaatgggga    4201
caggttggag gctgtttcca gtggaatagt gggtgcgcgt cctgaccaaa tgaaggcacg    4261
gacagatgga ctgacggggc gggaggcggc gtccctttca cactgtggtg tctcttgggg    4321
gggaaggatc tccctgaatc tcaataaagc agtgaacagt aaaaaaaaaa aaaaa         4376
```

<210> SEQ ID NO 2
<211> LENGTH: 960
<212> TYPE: PRT
<213> ORGANISM: Rattus norvegicus

<400> SEQUENCE: 2

```
Met Leu Leu Leu Leu Val Pro Leu Phe Leu Arg Pro Leu Gly Ala
 1               5                  10                  15

Gly Gly Ala Gln Thr Pro Asn Ala Thr Ser Glu Gly Cys Gln Ile Ile
             20                  25                  30

His Pro Pro Trp Glu Gly Gly Ile Arg Tyr Arg Gly Leu Thr Arg Asp
         35                  40                  45

Gln Val Lys Ala Ile Asn Phe Leu Pro Val Asp Tyr Glu Ile Glu Tyr
     50                  55                  60

Val Cys Arg Gly Glu Arg Glu Val Val Gly Pro Lys Val Arg Lys Cys
 65                  70                  75                  80

Leu Ala Asn Gly Ser Trp Thr Asp Met Asp Thr Pro Ser Arg Cys Val
                 85                  90                  95

Arg Ile Cys Ser Lys Ser Tyr Leu Thr Leu Glu Asn Gly Lys Val Phe
            100                 105                 110

Leu Thr Gly Gly Asp Leu Pro Ala Leu Asp Gly Ala Arg Val Glu Phe
        115                 120                 125

Arg Cys Asp Pro Asp Phe His Leu Val Gly Ser Ser Arg Ser Val Cys
    130                 135                 140
```

-continued

```
Ser Gln Gly Gln Trp Ser Thr Pro Lys Pro His Cys Gln Val Asn Arg
145                 150                 155                 160

Thr Pro His Ser Glu Arg Arg Ala Val Tyr Ile Gly Ala Leu Phe Pro
            165                 170                 175

Met Ser Gly Gly Trp Pro Gly Gly Gln Ala Cys Gln Pro Ala Val Glu
        180                 185                 190

Met Ala Leu Glu Asp Val Asn Ser Arg Arg Asp Ile Leu Pro Asp Tyr
    195                 200                 205

Glu Leu Lys Leu Ile His His Asp Ser Lys Cys Asp Pro Gly Gln Ala
    210                 215                 220

Thr Lys Tyr Leu Tyr Glu Leu Leu Tyr Asn Asp Pro Ile Lys Ile Ile
225                 230                 235                 240

Leu Met Pro Gly Cys Ser Ser Val Ser Thr Leu Val Ala Glu Ala Ala
                245                 250                 255

Arg Met Trp Asn Leu Ile Val Leu Ser Tyr Gly Ser Ser Ser Pro Ala
            260                 265                 270

Leu Ser Asn Arg Gln Arg Phe Pro Thr Phe Phe Arg Thr His Pro Ser
        275                 280                 285

Ala Thr Leu His Asn Pro Thr Arg Val Lys Leu Phe Glu Lys Trp Gly
    290                 295                 300

Trp Lys Lys Ile Ala Thr Ile Gln Gln Thr Thr Glu Val Phe Thr Ser
305                 310                 315                 320

Thr Leu Asp Asp Leu Glu Glu Arg Val Lys Glu Ala Gly Ile Glu Ile
                325                 330                 335

Thr Phe Arg Gln Ser Phe Phe Ser Asp Pro Ala Val Pro Val Lys Asn
            340                 345                 350

Leu Lys Arg Gln Asp Ala Arg Ile Ile Val Gly Leu Phe Tyr Glu Thr
        355                 360                 365

Glu Ala Arg Lys Val Phe Cys Glu Val Tyr Lys Glu Arg Leu Phe Gly
    370                 375                 380

Lys Lys Tyr Val Trp Phe Leu Ile Gly Trp Tyr Ala Asp Asn Trp Phe
385                 390                 395                 400

Lys Thr Tyr Asp Pro Ser Ile Asn Cys Thr Val Glu Glu Met Thr Glu
                405                 410                 415

Ala Val Glu Gly His Ile Thr Thr Glu Ile Val Met Leu Asn Pro Ala
            420                 425                 430

Asn Thr Arg Ser Ile Ser Asn Met Thr Ser Gln Glu Phe Val Glu Lys
        435                 440                 445

Leu Thr Lys Arg Leu Lys Arg His Pro Glu Glu Thr Gly Gly Phe Gln
    450                 455                 460

Glu Ala Pro Leu Ala Tyr Asp Ala Ile Trp Ala Leu Ala Leu Ala Leu
465                 470                 475                 480

Asn Lys Thr Ser Gly Gly Gly Arg Ser Gly Val Arg Leu Glu Asp
                485                 490                 495

Phe Asn Tyr Asn Asn Gln Thr Ile Thr Asp Gln Ile Tyr Arg Ala Met
            500                 505                 510

Asn Ser Ser Ser Phe Glu Gly Val Ser Gly His Val Val Phe Asp Ala
        515                 520                 525

Ser Gly Ser Arg Met Ala Trp Thr Leu Ile Glu Gln Leu Gln Gly Gly
    530                 535                 540

Ser Tyr Lys Lys Ile Gly Tyr Tyr Asp Ser Thr Lys Asp Asp Leu Ser
545                 550                 555                 560
```

```
Trp Ser Lys Thr Asp Lys Trp Ile Gly Gly Ser Pro Ala Asp Gln
            565                 570                 575

Thr Leu Val Ile Lys Thr Phe Arg Phe Leu Ser Gln Lys Leu Phe Ile
            580                 585                 590

Ser Val Ser Val Leu Ser Ser Leu Gly Ile Val Leu Ala Val Val Cys
            595                 600                 605

Leu Ser Phe Asn Ile Tyr Asn Ser His Val Arg Tyr Ile Gln Asn Ser
            610                 615                 620

Gln Pro Asn Leu Asn Asn Leu Thr Ala Val Gly Cys Ser Leu Ala Leu
625                 630                 635                 640

Ala Ala Val Phe Pro Leu Gly Leu Asp Gly Tyr His Ile Gly Arg Ser
                645                 650                 655

Gln Phe Pro Phe Val Cys Gln Ala Arg Leu Trp Leu Leu Gly Leu Gly
            660                 665                 670

Phe Ser Leu Gly Tyr Gly Ser Met Phe Thr Lys Ile Trp Trp Val His
            675                 680                 685

Thr Val Phe Thr Lys Lys Glu Glu Lys Lys Glu Trp Arg Lys Thr Leu
            690                 695                 700

Glu Pro Trp Lys Leu Tyr Ala Thr Val Gly Leu Leu Val Gly Met Asp
705                 710                 715                 720

Val Leu Thr Leu Ala Ile Trp Gln Ile Val Asp Pro Leu His Arg Thr
                725                 730                 735

Ile Glu Thr Phe Ala Lys Glu Glu Pro Lys Glu Asp Ile Asp Val Ser
            740                 745                 750

Ile Leu Pro Gln Leu Glu His Cys Ser Ser Lys Lys Met Asn Thr Trp
            755                 760                 765

Leu Gly Ile Phe Tyr Gly Tyr Lys Gly Leu Leu Leu Leu Gly Ile
            770                 775                 780

Phe Leu Ala Tyr Glu Thr Lys Ser Val Ser Thr Glu Lys Ile Asn Asp
785                 790                 795                 800

His Arg Ala Val Gly Met Ala Ile Tyr Asn Val Ala Val Leu Cys Leu
                805                 810                 815

Ile Thr Ala Pro Val Thr Met Ile Leu Ser Ser Gln Gln Asp Ala Ala
            820                 825                 830

Phe Ala Phe Ala Ser Leu Ala Ile Val Phe Ser Ser Tyr Ile Thr Leu
            835                 840                 845

Val Val Leu Phe Val Pro Lys Met Arg Arg Leu Ile Thr Arg Gly Glu
850                 855                 860

Trp Gln Ser Glu Thr Gln Asp Thr Met Lys Thr Gly Ser Ser Thr Asn
865                 870                 875                 880

Asn Asn Glu Glu Glu Lys Ser Arg Leu Leu Lys Glu Asn Arg Glu
                885                 890                 895

Leu Glu Lys Ile Ile Ala Glu Lys Glu Glu Arg Val Ser Glu Leu Arg
            900                 905                 910

His Gln Leu Gln Ser Arg Gln Gln Leu Arg Ser Arg His Pro Pro
            915                 920                 925

Thr Pro Pro Asp Pro Ser Gly Gly Leu Pro Arg Gly Pro Ser Glu Pro
930                 935                 940

Pro Asp Arg Leu Ser Cys Asp Gly Ser Arg Val His Leu Leu Tyr Lys
945                 950                 955                 960
```

-continued

```
<210> SEQ ID NO 3
<211> LENGTH: 2620
<212> TYPE: DNA
<213> ORGANISM: Homo sapiens
<220> FEATURE:
<221> NAME/KEY: CDS
<222> LOCATION: (1)..(2379)
<223> OTHER INFORMATION: Clone: GABABR1a/b human
<221> NAME/KEY: mat_peptide
<222> LOCATION: (1)..(2379)

<400> SEQUENCE: 3 gca gtg tac atc ggg gca ctg ttt ccc atg agc ggg ggc tgg cca ggg      48
Ala Val Tyr Ile Gly Ala Leu Phe Pro Met Ser Gly Gly Trp Pro Gly
  1               5                  10                  15 ggc cag gcc tgc cag ccc gcg gtg gag atg gcg ctg gag gac gtg aat      96
Gly Gln Ala Cys Gln Pro Ala Val Glu Met Ala Leu Glu Asp Val Asn
             20                  25                  30 agc cgc agg gac atc ctg ccg gac tat gag ctc aag ctc atc cac cac     144
Ser Arg Arg Asp Ile Leu Pro Asp Tyr Glu Leu Lys Leu Ile His His
         35                  40                  45 gac agc aag tgt gat cca ggc caa gcc acc aag tac cta tat gag ctg     192
Asp Ser Lys Cys Asp Pro Gly Gln Ala Thr Lys Tyr Leu Tyr Glu Leu
     50                  55                  60 ctc tac aac gac cct atc aag atc atc ctt atg cct ggc tgc agc tct     240
Leu Tyr Asn Asp Pro Ile Lys Ile Ile Leu Met Pro Gly Cys Ser Ser
 65                  70                  75                  80 gtc tcc acg ctg gtg gct gag gct gct agg atg tgg aac ctc att gtg     288
Val Ser Thr Leu Val Ala Glu Ala Ala Arg Met Trp Asn Leu Ile Val
                 85                  90                  95 ctt tcc tat ggc tcc agc tca cca gcc ctg tca aac cgg cag cgt ttc     336
Leu Ser Tyr Gly Ser Ser Ser Pro Ala Leu Ser Asn Arg Gln Arg Phe
            100                 105                 110 ccc act ttc ttc cga acg cac cca tca gcc aca ctc cac aac cct acc     384
Pro Thr Phe Phe Arg Thr His Pro Ser Ala Thr Leu His Asn Pro Thr
        115                 120                 125 cgc gtg aaa ctc ttt gaa aag tgg ggc tgg aag aag att gct acc atc     432
Arg Val Lys Leu Phe Glu Lys Trp Gly Trp Lys Lys Ile Ala Thr Ile
    130                 135                 140 cag cag acc act gag gtc ttc act tcg act ctg gac gac ctg gag gaa     480
Gln Gln Thr Thr Glu Val Phe Thr Ser Thr Leu Asp Asp Leu Glu Glu
145                 150                 155                 160 cga gtg aag gag gct gga att gag att act ttc cgc cag agt ttc ttc     528
Arg Val Lys Glu Ala Gly Ile Glu Ile Thr Phe Arg Gln Ser Phe Phe
                165                 170                 175 tca gat cca gct gtg ccc gtc aaa aac ctg aag cgc cag gat gcc cga     576
Ser Asp Pro Ala Val Pro Val Lys Asn Leu Lys Arg Gln Asp Ala Arg
            180                 185                 190 atc atc gtg gga ctt ttc tat gag act gaa gcc cgg aaa gtt ttt tgt     624
Ile Ile Val Gly Leu Phe Tyr Glu Thr Glu Ala Arg Lys Val Phe Cys
        195                 200                 205 gag gtg tac aag gag cgt ctc ttt ggg aag aag tac gtc tgg ttc ctc     672
Glu Val Tyr Lys Glu Arg Leu Phe Gly Lys Lys Tyr Val Trp Phe Leu
    210                 215                 220 att ggg tgg tat gct gac aat tgg ttc aag atc tac gac cct tct atc     720
Ile Gly Trp Tyr Ala Asp Asn Trp Phe Lys Ile Tyr Asp Pro Ser Ile
225                 230                 235                 240 aac tgc aca gtg gat gag atg act gag gcg gtg gag ggc cac atc aca     768
Asn Cys Thr Val Asp Glu Met Thr Glu Ala Val Glu Gly His Ile Thr
                245                 250                 255
```

| | | |
|---|---|---|
| act gag att gtc atg ctg aat cct gcc aat acc cgc agc att tcc aac<br>Thr Glu Ile Val Met Leu Asn Pro Ala Asn Thr Arg Ser Ile Ser Asn<br>260 265 270 | | 816 |
| atg aca tcc cag gaa ttt gtg gag aaa cta acc aag cga ctg aaa aga<br>Met Thr Ser Gln Glu Phe Val Glu Lys Leu Thr Lys Arg Leu Lys Arg<br>275 280 285 | | 864 |
| cac cct gag gag aca gga ggc ttc cag gag gca ccg ctg gcc tat gat<br>His Pro Glu Glu Thr Gly Gly Phe Gln Glu Ala Pro Leu Ala Tyr Asp<br>290 295 300 | | 912 |
| gcc atc tgg gcc ttg gca ctg gcc ctg aac aag aca tct gga gga ggc<br>Ala Ile Trp Ala Leu Ala Leu Ala Leu Asn Lys Thr Ser Gly Gly Gly<br>305 310 315 320 | | 960 |
| ggc cgt tct ggt gtg cgc ctg gag gac ttc aac tac aac aac cag acc<br>Gly Arg Ser Gly Val Arg Leu Glu Asp Phe Asn Tyr Asn Asn Gln Thr<br>325 330 335 | | 1008 |
| att acc gac caa atc tac cgg gca atg aac tct tcg tcc ttt gag ggt<br>Ile Thr Asp Gln Ile Tyr Arg Ala Met Asn Ser Ser Ser Phe Glu Gly<br>340 345 350 | | 1056 |
| gtc tct ggc cat gtg gtg ttt gat gcc agc ggc tct cgg atg gca tgg<br>Val Ser Gly His Val Val Phe Asp Ala Ser Gly Ser Arg Met Ala Trp<br>355 360 365 | | 1104 |
| acg ctt atc gag cag ctt cag ggt ggc agc tac aag aag att ggc tac<br>Thr Leu Ile Glu Gln Leu Gln Gly Gly Ser Tyr Lys Lys Ile Gly Tyr<br>370 375 380 | | 1152 |
| tat gac agc acc aag gat gat ctt tcc tgg tcc aaa aca gat aaa tgg<br>Tyr Asp Ser Thr Lys Asp Asp Leu Ser Trp Ser Lys Thr Asp Lys Trp<br>385 390 395 400 | | 1200 |
| att gga ggg tcc ccc cca gct gac cag acc ctg gtc atc aag aca ttc<br>Ile Gly Gly Ser Pro Pro Ala Asp Gln Thr Leu Val Ile Lys Thr Phe<br>405 410 415 | | 1248 |
| cgc ttc ctg tca cag aaa ctc ttt atc tcc gtc tca gtt ctc tcc agc<br>Arg Phe Leu Ser Gln Lys Leu Phe Ile Ser Val Ser Val Leu Ser Ser<br>420 425 430 | | 1296 |
| ctg ggc att gtc cta gct gtt gtc tgt ctg tcc ttt aac atc tac aac<br>Leu Gly Ile Val Leu Ala Val Val Cys Leu Ser Phe Asn Ile Tyr Asn<br>435 440 445 | | 1344 |
| tca cat gtc cgt tat atc cag aac tca cag ccc aac ctg aac aac ctg<br>Ser His Val Arg Tyr Ile Gln Asn Ser Gln Pro Asn Leu Asn Asn Leu<br>450 455 460 | | 1392 |
| act gct gtg ggc tgc tca ctg gct tta gct gct gtc ttc ccc ctg ggg<br>Thr Ala Val Gly Cys Ser Leu Ala Leu Ala Ala Val Phe Pro Leu Gly<br>465 470 475 480 | | 1440 |
| ctc gat ggt tac cac att ggg agg aac cag ttt cct ttc gtc tgc cag<br>Leu Asp Gly Tyr His Ile Gly Arg Asn Gln Phe Pro Phe Val Cys Gln<br>485 490 495 | | 1488 |
| gcc cgc ctc tgg ctc ctg ggc ctg ggc ttt agt ctg ggc tac ggt tcc<br>Ala Arg Leu Trp Leu Leu Gly Leu Gly Phe Ser Leu Gly Tyr Gly Ser<br>500 505 510 | | 1536 |
| atg ttc acc aag att tgg tgg gtc cac acg gtc ttc aca aag aag gaa<br>Met Phe Thr Lys Ile Trp Trp Val His Thr Val Phe Thr Lys Lys Glu<br>515 520 525 | | 1584 |
| gaa aag aag gag tgg agg aag act ctg gaa ccc tgg aag ctg tat gcc<br>Glu Lys Lys Glu Trp Arg Lys Thr Leu Glu Pro Trp Lys Leu Tyr Ala<br>530 535 540 | | 1632 |
| aca gtg ggc ctg ctg gtg ggc atg gat gtc ctc act ctc gcc atc tgg<br>Thr Val Gly Leu Leu Val Gly Met Asp Val Leu Thr Leu Ala Ile Trp<br>545 550 555 560 | | 1680 |
| cag atc gtg gac cct ctg cac cgg acc att gag aca ttt gcc aag gag<br>Gln Ile Val Asp Pro Leu His Arg Thr Ile Glu Thr Phe Ala Lys Glu<br>565 570 575 | | 1728 |

```
gaa cct aag gaa gat att gac gtc tct att ctg ccc cag ctg gag cat      1776
Glu Pro Lys Glu Asp Ile Asp Val Ser Ile Leu Pro Gln Leu Glu His
            580                 585                 590 tgc agc tcc agg aag atg aat aca tgg ctt ggc att ttc tat ggt tac      1824
Cys Ser Ser Arg Lys Met Asn Thr Trp Leu Gly Ile Phe Tyr Gly Tyr
        595                 600                 605 aag ggg ctg ctg ctg ctg ctg gga atc ttc ctt gct tat gag acc aag      1872
Lys Gly Leu Leu Leu Leu Leu Gly Ile Phe Leu Ala Tyr Glu Thr Lys
    610                 615                 620 agt gtg tcc act gag aag atc aat gat cac cgg gct gtg ggc atg gct      1920
Ser Val Ser Thr Glu Lys Ile Asn Asp His Arg Ala Val Gly Met Ala
625                 630                 635                 640 atc tac aat gtg gca gtc ctg tgc ctc atc act gct cct gtc acc atg      1968
Ile Tyr Asn Val Ala Val Leu Cys Leu Ile Thr Ala Pro Val Thr Met
                645                 650                 655 att ctg tcc agc cag cag gat gca gcc ttt gcc ttt gcc tct ctt gcc      2016
Ile Leu Ser Ser Gln Gln Asp Ala Ala Phe Ala Phe Ala Ser Leu Ala
            660                 665                 670 ata gtt ttc tcc tcc tat atc act ctt gtt gtg ctc ttt gtg ccc aag      2064
Ile Val Phe Ser Ser Tyr Ile Thr Leu Val Val Leu Phe Val Pro Lys
        675                 680                 685 atg cgc agg ctg atc acc cga ggg gaa tgg cag tcg gag gcg cag gac      2112
Met Arg Arg Leu Ile Thr Arg Gly Glu Trp Gln Ser Glu Ala Gln Asp
    690                 695                 700 acc atg aag aca ggg tca tcg acc aac aac aac gag gag gag aag tcc      2160
Thr Met Lys Thr Gly Ser Ser Thr Asn Asn Asn Glu Glu Glu Lys Ser
705                 710                 715                 720 cgg ctg ttg gag aag gag aac cgt gaa ctg gaa aag atc att gct gag      2208
Arg Leu Leu Glu Lys Glu Asn Arg Glu Leu Glu Lys Ile Ile Ala Glu
                725                 730                 735 aaa gag gag cgt gtc tct gaa ctg cgc cat caa ctc cag tct cgg cag      2256
Lys Glu Glu Arg Val Ser Glu Leu Arg His Gln Leu Gln Ser Arg Gln
            740                 745                 750 cag ctc cgc tcc cgg cgc cac cca ccg aca ccc cca gaa ccc tct ggg      2304
Gln Leu Arg Ser Arg Arg His Pro Pro Thr Pro Pro Glu Pro Ser Gly
        755                 760                 765 ggc ctg ccc agg gga ccc cct gag ccc ccc gac cgg ctt agc tgt gat      2352
Gly Leu Pro Arg Gly Pro Pro Glu Pro Pro Asp Arg Leu Ser Cys Asp
    770                 775                 780 ggg agt cga gtg cat ttg ctt tat aag tgagggtagg gtgagggagg            2399
Gly Ser Arg Val His Leu Leu Tyr Lys
785                 790 acaggccagt aggggagggg aaagggagag gggaagggca ggggactcag gaagcagggg    2459
gtccccatcc ccagctggga agaacatgct atccaatctc atctcttgta aatacatgtc    2519
cccctgtgag ttctgggctg atttgggtct ctcatacctc tgggaaacag accttttct     2579 ctcttactgc ttcatgtaat tttggaattc caccacactg g                        2620

<210> SEQ ID NO 4
<211> LENGTH: 793
<212> TYPE: PRT
<213> ORGANISM: Homo sapiens

<400> SEQUENCE: 4

Ala Val Tyr Ile Gly Ala Leu Phe Pro Met Ser Gly Gly Trp Pro Gly
 1               5                  10                  15

Gly Gln Ala Cys Gln Pro Ala Val Glu Met Ala Leu Glu Asp Val Asn
            20                  25                  30
```

-continued

```
Ser Arg Arg Asp Ile Leu Pro Asp Tyr Glu Leu Lys Leu Ile His His
         35                  40                  45

Asp Ser Lys Cys Asp Pro Gly Gln Ala Thr Lys Tyr Leu Tyr Glu Leu
         50                  55                  60

Leu Tyr Asn Asp Pro Ile Lys Ile Ile Leu Met Pro Gly Cys Ser Ser
 65                  70                  75                  80

Val Ser Thr Leu Val Ala Glu Ala Ala Arg Met Trp Asn Leu Ile Val
                 85                  90                  95

Leu Ser Tyr Gly Ser Ser Pro Ala Leu Ser Asn Arg Gln Arg Phe
                100                 105                 110

Pro Thr Phe Phe Arg Thr His Pro Ser Ala Thr Leu His Asn Pro Thr
             115                 120                 125

Arg Val Lys Leu Phe Glu Lys Trp Gly Trp Lys Lys Ile Ala Thr Ile
         130                 135                 140

Gln Gln Thr Thr Glu Val Phe Thr Ser Thr Leu Asp Asp Leu Glu Glu
145                 150                 155                 160

Arg Val Lys Glu Ala Gly Ile Glu Ile Thr Phe Arg Gln Ser Phe Phe
                165                 170                 175

Ser Asp Pro Ala Val Pro Val Lys Asn Leu Lys Arg Gln Asp Ala Arg
             180                 185                 190

Ile Ile Val Gly Leu Phe Tyr Glu Thr Glu Ala Arg Lys Val Phe Cys
         195                 200                 205

Glu Val Tyr Lys Glu Arg Leu Phe Gly Lys Lys Tyr Val Trp Phe Leu
         210                 215                 220

Ile Gly Trp Tyr Ala Asp Asn Trp Phe Lys Ile Tyr Asp Pro Ser Ile
225                 230                 235                 240

Asn Cys Thr Val Asp Glu Met Thr Glu Ala Val Glu Gly His Ile Thr
             245                 250                 255

Thr Glu Ile Val Met Leu Asn Pro Ala Asn Thr Arg Ser Ile Ser Asn
             260                 265                 270

Met Thr Ser Gln Glu Phe Val Glu Lys Leu Thr Lys Arg Leu Lys Arg
         275                 280                 285

His Pro Glu Glu Thr Gly Gly Phe Gln Glu Ala Pro Leu Ala Tyr Asp
         290                 295                 300

Ala Ile Trp Ala Leu Ala Leu Ala Leu Asn Lys Thr Ser Gly Gly Gly
305                 310                 315                 320

Gly Arg Ser Gly Val Arg Leu Glu Asp Phe Asn Tyr Asn Asn Gln Thr
             325                 330                 335

Ile Thr Asp Gln Ile Tyr Arg Ala Met Asn Ser Ser Ser Phe Glu Gly
             340                 345                 350

Val Ser Gly His Val Val Phe Asp Ala Ser Gly Ser Arg Met Ala Trp
             355                 360                 365

Thr Leu Ile Glu Gln Leu Gln Gly Gly Ser Tyr Lys Lys Ile Gly Tyr
         370                 375                 380

Tyr Asp Ser Thr Lys Asp Asp Leu Ser Trp Ser Lys Thr Asp Lys Trp
385                 390                 395                 400

Ile Gly Gly Ser Pro Pro Ala Asp Gln Thr Leu Val Ile Lys Thr Phe
             405                 410                 415

Arg Phe Leu Ser Gln Lys Leu Phe Ile Ser Val Ser Val Leu Ser Ser
             420                 425                 430

Leu Gly Ile Val Leu Ala Val Val Cys Leu Ser Phe Asn Ile Tyr Asn
         435                 440                 445
```

-continued

```
Ser His Val Arg Tyr Ile Gln Asn Ser Gln Pro Asn Leu Asn Asn Leu
    450                 455                 460

Thr Ala Val Gly Cys Ser Leu Ala Leu Ala Ala Val Phe Pro Leu Gly
465                 470                 475                 480

Leu Asp Gly Tyr His Ile Gly Arg Asn Gln Phe Pro Phe Val Cys Gln
                    485                 490                 495

Ala Arg Leu Trp Leu Leu Gly Leu Gly Phe Ser Leu Gly Tyr Gly Ser
            500                 505                 510

Met Phe Thr Lys Ile Trp Trp Val His Thr Val Phe Thr Lys Lys Glu
            515                 520                 525

Glu Lys Lys Glu Trp Arg Lys Thr Leu Glu Pro Trp Lys Leu Tyr Ala
530                 535                 540

Thr Val Gly Leu Leu Val Gly Met Asp Val Leu Thr Leu Ala Ile Trp
545                 550                 555                 560

Gln Ile Val Asp Pro Leu His Arg Thr Ile Glu Thr Phe Ala Lys Glu
                565                 570                 575

Glu Pro Lys Glu Asp Ile Asp Val Ser Ile Leu Pro Gln Leu Glu His
            580                 585                 590

Cys Ser Ser Arg Lys Met Asn Thr Trp Leu Gly Ile Phe Tyr Gly Tyr
            595                 600                 605

Lys Gly Leu Leu Leu Leu Leu Gly Ile Phe Leu Ala Tyr Glu Thr Lys
610                 615                 620

Ser Val Ser Thr Glu Lys Ile Asn Asp His Arg Ala Val Gly Met Ala
625                 630                 635                 640

Ile Tyr Asn Val Ala Val Leu Cys Leu Ile Thr Ala Pro Val Thr Met
                645                 650                 655

Ile Leu Ser Ser Gln Gln Asp Ala Ala Phe Ala Phe Ala Ser Leu Ala
            660                 665                 670

Ile Val Phe Ser Ser Tyr Ile Thr Leu Val Val Leu Phe Val Pro Lys
            675                 680                 685

Met Arg Arg Leu Ile Thr Arg Gly Glu Trp Gln Ser Glu Ala Gln Asp
690                 695                 700

Thr Met Lys Thr Gly Ser Ser Thr Asn Asn Asn Glu Glu Glu Lys Ser
705                 710                 715                 720

Arg Leu Leu Glu Lys Glu Asn Arg Glu Leu Glu Lys Ile Ile Ala Glu
                725                 730                 735

Lys Glu Glu Arg Val Ser Glu Leu Arg His Gln Leu Gln Ser Arg Gln
            740                 745                 750

Gln Leu Arg Ser Arg Arg His Pro Pro Thr Pro Pro Glu Pro Ser Gly
            755                 760                 765

Gly Leu Pro Arg Gly Pro Pro Glu Pro Pro Asp Arg Leu Ser Cys Asp
770                 775                 780

Gly Ser Arg Val His Leu Leu Tyr Lys
785                 790

<210> SEQ ID NO 5
<211> LENGTH: 2837
<212> TYPE: DNA
<213> ORGANISM: Rattus norvegicus
<220> FEATURE:
<221> NAME/KEY: CDS
<222> LOCATION: (228)..(2759)
<223> OTHER INFORMATION: Clone: GABABR1b rat
<221> NAME/KEY: mat_peptide
<222> LOCATION: (228)..(2759)
```

```
<400> SEQUENCE: 5
aacggccgcc agtgtgctgg aaagggagag tccgcggtgg cgggagcgaa cgtctcctgg      60
ccctaggaag cccacgtctc tgccttcccc gggctctggc ccctcctccc caatgagacc     120
ggggatggag acacctcccc gacgccctcc cagaagcctt ccccagaaga agtgtccccc     180
ctgagctgcc ccccacccca aggaggccgc ccccgccccc cctcgcc atg ggc ccg        236
                                                   Met Gly Pro
                                                     1 ggg gga ccc tgt acc cca gtg ggg tgg ccg ctg cct ctt ctg ctg gtg        284
Gly Gly Pro Cys Thr Pro Val Gly Trp Pro Leu Pro Leu Leu Leu Val
      5                  10                  15 atg gcg gct ggg gtg gct ccg gtg tgg gcc tct cac tcc cct cat ctc        332
Met Ala Ala Gly Val Ala Pro Val Trp Ala Ser His Ser Pro His Leu
 20                  25                  30                  35 ccg cgg cct cac ccg agg gtc ccc ccg cac ccc tcc tca gaa cgg cgt        380
Pro Arg Pro His Pro Arg Val Pro Pro His Pro Ser Ser Glu Arg Arg
                 40                  45                  50 gca gta tac atc ggg gcg ctg ttt ccc atg agc ggg ggc tgg ccg ggg        428
Ala Val Tyr Ile Gly Ala Leu Phe Pro Met Ser Gly Gly Trp Pro Gly
         55                  60                  65 ggc cag gcc tgc cag ccc gcg gtg gag atg gcg ctg gag gac gtt aac        476
Gly Gln Ala Cys Gln Pro Ala Val Glu Met Ala Leu Glu Asp Val Asn
 70                  75                  80 agc cgc aga gac atc ctg ccg gac tac gag ctc aag ctt atc cac cac        524
Ser Arg Arg Asp Ile Leu Pro Asp Tyr Glu Leu Lys Leu Ile His His
     85                  90                  95 gac agc aag tgt gac cca ggg caa gcc acc aag tac ttg tac gaa cta        572
Asp Ser Lys Cys Asp Pro Gly Gln Ala Thr Lys Tyr Leu Tyr Glu Leu
100                 105                 110                 115 ctc tac aat gac ccc atc aag atc att ctc atg cct ggc tgt agt tct        620
Leu Tyr Asn Asp Pro Ile Lys Ile Ile Leu Met Pro Gly Cys Ser Ser
                 120                 125                 130 gtc tcc aca ctt gta gct gag gct gcc cgg atg tgg aac ctt att gtg        668
Val Ser Thr Leu Val Ala Glu Ala Ala Arg Met Trp Asn Leu Ile Val
        135                 140                 145 ctc tca tat ggc tcc agt tca cca gcc ttg tca aac cga cag cgg ttt        716
Leu Ser Tyr Gly Ser Ser Ser Pro Ala Leu Ser Asn Arg Gln Arg Phe
        150                 155                 160 ccc acg ttc ttc cgg acg cat cca tcc gcc aca ctc cac aat ccc acc        764
Pro Thr Phe Phe Arg Thr His Pro Ser Ala Thr Leu His Asn Pro Thr
165                 170                 175 cgg gtg aaa ctc ttc gaa aag tgg ggc tgg aag aag atc gct acc atc        812
Arg Val Lys Leu Phe Glu Lys Trp Gly Trp Lys Lys Ile Ala Thr Ile
180                 185                 190                 195 caa cag acc acc gag gtc ttc acc tca acg ctg gat gac ctg gag gag        860
Gln Gln Thr Thr Glu Val Phe Thr Ser Thr Leu Asp Asp Leu Glu Glu
                 200                 205                 210 cga gtg aaa gag gct ggg atc gag atc act ttc cga cag agt ttc ttc        908
Arg Val Lys Glu Ala Gly Ile Glu Ile Thr Phe Arg Gln Ser Phe Phe
        215                 220                 225 tcg gat cca gct gtg cct gtt aaa aac ctg aag cgt caa gat gct cga        956
Ser Asp Pro Ala Val Pro Val Lys Asn Leu Lys Arg Gln Asp Ala Arg
        230                 235                 240 atc atc gtg gga ctt ttc tat gag acg gaa gcc cgg aaa gtt ttt tgt       1004
Ile Ile Val Gly Leu Phe Tyr Glu Thr Glu Ala Arg Lys Val Phe Cys
245                 250                 255 gag gtc tat aag gaa agg ctc ttt ggg aag aag tac gtc tgg ttc ctc       1052
Glu Val Tyr Lys Glu Arg Leu Phe Gly Lys Lys Tyr Val Trp Phe Leu
260                 265                 270                 275
```

-continued

| | |
|---|---|
| atc ggg tgg tat gct gac aac tgg ttc aag acc tat gac ccg tca atc<br>Ile Gly Trp Tyr Ala Asp Asn Trp Phe Lys Thr Tyr Asp Pro Ser Ile<br>                 280                       285                   290 | 1100 |
| aat tgt aca gtg gaa gaa atg acc gag gcg gtg gag ggc cac atc acc<br>Asn Cys Thr Val Glu Glu Met Thr Glu Ala Val Glu Gly His Ile Thr<br>                 295                       300                   305 | 1148 |
| acg gag att gtc atg ctg aac cct gcc aac acc cga agc att tcc aac<br>Thr Glu Ile Val Met Leu Asn Pro Ala Asn Thr Arg Ser Ile Ser Asn<br>       310                     315                       320 | 1196 |
| atg acg tca cag gaa ttt gtg gag aaa cta acc aag cgg ctg aaa aga<br>Met Thr Ser Gln Glu Phe Val Glu Lys Leu Thr Lys Arg Leu Lys Arg<br>325                       330                       335 | 1244 |
| cac ccc gag gag act gga ggc ttc cag gag gca cca ctg gcc tat gat<br>His Pro Glu Glu Thr Gly Gly Phe Gln Glu Ala Pro Leu Ala Tyr Asp<br>340                       345                     350                   355 | 1292 |
| gct atc tgg gcc ttg gct ttg gcc ttg aac aag acg tct gga gga ggt<br>Ala Ile Trp Ala Leu Ala Leu Ala Leu Asn Lys Thr Ser Gly Gly Gly<br>                 360                       365                   370 | 1340 |
| ggt cgt tcc ggc gtg cgc ctg gag gac ttt aac tac aac aac cag acc<br>Gly Arg Ser Gly Val Arg Leu Glu Asp Phe Asn Tyr Asn Asn Gln Thr<br>                 375                       380                   385 | 1388 |
| att aca gac cag atc tac cgg gcc atg aac tcc tcc tcc ttt gag ggc<br>Ile Thr Asp Gln Ile Tyr Arg Ala Met Asn Ser Ser Ser Phe Glu Gly<br>       390                     395                       400 | 1436 |
| gtt tct ggc cat gtg gtc ttt gat gcc agc ggc tcc cgg atg gca tgg<br>Val Ser Gly His Val Val Phe Asp Ala Ser Gly Ser Arg Met Ala Trp<br>405                       410                     415 | 1484 |
| aca ctt atc gag cag cta cag ggc ggc agc tac aag aag atc ggc tac<br>Thr Leu Ile Glu Gln Leu Gln Gly Gly Ser Tyr Lys Lys Ile Gly Tyr<br>420                       425                     430                   435 | 1532 |
| tac gac agc acc aag gat gat ctt tcc tgg tcc aaa acg gac aag tgg<br>Tyr Asp Ser Thr Lys Asp Asp Leu Ser Trp Ser Lys Thr Asp Lys Trp<br>                 440                       445                   450 | 1580 |
| att gga ggg tct ccc cca gct gac cag acc ttg gtc atc aag aca ttc<br>Ile Gly Gly Ser Pro Pro Ala Asp Gln Thr Leu Val Ile Lys Thr Phe<br>                 455                       460                   465 | 1628 |
| cgt ttc ctg tct cag aaa ctc ttt atc tcc gtc tca gtt ctc tcc agc<br>Arg Phe Leu Ser Gln Lys Leu Phe Ile Ser Val Ser Val Leu Ser Ser<br>                 470                       475                   480 | 1676 |
| ctg ggc att gtt ctt gct gtt gtc tgt ctg tcc ttt aac atc tac aac<br>Leu Gly Ile Val Leu Ala Val Val Cys Leu Ser Phe Asn Ile Tyr Asn<br>485                       490                     495 | 1724 |
| tcc cac gtt cgt tat atc cag aac tcc cag ccc aac ctg aac aat ctg<br>Ser His Val Arg Tyr Ile Gln Asn Ser Gln Pro Asn Leu Asn Asn Leu<br>500                       505                     510                   515 | 1772 |
| act gct gtg ggc tgc tca ctg gca ctg gct gct gtc ttc cct ctc ggg<br>Thr Ala Val Gly Cys Ser Leu Ala Leu Ala Ala Val Phe Pro Leu Gly<br>                 520                       525                   530 | 1820 |
| ctg gat ggt tac cac ata ggg aga agc cag ttc ccg ttt gtc tgc cag<br>Leu Asp Gly Tyr His Ile Gly Arg Ser Gln Phe Pro Phe Val Cys Gln<br>                 535                       540                   545 | 1868 |
| gcc cgc ctt tgg ctc ttg ggc ttg ggc ttt agt ctg ggc tat ggc tct<br>Ala Arg Leu Trp Leu Leu Gly Leu Gly Phe Ser Leu Gly Tyr Gly Ser<br>       550                     555                       560 | 1916 |
| atg ttc acc aag atc tgg tgg gtc cac aca gtc ttc acg aag aag gag<br>Met Phe Thr Lys Ile Trp Trp Val His Thr Val Phe Thr Lys Lys Glu<br>565                       570                     575 | 1964 |
| gag aag aag gag tgg agg aag acc cta gag ccc tgg aaa ctc tat gcc<br>Glu Lys Lys Glu Trp Arg Lys Thr Leu Glu Pro Trp Lys Leu Tyr Ala<br>580                       585                     590                   595 | 2012 |

-continued

```
act gtg ggc ctg ctg gtg ggc atg gat gtc ctg act ctt gcc atc tgg    2060
Thr Val Gly Leu Leu Val Gly Met Asp Val Leu Thr Leu Ala Ile Trp
            600                 605                 610 cag att gtg gac ccc ttg cac cga acc att gag act ttt gcc aag gag    2108
Gln Ile Val Asp Pro Leu His Arg Thr Ile Glu Thr Phe Ala Lys Glu
        615                 620                 625 gaa cca aag gaa gac atc gat gtc tcc att ctg ccc cag ttg gag cac    2156
Glu Pro Lys Glu Asp Ile Asp Val Ser Ile Leu Pro Gln Leu Glu His
    630                 635                 640 tgc agc tcc aag aag atg aat acg tgg ctt ggc att ttc tat ggt tac    2204
Cys Ser Ser Lys Lys Met Asn Thr Trp Leu Gly Ile Phe Tyr Gly Tyr
645                 650                 655 aag ggg ctg ctg ctg ctg ctg gga atc ttt ctt gct tac gaa acc aag    2252
Lys Gly Leu Leu Leu Leu Leu Gly Ile Phe Leu Ala Tyr Glu Thr Lys
660                 665                 670                 675 agc gtg tcc act gaa aag atc aat gac cac agg gcc gtg ggc atg gct    2300
Ser Val Ser Thr Glu Lys Ile Asn Asp His Arg Ala Val Gly Met Ala
                680                 685                 690 atc tac aat gtc gcg gtc ctg tgt ctc atc act gct cct gtg acc atg    2348
Ile Tyr Asn Val Ala Val Leu Cys Leu Ile Thr Ala Pro Val Thr Met
            695                 700                 705 atc ctt tcc agt cag cag gac gca gcc ttt gcc ttt gcc tct ctg gcc    2396
Ile Leu Ser Ser Gln Gln Asp Ala Ala Phe Ala Phe Ala Ser Leu Ala
        710                 715                 720 atc gtg ttc tct tcc tac atc act ctg gtt gtg ctc ttt gtg ccc aag    2444
Ile Val Phe Ser Ser Tyr Ile Thr Leu Val Val Leu Phe Val Pro Lys
    725                 730                 735 atg cgc agg ctg atc acc cga ggg gaa tgg cag tct gaa acg cag gac    2492
Met Arg Arg Leu Ile Thr Arg Gly Glu Trp Gln Ser Glu Thr Gln Asp
740                 745                 750                 755 acc atg aaa aca gga tca tcc acc aac aac aac gag gaa gag aag tcc    2540
Thr Met Lys Thr Gly Ser Ser Thr Asn Asn Asn Glu Glu Glu Lys Ser
                760                 765                 770 cga ctg ttg gag aag gaa aac cga gaa ctg gaa aag atc atc gct gag    2588
Arg Leu Leu Glu Lys Glu Asn Arg Glu Leu Glu Lys Ile Ile Ala Glu
            775                 780                 785 aaa gag gag cgc gtc tct gaa ctg cgc cat cag ctc cag tct cgg cag    2636
Lys Glu Glu Arg Val Ser Glu Leu Arg His Gln Leu Gln Ser Arg Gln
        790                 795                 800 caa ctc cgc tca cgg cgc cac ccc cca aca ccc cca gat ccc tct ggg    2684
Gln Leu Arg Ser Arg Arg His Pro Pro Thr Pro Pro Asp Pro Ser Gly
    805                 810                 815 ggc ctt ccc agg gga ccc tct gag ccc cct gac cgg ctt agc tgt gat    2732
Gly Leu Pro Arg Gly Pro Ser Glu Pro Pro Asp Arg Leu Ser Cys Asp
820                 825                 830                 835 ggg agt cga gta cat ttg ctt tac aag tgaggggca tggagaagga           2779
Gly Ser Arg Val His Leu Leu Tyr Lys
                840 tctccctgaa tctcaataaa gcagtgaaca gtaaactttc agcacactg gcggccgc    2837

<210> SEQ ID NO 6
<211> LENGTH: 844
<212> TYPE: PRT
<213> ORGANISM: Rattus norvegicus

<400> SEQUENCE: 6

Met Gly Pro Gly Gly Pro Cys Thr Pro Val Gly Trp Pro Leu Pro Leu
 1               5                  10                  15

Leu Leu Val Met Ala Ala Gly Val Ala Pro Val Trp Ala Ser His Ser
            20                  25                  30
```

-continued

```
Pro His Leu Pro Arg Pro His Pro Arg Val Pro Pro His Pro Ser Ser
        35                  40                  45

Glu Arg Arg Ala Val Tyr Ile Gly Ala Leu Phe Pro Met Ser Gly Gly
    50                  55                  60

Trp Pro Gly Gly Gln Ala Cys Gln Pro Ala Val Glu Met Ala Leu Glu
65                  70                  75                  80

Asp Val Asn Ser Arg Arg Asp Ile Leu Pro Asp Tyr Glu Leu Lys Leu
                85                  90                  95

Ile His His Asp Ser Lys Cys Asp Pro Gly Gln Ala Thr Lys Tyr Leu
                100                 105                 110

Tyr Glu Leu Leu Tyr Asn Asp Pro Ile Lys Ile Leu Met Pro Gly
    115                 120                 125

Cys Ser Ser Val Ser Thr Leu Val Ala Glu Ala Arg Met Trp Asn
130                 135                 140

Leu Ile Val Leu Ser Tyr Gly Ser Ser Pro Ala Leu Ser Asn Arg
145                 150                 155                 160

Gln Arg Phe Pro Thr Phe Phe Arg Thr His Pro Ser Ala Thr Leu His
                165                 170                 175

Asn Pro Thr Arg Val Lys Leu Phe Glu Lys Trp Gly Trp Lys Lys Ile
                180                 185                 190

Ala Thr Ile Gln Gln Thr Thr Glu Val Phe Thr Ser Thr Leu Asp Asp
    195                 200                 205

Leu Glu Glu Arg Val Lys Glu Ala Gly Ile Glu Ile Thr Phe Arg Gln
    210                 215                 220

Ser Phe Phe Ser Asp Pro Ala Val Pro Val Lys Asn Leu Lys Arg Gln
225                 230                 235                 240

Asp Ala Arg Ile Ile Val Gly Leu Phe Tyr Glu Thr Glu Ala Arg Lys
                245                 250                 255

Val Phe Cys Glu Val Tyr Lys Glu Arg Leu Phe Gly Lys Lys Tyr Val
                260                 265                 270

Trp Phe Leu Ile Gly Trp Tyr Ala Asp Asn Trp Phe Lys Thr Tyr Asp
    275                 280                 285

Pro Ser Ile Asn Cys Thr Val Glu Glu Met Thr Glu Ala Val Glu Gly
    290                 295                 300

His Ile Thr Thr Glu Ile Val Met Leu Asn Pro Ala Asn Thr Arg Ser
305                 310                 315                 320

Ile Ser Asn Met Thr Ser Gln Glu Phe Val Glu Lys Leu Thr Lys Arg
                325                 330                 335

Leu Lys Arg His Pro Glu Glu Thr Gly Gly Phe Gln Glu Ala Pro Leu
                340                 345                 350

Ala Tyr Asp Ala Ile Trp Ala Leu Ala Leu Ala Leu Asn Lys Thr Ser
    355                 360                 365

Gly Gly Gly Gly Arg Ser Gly Val Arg Leu Glu Asp Phe Asn Tyr Asn
    370                 375                 380

Asn Gln Thr Ile Thr Asp Gln Ile Tyr Arg Ala Met Asn Ser Ser Ser
385                 390                 395                 400

Phe Glu Gly Val Ser Gly His Val Val Phe Asp Ala Ser Gly Ser Arg
                405                 410                 415

Met Ala Trp Thr Leu Ile Glu Gln Leu Gln Gly Gly Ser Tyr Lys Lys
                420                 425                 430

Ile Gly Tyr Tyr Asp Ser Thr Lys Asp Asp Leu Ser Trp Ser Lys Thr
    435                 440                 445
```

```
Asp Lys Trp Ile Gly Gly Ser Pro Pro Ala Asp Gln Thr Leu Val Ile
    450                 455                 460

Lys Thr Phe Arg Phe Leu Ser Gln Lys Leu Phe Ile Ser Val Ser Val
465                 470                 475                 480

Leu Ser Ser Leu Gly Ile Val Leu Ala Val Val Cys Leu Ser Phe Asn
                    485                 490                 495

Ile Tyr Asn Ser His Val Arg Tyr Ile Gln Asn Ser Gln Pro Asn Leu
                500                 505                 510

Asn Asn Leu Thr Ala Val Gly Cys Ser Leu Ala Leu Ala Ala Val Phe
            515                 520                 525

Pro Leu Gly Leu Asp Gly Tyr His Ile Gly Arg Ser Gln Phe Pro Phe
        530                 535                 540

Val Cys Gln Ala Arg Leu Trp Leu Leu Gly Leu Gly Phe Ser Leu Gly
545                 550                 555                 560

Tyr Gly Ser Met Phe Thr Lys Ile Trp Trp Val His Thr Val Phe Thr
                565                 570                 575

Lys Lys Glu Glu Lys Lys Glu Trp Arg Lys Thr Leu Glu Pro Trp Lys
                580                 585                 590

Leu Tyr Ala Thr Val Gly Leu Leu Val Gly Met Asp Val Leu Thr Leu
        595                 600                 605

Ala Ile Trp Gln Ile Val Asp Pro Leu His Arg Thr Ile Glu Thr Phe
610                 615                 620

Ala Lys Glu Glu Pro Lys Glu Asp Ile Asp Val Ser Ile Leu Pro Gln
625                 630                 635                 640

Leu Glu His Cys Ser Ser Lys Lys Met Asn Thr Trp Leu Gly Ile Phe
                645                 650                 655

Tyr Gly Tyr Lys Gly Leu Leu Leu Leu Gly Ile Phe Leu Ala Tyr
                660                 665                 670

Glu Thr Lys Ser Val Ser Thr Glu Lys Ile Asn Asp His Arg Ala Val
        675                 680                 685

Gly Met Ala Ile Tyr Asn Val Ala Val Leu Cys Leu Ile Thr Ala Pro
        690                 695                 700

Val Thr Met Ile Leu Ser Ser Gln Gln Asp Ala Ala Phe Ala Phe Ala
705                 710                 715                 720

Ser Leu Ala Ile Val Phe Ser Ser Tyr Ile Thr Leu Val Val Leu Phe
                725                 730                 735

Val Pro Lys Met Arg Arg Leu Ile Thr Arg Gly Glu Trp Gln Ser Glu
                740                 745                 750

Thr Gln Asp Thr Met Lys Thr Gly Ser Ser Thr Asn Asn Asn Glu Glu
            755                 760                 765

Glu Lys Ser Arg Leu Leu Glu Lys Glu Asn Arg Glu Leu Glu Lys Ile
        770                 775                 780

Ile Ala Glu Lys Glu Glu Arg Val Ser Glu Leu Arg His Gln Leu Gln
785                 790                 795                 800

Ser Arg Gln Gln Leu Arg Ser Arg Arg His Pro Thr Pro Pro Asp
                805                 810                 815

Pro Ser Gly Gly Leu Pro Arg Gly Pro Ser Glu Pro Pro Asp Arg Leu
        820                 825                 830

Ser Cys Asp Gly Ser Arg Val His Leu Leu Tyr Lys
            835                 840
```

```
<210> SEQ ID NO 7
<211> LENGTH: 3101
<212> TYPE: DNA
<213> ORGANISM: Homo sapiens
<220> FEATURE:
<221> NAME/KEY: CDS
<222> LOCATION: (169)..(2700)
<223> OTHER INFORMATION: Clone: GABABR1b human
<221> NAME/KEY: mat_peptide
<222> LOCATION: (169)..(2700)

<400> SEQUENCE: 7
ggccgtagga agccaacctt ccctgcttct ccggggccct cgccccctcc tccccacaaa        60
atcagggatg gaggcgcctc cccggcaccc tcttagcagc cctccccagg aaaagtgtcc       120
cccctgagct cctaacgctc cccaacagct accctgccc ccacgcc atg ggg ccc          177
                                                 Met Gly Pro
                                                   1 ggg gcc cct ttt gcc cgg gtg ggg tgg cca ctg ccg ctt ctg gtt gtg         225
Gly Ala Pro Phe Ala Arg Val Gly Trp Pro Leu Pro Leu Leu Val Val
         5                  10                  15 atg gcg gca ggg gtg gct ccg gtg tgg gcc tcc cac tcc ccc cat ctc         273
Met Ala Ala Gly Val Ala Pro Val Trp Ala Ser His Ser Pro His Leu
 20                  25                  30                  35 ccg cgg cct cac tcg cgg gtc ccc ccg cac ccc tcc tca gaa cgg cgc         321
Pro Arg Pro His Ser Arg Val Pro Pro His Pro Ser Ser Glu Arg Arg
                 40                  45                  50 gca gtg tac atc ggg gca ctg ttt ccc atg agc ggg ggc tgg cca ggg         369
Ala Val Tyr Ile Gly Ala Leu Phe Pro Met Ser Gly Gly Trp Pro Gly
             55                  60                  65 ggc cag gcc tgc cag ccc gcg gtg gag atg gcg ctg gag gac gtg aat         417
Gly Gln Ala Cys Gln Pro Ala Val Glu Met Ala Leu Glu Asp Val Asn
         70                  75                  80 agc cgc agg gac atc ctg ccg gac tat gag ctc aag ctc atc cac cac         465
Ser Arg Arg Asp Ile Leu Pro Asp Tyr Glu Leu Lys Leu Ile His His
 85                  90                  95 gac agc aag tgt gat cca ggc caa gcc acc aag tac cta tat gag ctg         513
Asp Ser Lys Cys Asp Pro Gly Gln Ala Thr Lys Tyr Leu Tyr Glu Leu
100                 105                 110                 115 ctc tac aac gac cct atc aag atc atc ctt atg cct ggc tgc agc tct         561
Leu Tyr Asn Asp Pro Ile Lys Ile Ile Leu Met Pro Gly Cys Ser Ser
                120                 125                 130 gtc tcc acg ctg gtg gct gag gct gct agg atg tgg aac ctc att gtg         609
Val Ser Thr Leu Val Ala Glu Ala Ala Arg Met Trp Asn Leu Ile Val
            135                 140                 145 ctt tcc tat ggc tcc agc tca cca gcc ctg tca aac cgg cag cgt ttc         657
Leu Ser Tyr Gly Ser Ser Ser Pro Ala Leu Ser Asn Arg Gln Arg Phe
        150                 155                 160 ccc act ttc ttc cga acg cac cca tca gcc aca ctc cac aac cct acc         705
Pro Thr Phe Phe Arg Thr His Pro Ser Ala Thr Leu His Asn Pro Thr
    165                 170                 175 cgc gtg aaa ctc ttt gaa aag tgg ggc tgg aag aag att gct acc atc         753
Arg Val Lys Leu Phe Glu Lys Trp Gly Trp Lys Lys Ile Ala Thr Ile
180                 185                 190                 195 cag cag acc act gag gtc ttc act tcg act ctg gac gac ctg gag gaa         801
Gln Gln Thr Thr Glu Val Phe Thr Ser Thr Leu Asp Asp Leu Glu Glu
                200                 205                 210 cga gtg aag gag gct gga att gag att act ttc cgc cag agt ttc ttc         849
Arg Val Lys Glu Ala Gly Ile Glu Ile Thr Phe Arg Gln Ser Phe Phe
            215                 220                 225
```

```
tca gat cca gct gtg ccc gtc aaa aac ctg aag cgc cag gat gcc cga    897
Ser Asp Pro Ala Val Pro Val Lys Asn Leu Lys Arg Gln Asp Ala Arg
        230                 235                 240 atc atc gtg gga ctt ttc tat gag act gaa gcc cgg aaa gtt ttt tgt    945
Ile Ile Val Gly Leu Phe Tyr Glu Thr Glu Ala Arg Lys Val Phe Cys
245                 250                 255 gag gtg tac aag gag cgt ctc ttt ggg aag aag tac gtc tgg ttc ctc    993
Glu Val Tyr Lys Glu Arg Leu Phe Gly Lys Lys Tyr Val Trp Phe Leu
260                 265                 270                 275 att ggg tgg tat gct gac aat tgg ttc aag atc tac gac cct tct atc   1041
Ile Gly Trp Tyr Ala Asp Asn Trp Phe Lys Ile Tyr Asp Pro Ser Ile
                280                 285                 290 aac tgc aca gtg gat gag atg act gag gcg gtg gag ggc cac atc aca   1089
Asn Cys Thr Val Asp Glu Met Thr Glu Ala Val Glu Gly His Ile Thr
        295                 300                 305 act gag att gtc atg ctg aat cct gcc aat acc cgc agc att tcc aac   1137
Thr Glu Ile Val Met Leu Asn Pro Ala Asn Thr Arg Ser Ile Ser Asn
310                 315                 320 atg aca tcc cag gaa ttt gtg gag aaa cta acc aag cga ctg aaa aga   1185
Met Thr Ser Gln Glu Phe Val Glu Lys Leu Thr Lys Arg Leu Lys Arg
325                 330                 335 cac cct gag gag aca gga ggc ttc cag gag gca ccg ctg gcc tat gat   1233
His Pro Glu Glu Thr Gly Gly Phe Gln Glu Ala Pro Leu Ala Tyr Asp
340                 345                 350                 355 gcc atc tgg gcc ttg gca ctg gcc ctg aac aag aca tct gga gga ggc   1281
Ala Ile Trp Ala Leu Ala Leu Ala Leu Asn Lys Thr Ser Gly Gly Gly
                360                 365                 370 ggc cgt tct ggt gtg cgc ctg gag gac ttc aac tac aac aac cag acc   1329
Gly Arg Ser Gly Val Arg Leu Glu Asp Phe Asn Tyr Asn Asn Gln Thr
        375                 380                 385 att acc gac caa atc tac cgg gca atg aac tct tcg tcc ttt gag ggt   1377
Ile Thr Asp Gln Ile Tyr Arg Ala Met Asn Ser Ser Ser Phe Glu Gly
390                 395                 400 gtc tct ggc cat gtg gtg ttt gat gcc agc ggc tct cgg atg gca tgg   1425
Val Ser Gly His Val Val Phe Asp Ala Ser Gly Ser Arg Met Ala Trp
405                 410                 415 acg ctt atc gag cag ctt cag ggt ggc agc tac aag aag att ggc tac   1473
Thr Leu Ile Glu Gln Leu Gln Gly Gly Ser Tyr Lys Lys Ile Gly Tyr
420                 425                 430                 435 tat gac agc acc aag gat gat ctt tcc tgg tca aaa aca gat aaa tgg   1521
Tyr Asp Ser Thr Lys Asp Asp Leu Ser Trp Ser Lys Thr Asp Lys Trp
                440                 445                 450 att gga ggg tcc ccc cca gct gac cag acc ctg gtc atc aag aca ttc   1569
Ile Gly Gly Ser Pro Pro Ala Asp Gln Thr Leu Val Ile Lys Thr Phe
        455                 460                 465 cgc ttc ctg tca cag aaa ctc ttt atc tcc gtc tca gtt ctc tcc agc   1617
Arg Phe Leu Ser Gln Lys Leu Phe Ile Ser Val Ser Val Leu Ser Ser
470                 475                 480 ctg ggc att gtc cta gct gtt gtc tgt ctg tcc ttt aac atc tac aac   1665
Leu Gly Ile Val Leu Ala Val Val Cys Leu Ser Phe Asn Ile Tyr Asn
485                 490                 495 tca cat gtc cgt tat atc cag aac tca cag ccc aac ctg aac aac ctg   1713
Ser His Val Arg Tyr Ile Gln Asn Ser Gln Pro Asn Leu Asn Asn Leu
500                 505                 510                 515 act gct gtg ggc tgc tca ctg gct tta gct gct gtc ttc ccc ctg ggg   1761
Thr Ala Val Gly Cys Ser Leu Ala Leu Ala Ala Val Phe Pro Leu Gly
                520                 525                 530 ctc gat ggt tac cac att ggg agg aac cag ttt cct ttc gtc tgc cag   1809
Leu Asp Gly Tyr His Ile Gly Arg Asn Gln Phe Pro Phe Val Cys Gln
        535                 540                 545
```

```
gcc cgc ctc tgg ctc ctg ggc ctg ggc ttt agt ctg ggc tac ggt tcc    1857
Ala Arg Leu Trp Leu Leu Gly Leu Gly Phe Ser Leu Gly Tyr Gly Ser
        550                 555                 560 atg ttc acc aag att tgg tgg gtc cac acg gtc ttc aca aag aag gaa    1905
Met Phe Thr Lys Ile Trp Trp Val His Thr Val Phe Thr Lys Lys Glu
565                 570                 575 gaa aag aag gag tgg agg aag act ctg gaa ccc tgg aag ctg tat gcc    1953
Glu Lys Lys Glu Trp Arg Lys Thr Leu Glu Pro Trp Lys Leu Tyr Ala
580                 585                 590                 595 aca gtg ggc ctg ctg gtg ggc atg gat gtc ctc act ctc gcc atc tgg    2001
Thr Val Gly Leu Leu Val Gly Met Asp Val Leu Thr Leu Ala Ile Trp
                600                 605                 610 cag atc gtg gac cct ctg cac cgg acc att gag aca ttt gcc aag gag    2049
Gln Ile Val Asp Pro Leu His Arg Thr Ile Glu Thr Phe Ala Lys Glu
            615                 620                 625 gaa cct aag gaa gat att gac gtc tct att ctg ccc cag ctg gag cat    2097
Glu Pro Lys Glu Asp Ile Asp Val Ser Ile Leu Pro Gln Leu Glu His
        630                 635                 640 tgc agc tcc agg aag atg aat aca tgg ctt ggc att ttc tat ggt tac    2145
Cys Ser Ser Arg Lys Met Asn Thr Trp Leu Gly Ile Phe Tyr Gly Tyr
645                 650                 655 aag ggg ctg ctg ctg ctg ctg gga atc ttc ctt gct tat gag acc aag    2193
Lys Gly Leu Leu Leu Leu Leu Gly Ile Phe Leu Ala Tyr Glu Thr Lys
660                 665                 670                 675 agt gtg tcc act gag aag atc aat gat cac cgg gct gtg ggc atg gct    2241
Ser Val Ser Thr Glu Lys Ile Asn Asp His Arg Ala Val Gly Met Ala
                680                 685                 690 atc tac aat gtg gca gtc ctg tgc ctc atc act gct cct gtc acc atg    2289
Ile Tyr Asn Val Ala Val Leu Cys Leu Ile Thr Ala Pro Val Thr Met
            695                 700                 705 att ctg tcc agc cag cag gat gca gcc ttt gcc ttt gcc tct ctt gcc    2337
Ile Leu Ser Ser Gln Gln Asp Ala Ala Phe Ala Phe Ala Ser Leu Ala
        710                 715                 720 ata gtt ttc tcc tcc tat atc act ctt gtt gtg ctc ttt gtg ccc aag    2385
Ile Val Phe Ser Ser Tyr Ile Thr Leu Val Val Leu Phe Val Pro Lys
725                 730                 735 atg cgc agg ctg atc acc cga ggg gaa tgg cag tcg gag gcg cag gac    2433
Met Arg Arg Leu Ile Thr Arg Gly Glu Trp Gln Ser Glu Ala Gln Asp
740                 745                 750                 755 acc atg aag aca ggg tca tcg acc aac aac aac gag gag gag aag tcc    2481
Thr Met Lys Thr Gly Ser Ser Thr Asn Asn Asn Glu Glu Glu Lys Ser
                760                 765                 770 cgg ctg ttg gag aag gag aac cgt gaa ctg gaa aag atc att gct gag    2529
Arg Leu Leu Glu Lys Glu Asn Arg Glu Leu Glu Lys Ile Ile Ala Glu
            775                 780                 785 aaa gag gag cgt gtc tct gaa ctg cgc cat caa ctc cag tct cgg cag    2577
Lys Glu Glu Arg Val Ser Glu Leu Arg His Gln Leu Gln Ser Arg Gln
        790                 795                 800 cag ctc cgc tcc cgg cgc cac cca ccg aca ccc cca gaa ccc tct ggg    2625
Gln Leu Arg Ser Arg Arg His Pro Pro Thr Pro Pro Glu Pro Ser Gly
805                 810                 815 ggc ctg ccc agg gga ccc cct gag ccc ccc gac cgg ctt agc tgt gat    2673
Gly Leu Pro Arg Gly Pro Pro Glu Pro Pro Asp Arg Leu Ser Cys Asp
820                 825                 830                 835 ggg agt cga gtg cat ttg ctt tat aag tgagggtagg gtgagggagg          2720
Gly Ser Arg Val His Leu Leu Tyr Lys
                840 acaggccagt aggggagggg aaagggagag gggaagggca gggactcag gaagcagggg   2780 gtccccatcc ccagctggga agaacatgct atccaatctc atctcttgta aatacatgtc  2840
```

-continued

```
cccctgtgag ttctgggctg atttgggtct ctcatacctc tgggaaacag accttttct    2900 ctcttactgc ttcatgtaat tttgtcagaa ggaagaagaa agagggaca acgatgctaa    2960 agattattga ttttagtaa gtacggactt agttattttg gaaaaaatgg gggttaggag    3020
atgggttgga ttgactagca aaggcaggg gttttatggt attactgggg attagaacta    3080
taaaaattga ttgtatgggc g                                             3101
```

<210> SEQ ID NO 8
<211> LENGTH: 844
<212> TYPE: PRT
<213> ORGANISM: Homo sapiens

<400> SEQUENCE: 8

```
Met Gly Pro Gly Ala Pro Phe Ala Arg Val Gly Trp Pro Leu Pro Leu
 1               5                  10                  15

Leu Val Val Met Ala Ala Gly Val Ala Pro Val Trp Ala Ser His Ser
            20                  25                  30

Pro His Leu Pro Arg Pro His Ser Arg Val Pro Pro His Pro Ser Ser
        35                  40                  45

Glu Arg Arg Ala Val Tyr Ile Gly Ala Leu Phe Pro Met Ser Gly Gly
    50                  55                  60

Trp Pro Gly Gly Gln Ala Cys Gln Pro Ala Val Glu Met Ala Leu Glu
65                  70                  75                  80

Asp Val Asn Ser Arg Arg Asp Ile Leu Pro Asp Tyr Glu Leu Lys Leu
                85                  90                  95

Ile His His Asp Ser Lys Cys Asp Pro Gly Gln Ala Thr Lys Tyr Leu
            100                 105                 110

Tyr Glu Leu Leu Tyr Asn Asp Pro Ile Lys Ile Ile Leu Met Pro Gly
        115                 120                 125

Cys Ser Ser Val Ser Thr Leu Val Ala Glu Ala Ala Arg Met Trp Asn
    130                 135                 140

Leu Ile Val Leu Ser Tyr Gly Ser Ser Ser Pro Ala Leu Ser Asn Arg
145                 150                 155                 160

Gln Arg Phe Pro Thr Phe Phe Arg Thr His Pro Ser Ala Thr Leu His
                165                 170                 175

Asn Pro Thr Arg Val Lys Leu Phe Glu Lys Trp Gly Trp Lys Lys Ile
            180                 185                 190

Ala Thr Ile Gln Gln Thr Thr Glu Val Phe Thr Ser Thr Leu Asp Asp
        195                 200                 205

Leu Glu Glu Arg Val Lys Glu Ala Gly Ile Glu Ile Thr Phe Arg Gln
    210                 215                 220

Ser Phe Phe Ser Asp Pro Ala Val Pro Val Lys Asn Leu Lys Arg Gln
225                 230                 235                 240

Asp Ala Arg Ile Ile Val Gly Leu Phe Tyr Glu Thr Glu Ala Arg Lys
                245                 250                 255

Val Phe Cys Glu Val Tyr Lys Glu Arg Leu Phe Gly Lys Lys Tyr Val
            260                 265                 270

Trp Phe Leu Ile Gly Trp Tyr Ala Asp Asn Trp Phe Lys Ile Tyr Asp
        275                 280                 285

Pro Ser Ile Asn Cys Thr Val Asp Glu Met Thr Glu Ala Val Glu Gly
    290                 295                 300

His Ile Thr Thr Glu Ile Val Met Leu Asn Pro Ala Asn Thr Arg Ser
305                 310                 315                 320
```

```
Ile Ser Asn Met Thr Ser Gln Glu Phe Val Glu Lys Leu Thr Lys Arg
            325                 330                 335

Leu Lys Arg His Pro Glu Thr Gly Phe Gln Glu Ala Pro Leu
            340                 345                 350

Ala Tyr Asp Ala Ile Trp Ala Leu Ala Leu Ala Leu Asn Lys Thr Ser
            355                 360                 365

Gly Gly Gly Arg Ser Gly Val Arg Leu Glu Asp Phe Asn Tyr Asn
            370                 375                 380

Asn Gln Thr Ile Thr Asp Gln Ile Tyr Arg Ala Met Asn Ser Ser Ser
385                 390                 395                 400

Phe Glu Gly Val Ser Gly His Val Val Phe Asp Ala Ser Gly Ser Arg
                405                 410                 415

Met Ala Trp Thr Leu Ile Glu Gln Leu Gln Gly Gly Ser Tyr Lys Lys
            420                 425                 430

Ile Gly Tyr Tyr Asp Ser Thr Lys Asp Leu Ser Trp Ser Lys Thr
            435                 440                 445

Asp Lys Trp Ile Gly Gly Ser Pro Ala Asp Gln Thr Leu Val Ile
    450                 455                 460

Lys Thr Phe Arg Phe Leu Ser Gln Lys Leu Phe Ile Ser Val Ser Val
465                 470                 475                 480

Leu Ser Ser Leu Gly Ile Val Leu Ala Val Val Cys Leu Ser Phe Asn
                485                 490                 495

Ile Tyr Asn Ser His Val Arg Tyr Ile Gln Asn Ser Gln Pro Asn Leu
            500                 505                 510

Asn Asn Leu Thr Ala Val Gly Cys Ser Leu Ala Leu Ala Ala Val Phe
            515                 520                 525

Pro Leu Gly Leu Asp Gly Tyr His Ile Gly Arg Asn Gln Phe Pro Phe
            530                 535                 540

Val Cys Gln Ala Arg Leu Trp Leu Leu Gly Leu Gly Phe Ser Leu Gly
545                 550                 555                 560

Tyr Gly Ser Met Phe Thr Lys Ile Trp Trp Val His Thr Val Phe Thr
                565                 570                 575

Lys Lys Glu Glu Lys Lys Glu Trp Arg Lys Thr Leu Glu Pro Trp Lys
            580                 585                 590

Leu Tyr Ala Thr Val Gly Leu Leu Val Gly Met Asp Val Leu Thr Leu
            595                 600                 605

Ala Ile Trp Gln Ile Val Asp Pro Leu His Arg Thr Ile Glu Thr Phe
            610                 615                 620

Ala Lys Glu Glu Pro Lys Glu Asp Ile Asp Val Ser Ile Leu Pro Gln
625                 630                 635                 640

Leu Glu His Cys Ser Ser Arg Lys Met Asn Thr Trp Leu Gly Ile Phe
                645                 650                 655

Tyr Gly Tyr Lys Gly Leu Leu Leu Leu Gly Ile Phe Leu Ala Tyr
            660                 665                 670

Glu Thr Lys Ser Val Ser Thr Glu Lys Ile Asn Asp His Arg Ala Val
            675                 680                 685

Gly Met Ala Ile Tyr Asn Val Ala Val Leu Cys Leu Ile Thr Ala Pro
            690                 695                 700

Val Thr Met Ile Leu Ser Ser Gln Gln Asp Ala Ala Phe Ala Phe Ala
705                 710                 715                 720

Ser Leu Ala Ile Val Phe Ser Ser Tyr Ile Thr Leu Val Val Leu Phe
                725                 730                 735
```

|   |   |   |   |   |   |   |   |   |   |   |   |
|---|---|---|---|---|---|---|---|---|---|---|---|
-continued

| Val | Pro | Lys | Met | Arg | Arg | Leu | Ile | Thr | Arg | Gly | Glu | Trp | Gln | Ser | Glu |
|     |     |     | 740 |     |     |     |     | 745 |     |     |     | 750 |     |     |     |

| Ala | Gln | Asp | Thr | Met | Lys | Thr | Gly | Ser | Ser | Thr | Asn | Asn | Asn | Glu | Glu |
|     |     | 755 |     |     |     |     | 760 |     |     |     |     | 765 |     |     |     |

| Glu | Lys | Ser | Arg | Leu | Leu | Glu | Lys | Glu | Asn | Arg | Glu | Leu | Glu | Lys | Ile |
|     | 770 |     |     |     |     |     | 775 |     |     |     | 780 |     |     |     |     |

| Ile | Ala | Glu | Lys | Glu | Glu | Arg | Val | Ser | Glu | Leu | Arg | His | Gln | Leu | Gln |
| 785 |     |     |     |     | 790 |     |     |     |     | 795 |     |     |     |     | 800 |

| Ser | Arg | Gln | Gln | Leu | Arg | Ser | Arg | Arg | His | Pro | Pro | Thr | Pro | Pro | Glu |
|     |     |     | 805 |     |     |     |     | 810 |     |     |     | 815 |     |     |     |

| Pro | Ser | Gly | Gly | Leu | Pro | Arg | Gly | Pro | Pro | Glu | Pro | Pro | Asp | Arg | Leu |
|     |     |     | 820 |     |     |     |     | 825 |     |     |     | 830 |     |     |     |

| Ser | Cys | Asp | Gly | Ser | Arg | Val | His | Leu | Leu | Tyr | Lys |
|     |     | 835 |     |     |     |     | 840 |     |     |     |     |